US011234626B2

(12) United States Patent
Bullington et al.

(10) Patent No.: US 11,234,626 B2
(45) Date of Patent: Feb. 1, 2022

(54) DEVICES AND METHODS FOR SYRINGE-BASED FLUID TRANSFER FOR BODILY-FLUID SAMPLING

(71) Applicant: Magnolia Medical Technologies, Inc., Seattle, WA (US)

(72) Inventors: Gregory J. Bullington, Bellevue, WA (US); Shan E. Gaw, Seattle, WA (US); Jay M. Miazga, Seattle, WA (US); Shannon E. Eubanks, Woodinville, WA (US); Richard G. Patton, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 997 days.

(21) Appl. No.: 15/180,454

(22) Filed: Jun. 13, 2016

(65) Prior Publication Data

US 2016/0361006 A1 Dec. 15, 2016

Related U.S. Application Data

(60) Provisional application No. 62/174,890, filed on Jun. 12, 2015.

(51) Int. Cl.
*A61B 5/15* (2006.01)
*A61B 5/154* (2006.01)
(Continued)

(52) U.S. Cl.
CPC ........ *A61B 5/150267* (2013.01); *A61B 5/153* (2013.01); *A61B 5/15003* (2013.01);
(Continued)

(58) Field of Classification Search
CPC ........ A61B 5/150267; A61B 5/150274; A61B 5/150251; A61B 5/15003;
(Continued)

(56) References Cited

U.S. PATENT DOCUMENTS 2,707,953 A    5/1955    Ryan
2,992,974 A    7/1961    Belcove et al.
(Continued)

FOREIGN PATENT DOCUMENTS

CN    2907683 Y      6/2007
CN    101060871 A   10/2007
(Continued)

OTHER PUBLICATIONS

Office Action for U.S. Appl. No. 11/955,635, dated Jul. 22, 2010, 11 pages.
(Continued)

*Primary Examiner* — Matthew Kremer
*Assistant Examiner* — Avery M Foley
(74) *Attorney, Agent, or Firm* — Cooley LLP

(57) ABSTRACT

An apparatus includes a housing, defining an inner volume, and an actuator mechanism movably disposed therein. The actuator mechanism is configured to be transitioned from a first configuration to a second configuration to define a pre-sample reservoir fluidically couplable to receive a pre-sample volume of bodily-fluid via an inlet port of the housing. The actuator mechanism is movable from a first position to a second position within the housing after the pre-sample reservoir receives the pre-sample volume such that the housing and the actuator mechanism collectively define a sample reservoir to receive a sample volume of bodily-fluid via the inlet port. The outlet port is in fluid communication with the sample reservoir and is configured to be fluidically coupled to an external fluid reservoir after the sample volume is disposed in the sample reservoir to transfer at least a portion of the sample volume into the external fluid reservoir.

16 Claims, 30 Drawing Sheets

(51) Int. Cl.
*A61B 5/153* (2006.01)
*B01L 3/02* (2006.01)

(52) U.S. Cl.
CPC ........ *A61B 5/154* (2013.01); *A61B 5/150099* (2013.01); *A61B 5/150236* (2013.01); *A61B 5/150244* (2013.01); *A61B 5/150251* (2013.01); *A61B 5/150312* (2013.01); *A61B 5/150732* (2013.01); *A61B 5/150755* (2013.01); *A61B 5/150946* (2013.01); *A61B 5/150992* (2013.01); *B01L 3/0217* (2013.01); *A61B 5/15074* (2013.01); *A61B 5/150221* (2013.01); *A61B 5/150389* (2013.01); *A61B 5/150503* (2013.01); *A61B 5/150572* (2013.01); *B01L 2300/0672* (2013.01); *B01L 2300/0832* (2013.01); *B01L 2400/0478* (2013.01)

(58) Field of Classification Search
CPC ........ A61B 5/150099; A61B 5/150236; A61B 5/150244; A61B 5/150312; A61B 5/150732; A61B 5/150755; A61B 5/150946; A61B 5/150992; A61B 5/153; A61B 5/154; A61B 5/150221; A61B 5/150389; A61B 5/150503; A61B 5/150572; A61B 5/15074; B01L 3/0217; B01L 2300/0672; B01L 2300/0832; B01L 2400/0478
See application file for complete search history.

(56) References Cited

U.S. PATENT DOCUMENTS

| | | | |
|---|---|---|---|
| 3,013,557 A | 12/1961 | Pallotta |
| 3,098,016 A | 7/1963 | Cooper et al. |
| 3,382,865 A | 5/1968 | Worral, Jr. |
| 3,405,706 A | 10/1968 | Cinqualbre |
| 3,467,095 A | 9/1969 | Ross |
| 3,494,351 A | 2/1970 | Horn |
| 3,494,352 A | 2/1970 | Russo et al. |
| 3,577,980 A | 5/1971 | Cohen |
| 3,604,410 A | 9/1971 | Whitacre |
| 3,635,798 A | 1/1972 | Kirkham et al. |
| 3,648,684 A | 3/1972 | Barnwell et al. |
| 3,680,558 A | 8/1972 | Kapelowitz |
| 3,730,168 A | 5/1973 | Mcwhorter |
| 3,741,197 A | 6/1973 | Sanz et al. |
| 3,777,773 A | 12/1973 | Tolbert |
| 3,803,810 A | 4/1974 | Rosenberg |
| 3,817,240 A | 6/1974 | Ayres |
| 3,831,602 A | 8/1974 | Broadwin |
| 3,834,372 A | 9/1974 | Turney |
| 3,835,835 A | 9/1974 | Thompson et al. |
| 3,848,579 A | 11/1974 | Villa-Real |
| 3,848,581 A | 11/1974 | Cinqualbre et al. |
| 3,874,367 A | 4/1975 | Ayres |
| 3,886,930 A | 6/1975 | Ryan |
| 3,890,203 A | 6/1975 | Mehl |
| 3,890,968 A | 6/1975 | Pierce et al. |
| 3,937,211 A | 2/1976 | Merten |
| 3,945,380 A | 5/1976 | Dabney et al. |
| 3,960,139 A | 6/1976 | Bailey |
| 3,978,846 A | 9/1976 | Bailey |
| 4,056,101 A | 11/1977 | Geissler et al. |
| 4,057,050 A | 11/1977 | Sarstedt |
| 4,063,460 A | 12/1977 | Svensson |
| 4,077,395 A | 3/1978 | Woolner |
| 4,106,497 A | 8/1978 | Percarpio |
| 4,133,863 A | 1/1979 | Koenig |
| 4,150,089 A | 4/1979 | Linet |
| 4,154,229 A | 5/1979 | Nugent |
| 4,166,450 A | 9/1979 | Abramson |
| 4,190,426 A | 2/1980 | Ruschke |
| 4,193,400 A | 5/1980 | Loveless et al. |
| 4,207,870 A | 6/1980 | Eldridge |
| 4,210,173 A | 7/1980 | Choksi et al. |
| 4,212,308 A | 7/1980 | Percarpio |
| 4,238,207 A | 12/1980 | Ruschke |
| 4,257,416 A | 3/1981 | Prager |
| 4,275,730 A | 6/1981 | Hussein |
| 4,298,358 A | 11/1981 | Ruschke |
| 4,340,067 A | 7/1982 | Rattenborg |
| 4,340,068 A | 7/1982 | Kaufman |
| 4,349,035 A | 9/1982 | Thomas et al. |
| 4,370,987 A | 2/1983 | Bazell et al. |
| 4,398,544 A | 8/1983 | Nugent et al. |
| 4,411,275 A | 10/1983 | Raitto |
| 4,412,548 A | 11/1983 | Hoch |
| 4,416,290 A | 11/1983 | Lutkowski |
| 4,425,235 A | 1/1984 | Cornell et al. |
| 4,444,203 A | 4/1984 | Engelman |
| 4,459,997 A | 7/1984 | Sarstedt |
| 4,509,534 A | 4/1985 | Tassin, Jr. |
| 4,608,996 A | 9/1986 | Brown |
| 4,654,027 A | 3/1987 | Dragan et al. |
| 4,657,027 A | 4/1987 | Paulsen |
| 4,657,160 A | 4/1987 | Woods et al. |
| 4,673,386 A | 6/1987 | Gordon |
| 4,676,256 A | 6/1987 | Golden |
| 4,679,571 A | 7/1987 | Frankel et al. |
| 4,705,497 A | 10/1987 | Shitaokoshi et al. |
| 4,714,461 A | 12/1987 | Gabel |
| 4,715,854 A | 12/1987 | Vaillancourt |
| 4,772,273 A | 9/1988 | Alchas |
| 4,820,287 A | 4/1989 | Leonard |
| 4,865,583 A | 9/1989 | Tu |
| 4,879,098 A | 11/1989 | Oberhardt et al. |
| 4,886,072 A | 12/1989 | Percarpio et al. |
| 4,890,627 A | 1/1990 | Haber et al. |
| 4,904,240 A | 2/1990 | Hoover |
| 4,980,297 A | 12/1990 | Haynes et al. |
| 5,009,847 A | 4/1991 | Solomons |
| 5,027,827 A | 7/1991 | Cody et al. |
| 5,032,116 A | 7/1991 | Peterson et al. |
| 5,045,185 A | 9/1991 | Ohnaka et al. |
| 5,066,284 A | 11/1991 | Mersch et al. |
| 5,084,034 A | 1/1992 | Zanotti |
| 5,097,842 A | 3/1992 | Bonn |
| 5,100,394 A | 3/1992 | Dudar et al. |
| 5,108,927 A | 4/1992 | Dom |
| 5,116,323 A | 5/1992 | Kreuzer et al. |
| 5,122,129 A | 6/1992 | Olson et al. |
| 5,135,489 A | 8/1992 | Jepson et al. |
| 5,222,502 A | 6/1993 | Kurose |
| 5,269,317 A | 12/1993 | Bennett |
| 5,330,464 A | 7/1994 | Mathias et al. |
| 5,360,011 A | 11/1994 | McCallister |
| 5,395,339 A | 3/1995 | Talonn et al. |
| 5,417,673 A | 5/1995 | Gordon |
| 5,429,610 A | 7/1995 | Vaillancourt |
| 5,431,811 A | 7/1995 | Tusini et al. |
| 5,439,450 A | 8/1995 | Haedt |
| 5,450,856 A | 9/1995 | Norris |
| 5,454,786 A | 10/1995 | Harris |
| 5,466,228 A | 11/1995 | Evans |
| 5,472,605 A | 12/1995 | Zuk, Jr. |
| 5,485,854 A | 1/1996 | Hollister |
| 5,507,299 A | 4/1996 | Roland |
| 5,520,193 A | 5/1996 | Suzuki et al. |
| 5,522,804 A | 6/1996 | Lynn |
| 5,575,777 A | 11/1996 | Cover et al. |
| 5,577,513 A | 11/1996 | Van Vlassalaer |
| 5,603,700 A | 2/1997 | Daneshvar |
| 5,632,906 A | 5/1997 | Ishida et al. |
| 5,649,912 A | 7/1997 | Peterson |
| 5,691,486 A | 11/1997 | Behringer et al. |
| 5,749,857 A | 5/1998 | Cuppy |
| 5,762,633 A | 6/1998 | Whisson |
| 5,772,608 A | 6/1998 | Dhas |
| 5,785,682 A | 7/1998 | Grabenkort |
| 5,811,658 A | 9/1998 | Van Driel et al. |
| 5,824,001 A | 10/1998 | Erskine |

(56) References Cited

U.S. PATENT DOCUMENTS

| | | | |
|---|---|---|---|
| 5,865,812 A | 2/1999 | Correia | |
| 5,871,699 A | 2/1999 | Ruggeri | |
| 5,882,318 A | 3/1999 | Boyde | |
| 5,911,705 A | 6/1999 | Howell | |
| 5,922,551 A | 7/1999 | Durbin et al. | |
| 5,961,472 A * | 10/1999 | Swendson | A61M 5/3148 |
| | | | 600/573 |
| 5,971,956 A | 10/1999 | Epstein | |
| 5,980,830 A | 11/1999 | Savage et al. | |
| 6,001,307 A | 12/1999 | Naka et al. | |
| 6,010,633 A | 1/2000 | Zuk, Jr. et al. | |
| 6,016,712 A | 1/2000 | Warden et al. | |
| 6,057,105 A | 5/2000 | Hoon et al. | |
| 6,106,509 A | 8/2000 | Loubser | |
| 6,126,643 A | 10/2000 | Vaillancouert | |
| 6,159,164 A | 12/2000 | Neese et al. | |
| 6,210,909 B1 | 4/2001 | Guirguis | |
| 6,224,561 B1 | 5/2001 | Swendson et al. | |
| 6,254,581 B1 | 7/2001 | Scott | |
| 6,299,131 B1 | 10/2001 | Ryan | |
| 6,325,975 B1 | 12/2001 | Naka et al. | |
| 6,328,726 B1 | 12/2001 | Ishida et al. | |
| 6,355,023 B1 | 3/2002 | Roth et al. | |
| 6,364,890 B1 | 4/2002 | Lum et al. | |
| 6,368,306 B1 | 4/2002 | Koska | |
| 6,387,086 B2 | 5/2002 | Mathias et al. | |
| 6,403,381 B1 | 6/2002 | Mann et al. | |
| 6,506,182 B2 | 1/2003 | Estabrook et al. | |
| 6,511,439 B1 | 1/2003 | Tabata et al. | |
| 6,520,948 B1 | 2/2003 | Mathias et al. | |
| 6,569,117 B1 | 5/2003 | Ziv et al. | |
| 6,592,555 B1 | 7/2003 | Wen-Pi | |
| 6,626,884 B1 | 9/2003 | Dillon et al. | |
| 6,638,252 B2 | 10/2003 | Moulton et al. | |
| 6,648,835 B1 | 11/2003 | Shemesh | |
| 6,692,479 B2 | 2/2004 | Kraus et al. | |
| 6,695,004 B1 | 2/2004 | Raybuck | |
| 6,716,187 B1 | 4/2004 | Jorgensen et al. | |
| 6,733,433 B1 | 5/2004 | Fell | |
| 6,736,783 B2 | 5/2004 | Blake et al. | |
| 6,746,420 B1 | 6/2004 | Prestidge et al. | |
| 6,843,775 B2 | 1/2005 | Hyun | |
| 6,860,871 B2 | 3/2005 | Kuracina et al. | |
| 6,905,483 B2 | 6/2005 | Newby et al. | |
| 6,913,580 B2 | 7/2005 | Stone | |
| 6,945,948 B2 | 9/2005 | Bainbridge et al. | |
| 7,044,941 B2 | 5/2006 | Mathias et al. | |
| 7,052,603 B2 | 5/2006 | Schick | |
| 7,055,401 B2 | 6/2006 | Prybella et al. | |
| 7,087,047 B2 | 8/2006 | Kraus et al. | |
| 7,141,097 B2 | 11/2006 | Leahey | |
| 7,241,281 B2 | 7/2007 | Coelho et al. | |
| 7,306,736 B2 | 12/2007 | Collins et al. | |
| 7,314,452 B2 | 1/2008 | Madonia | |
| 7,316,662 B2 | 1/2008 | Delnevo et al. | |
| 7,335,188 B2 | 2/2008 | Graf | |
| 7,351,228 B2 | 4/2008 | Keane et al. | |
| 7,384,416 B2 | 6/2008 | Goudaliez et al. | |
| 7,461,671 B2 | 12/2008 | Ehwald et al. | |
| 7,479,131 B2 | 1/2009 | Mathias et al. | |
| 7,614,857 B2 | 11/2009 | Fuechslin et al. | |
| 7,615,033 B2 | 11/2009 | Leong | |
| 7,618,407 B2 | 11/2009 | Demay et al. | |
| 7,648,491 B2 | 1/2010 | Rogers | |
| 7,666,166 B1 | 2/2010 | Emmert et al. | |
| 7,744,573 B2 | 6/2010 | Gordon et al. | |
| 7,766,879 B2 | 8/2010 | Tan et al. | |
| 8,070,725 B2 | 12/2011 | Christensen | |
| 8,197,420 B2 | 6/2012 | Patton | |
| 8,231,546 B2 | 7/2012 | Patton | |
| 8,287,499 B2 | 10/2012 | Miyasaka | |
| 8,337,418 B2 | 12/2012 | Patton | |
| 8,349,254 B2 | 1/2013 | Hoshino et al. | |
| 8,377,040 B2 | 2/2013 | Burkholz et al. | |
| 8,382,712 B2 | 2/2013 | Kim | |
| 8,383,044 B2 | 2/2013 | Davis et al. | |
| 8,412,300 B2 | 4/2013 | Sonderegger | |
| 8,523,826 B2 | 9/2013 | Layton, Jr. | |
| 8,535,241 B2 * | 9/2013 | Bullington | A61B 5/15003 |
| | | | 600/579 |
| 8,540,663 B2 | 9/2013 | Davey et al. | |
| 8,568,371 B2 | 10/2013 | Siopes et al. | |
| 8,574,203 B2 | 11/2013 | Stout et al. | |
| 8,603,009 B2 | 12/2013 | Tan et al. | |
| 8,647,286 B2 | 2/2014 | Patton | |
| 8,795,198 B2 | 8/2014 | Tan et al. | |
| 8,827,958 B2 | 9/2014 | Bierman et al. | |
| 8,864,684 B2 | 10/2014 | Bullington et al. | |
| 8,876,734 B2 | 11/2014 | Patton | |
| 9,022,950 B2 | 5/2015 | Bullington et al. | |
| 9,022,951 B2 | 5/2015 | Bullington et al. | |
| 9,060,724 B2 | 6/2015 | Bullington et al. | |
| 9,060,725 B2 | 6/2015 | Bullington et al. | |
| 9,138,572 B2 | 9/2015 | Zeytoonian et al. | |
| 9,155,495 B2 | 10/2015 | Bullington et al. | |
| 9,204,864 B2 | 12/2015 | Bullington et al. | |
| 9,314,201 B2 | 4/2016 | Burkholz et al. | |
| 9,820,682 B2 | 11/2017 | Rogers et al. | |
| 9,855,386 B2 | 1/2018 | Close et al. | |
| 9,895,092 B2 | 2/2018 | Burkholz | |
| 9,950,084 B2 | 4/2018 | Bullington et al. | |
| 9,980,878 B2 | 5/2018 | Marici et al. | |
| 9,999,383 B2 | 6/2018 | Bullington et al. | |
| 10,086,142 B2 | 10/2018 | Tekeste | |
| 10,206,613 B2 | 2/2019 | Bullington et al. | |
| 10,219,982 B2 | 3/2019 | Weir et al. | |
| 10,251,590 B2 | 4/2019 | Bullington et al. | |
| 10,265,007 B2 | 4/2019 | Bullington et al. | |
| 2002/0002349 A1 | 1/2002 | Flaherty et al. | |
| 2002/0004647 A1 | 1/2002 | Leong | |
| 2002/0183651 A1 | 12/2002 | Hyun | |
| 2002/0193751 A1 | 12/2002 | Theeuwes et al. | |
| 2003/0013991 A1 | 1/2003 | Stone | |
| 2003/0055381 A1 | 3/2003 | Wilkinson | |
| 2003/0069543 A1 | 4/2003 | Carpenter et al. | |
| 2003/0105414 A1 | 6/2003 | Leong | |
| 2003/0208151 A1 * | 11/2003 | Kraus | A61B 5/412 |
| | | | 604/4.01 |
| 2004/0009542 A1 | 1/2004 | Dumont et al. | |
| 2004/0010228 A1 | 1/2004 | Swenson et al. | |
| 2004/0054283 A1 | 3/2004 | Corey et al. | |
| 2004/0054333 A1 | 3/2004 | Theeuwes et al. | |
| 2004/0127816 A1 | 7/2004 | Galvao | |
| 2004/0147855 A1 | 7/2004 | Marsden | |
| 2005/0004524 A1 | 1/2005 | Newby et al. | |
| 2005/0148993 A1 | 7/2005 | Mathias et al. | |
| 2005/0154368 A1 | 7/2005 | Lim et al. | |
| 2005/0161112 A1 | 7/2005 | Ehwald et al. | |
| 2005/0199077 A1 | 9/2005 | Prybella et al. | |
| 2005/0240161 A1 | 10/2005 | Crawford | |
| 2005/0245885 A1 | 11/2005 | Brown | |
| 2005/0273019 A1 | 12/2005 | Conway et al. | |
| 2005/0281713 A1 | 12/2005 | Hampsch et al. | |
| 2006/0251622 A1 | 11/2006 | Suzuki et al. | |
| 2006/0287639 A1 | 12/2006 | Sharp | |
| 2007/0088279 A1 | 4/2007 | Shue et al. | |
| 2007/0100250 A1 | 5/2007 | Kline | |
| 2007/0119508 A1 | 5/2007 | West et al. | |
| 2007/0287948 A1 | 12/2007 | Sakiewicz | |
| 2008/0086085 A1 | 4/2008 | Brown | |
| 2008/0108954 A1 | 5/2008 | Mathias et al. | |
| 2008/0167577 A1 | 7/2008 | Weilbacher et al. | |
| 2008/0254471 A1 | 10/2008 | Bordano | |
| 2008/0255523 A1 | 10/2008 | Grinberg | |
| 2008/0319346 A1 | 12/2008 | Crawford et al. | |
| 2009/0192447 A1 | 7/2009 | Andersen et al. | |
| 2009/0306601 A1 | 12/2009 | Shaw et al. | |
| 2010/0010372 A1 | 1/2010 | Brown et al. | |
| 2010/0042048 A1 | 2/2010 | Christensen | |
| 2010/0057004 A1 | 3/2010 | Christensen et al. | |
| 2010/0094171 A1 | 4/2010 | Conway et al. | |
| 2010/0152681 A1 | 6/2010 | Mathias | |
| 2010/0268118 A1 | 10/2010 | Schweiger | |
| 2010/0286513 A1 | 11/2010 | Pollard et al. | |

(56) References Cited

U.S. PATENT DOCUMENTS

| | | | |
|---|---|---|---|
| 2011/0306899 A1 | 12/2011 | Brown et al. | |
| 2012/0022404 A1* | 1/2012 | Fojtik | A61B 5/153 600/578 |
| 2012/0035540 A1 | 2/2012 | Ferren et al. | |
| 2012/0265099 A1 | 10/2012 | Goodnow, II et al. | |
| 2012/0265128 A1 | 10/2012 | Kolln | |
| 2014/0066880 A1 | 3/2014 | Prince et al. | |
| 2014/0124542 A1 | 5/2014 | Kojima et al. | |
| 2014/0155782 A1 | 6/2014 | Bullington et al. | |
| 2014/0163419 A1 | 6/2014 | Bullington et al. | |
| 2015/0018715 A1 | 1/2015 | Walterspiel | |
| 2015/0025454 A1 | 1/2015 | Wetzel et al. | |
| 2015/0025455 A1 | 1/2015 | Shetty et al. | |
| 2015/0025456 A1 | 1/2015 | Shetty et al. | |
| 2015/0094615 A1 | 4/2015 | Patton | |
| 2015/0257691 A1 | 9/2015 | Bullington et al. | |
| 2015/0342510 A1 | 12/2015 | Bullington et al. | |
| 2016/0113560 A1 | 4/2016 | Bullington et al. | |
| 2016/0135724 A1 | 5/2016 | Bullington et al. | |
| 2016/0174888 A1 | 6/2016 | Berthier et al. | |
| 2016/0213294 A1 | 7/2016 | Patton | |
| 2017/0020427 A1 | 1/2017 | Rogers et al. | |
| 2017/0020428 A1 | 1/2017 | Rogers et al. | |
| 2017/0071519 A1 | 3/2017 | Gelfand et al. | |
| 2019/0159711 A1 | 5/2019 | Rogers et al. | |

FOREIGN PATENT DOCUMENTS

| | | | |
|---|---|---|---|
| CN | 101437450 A | 5/2009 | |
| CN | 101352357 A | 3/2010 | |
| CN | 101676001 A | 3/2010 | |
| CN | 101801445 A | 8/2010 | |
| CN | 103027727 A | 4/2013 | |
| DE | 7 203 008 U | 5/1972 | |
| DE | 2 203 858 B2 | 5/1973 | |
| DE | 2 541 494 A1 | 3/1977 | |
| DE | 299 13 417 U1 | 12/2000 | |
| DE | 100 38 026 A1 | 2/2001 | |
| DE | 101 34 913 A1 | 2/2003 | |
| DE | 101 34 913 C2 | 2/2003 | |
| DE | 102 43 129 A1 | 4/2004 | |
| EP | 0 207 304 A1 | 1/1987 | |
| EP | 0 448 795 A2 | 10/1991 | |
| JP | S48-046180 A | 7/1973 | |
| JP | 07-016219 A | 1/1995 | |
| WO | WO 90/04351 A1 | 5/1990 | |
| WO | WO 1991/018632 | 12/1991 | |
| WO | WO 1992/16144 A1 | 10/1992 | |
| WO | WO 1997/018845 | 5/1997 | |
| WO | WO 1999/013925 A1 | 3/1999 | |
| WO | WO 2000/024313 | 5/2000 | |
| WO | WO 2000/041624 | 7/2000 | |
| WO | WO 2001/008546 A2 | 2/2001 | |
| WO | WO 2002/051520 A1 | 7/2002 | |
| WO | WO 2003/008012 A2 | 1/2003 | |
| WO | WO 2005/068011 | 7/2005 | |
| WO | WO 2006/031500 | 3/2006 | |
| WO | WO 2007/033319 A1 | 3/2007 | |
| WO | WO 2008/101025 A1 | 8/2008 | |
| WO | WO 2011/069145 A2 | 6/2011 | |
| WO | WO 2012/012127 A2 | 1/2012 | |
| WO | WO 2014/022750 | 2/2014 | |
| WO | WO 2014/085800 | 6/2014 | |
| WO | WO-2014085800 A1 * | 6/2014 | ....... A61B 5/150389 |
| WO | WO 2016/054252 | 4/2016 | |

OTHER PUBLICATIONS

Office Action for U.S. Appl. No. 11/955,635, dated Dec. 3, 2010, 11 pages.

Office Action for U.S. Appl. No. 13/335,241, dated Apr. 20, 2012, 12 pages.

Office Action for U.S. Appl. No. 13/458,508, dated Jul. 24, 2012, 13 pages.

Office Action for U.S. Appl. No. 13/675,295, dated May 23, 2013, 15 pages.

Office Action for U.S. Appl. No. 14/089,267, dated Jun. 19, 2014, 13 pages.

Office Action for U.S. Appl. No. 14/498,102, dated Oct. 17, 2017, 20 pages.

Office Action for U.S. Appl. No. 14/498,102, dated Sep. 24, 2018, 18 pages.

Office Action for U.S. Appl. No. 15/088,842, dated Nov. 23, 2016, 20 pages.

Office Action for U.S. Appl. No. 15/432,310, dated Apr. 12, 2017, 14 pages.

Office Action for U.S. Appl. No. 15/435,684, dated Jun. 12, 2017, 28 pages.

Office Action for U.S. Appl. No. 15/448,891, dated Jun. 16, 2017, 34 pages.

Office Action for U.S. Appl. No. 15/457,082, dated Jun. 15, 2017, 22 pages.

Office Action for U.S. Appl. No. 15/829,015, dated Feb. 6, 2018, 24 pages.

Office Action for U.S. Appl. No. 15/829,018, dated Feb. 16, 2018, 24 pages.

Office Action for U.S. Appl. No. 15/829,023, dated Feb. 7, 2018, 25 pages.

Office Action for U.S. Appl. No. 15/832,055, dated Feb. 8, 2018, 21 pages.

Office Action for U.S. Appl. No. 15/832,087, dated Feb. 7, 2018, 24 pages.

Office Action for U.S. Appl. No. 13/954,528, dated Mar. 17, 2014, 10 pages.

Office Action for U.S. Appl. No. 15/832,091, dated Feb. 22, 2018, 16 pages.

Office Action for U.S. Appl. No. 16/299,962, dated May 2, 2019, 14 pages.

Office Action for U.S. Appl. No. 16/299,962, dated Dec. 26, 2019, 14 pages.

Office Action for U.S. Appl. No. 14/493,796, dated Jan. 27, 2015, 7 pages.

Office Action for U.S. Appl. No. 14/494,208, dated Jan. 27, 2015, 7 pages.

Office Action for U.S. Appl. No. 14/662,676, dated Sep. 5, 2018, 25 pages.

Office Action for U.S. Appl. No. 14/712,437 dated Oct. 25, 2018, 20 pages.

Office Action for U.S. Appl. No. 15/854,273, dated Sep. 7, 2018, 15 pages.

Office Action for U.S. Appl. No. 15/854,273, dated Jan. 13, 2020, 13 pages.

Office Action for U.S. Appl. No. 14/096,826, dated Jul. 26, 2017, 12 pages.

Office Action for U.S. Appl. No. 14/096,826, dated Mar. 8, 2018, 14 pages.

Office Action for U.S. Appl. No. 14/728,318, dated May 19, 2017, 26 pages.

Office Action for U.S. Appl. No. 14/728,318, dated Jan. 8, 2018, 36 pages.

Office Action for U.S. Appl. No. 14/728,318, dated Dec. 20, 2018, 26 pages.

Office Action for U.S. Appl. No. 13/952,964, dated Mar. 20, 2015, 11 pages.

Office Action for U.S. Appl. No. 14/926,784, dated May 25, 2018, 15 pages.

Office Action for U.S. Appl. No. 14/926,784, dated Jan. 15, 2019, 15 pages.

Office Action for U.S. Appl. No. 14/264,481, dated Jul. 1, 2015, 13 pages.

Office Action for U.S. Appl. No. 14/264,481, dated Feb. 26, 2016, 10 pages.

Office Action for U.S. Appl. No. 14/264,481, dated Jul. 14, 2016, 9 pages.

Office Action for U.S. Appl. No. 14/264,481, dated Oct. 21, 2016, 10 pages.

(56) References Cited

OTHER PUBLICATIONS

Office Action for U.S. Appl. No. 14/264,481, dated Apr. 13, 2017, 14 pages.
Office Action for U.S. Appl. No. 14/264,481, dated Sep. 7, 2017, 12 pages.
Office Action for U.S. Appl. No. 14/880,397, dated Apr. 17, 2018, 6 pages.
Office Action for U.S. Appl. No. 14/880,397, dated Sep. 24, 2018, 5 pages.
International Search Report and Written Opinion for International Application No. PCT/US2007/087951 dated May 16, 2008, 8 pages.
Examination Report for United Kingdom Application No. GB1805101.1, dated May 25, 2018, 8 pages.
International Search Report and Written Opinion for International Application No. PCT/US2013/071491, dated Aug. 5, 2014, 9 pages.
Notification of the First Office Action for Chinese Application No. 201380040468.7, dated Jun. 30, 2016, 9 pages.
Supplementary European Search Report for European Application No. 13797732.8, dated Dec. 7, 2015, 6 pages.
International Search Report and Written Opinion for International Application No. PCT/US2013/043289, dated Oct. 24, 2013, 15 pages.
Notification of the First Office Action for Chinese Application No. 201380072185.0, dated Sep. 28, 2016, 9 pages.
Supplementary European Search Report for European Application No. 13860741.1, dated Jun. 7, 2016, 6 pages.
Extended European Search Report for European Application No. 17204012.3, dated Feb. 14, 2018, 7 pages.
International Search Report and Written Opinion for International Application No. PCT/US2013/073080, dated Feb. 18, 2014, 14 pages.
Notice of Reasons for Rejection for Japanese Application No. 2015-545813, dated Jul. 4, 2017, 14 pages.
Notice of Reasons for Rejection for Japanese Application No. 2018-086721, with English translation, dated Mar. 15, 2019, 6 pages.
International Search Report and Written Opinion for International Application No. PCT/US2013/052493, dated Nov. 27, 2013, 7 pages.
Examination Report for Canadian Application No. 2,931,983, dated Oct. 16, 2019, 4 pages.
Office Action for Chinese Application No. 201380071681.4, dated Aug. 16, 2016, 9 pages.
Office Action for Chinese Application No. 201380071681.4, dated Jun. 28, 2017, 9 pages.
Extended European Search Report for European Application No. 13859067.4, dated Jun. 7, 2016, 4 pages.
Extended European Search Report for European Application No. 13859067.4, dated Jan. 27, 2017, 4 pages.
Extended European Search Report for European Application No. 13859067.4, dated Aug. 16, 2017, 6 pages.
Notice of Reasons for Rejection for Japanese Application No. 2015-545494, dated Jun. 19, 2017, 9 pages.
Extended European Search Report for European Application No. 18188136.8, dated May 16, 2019, 9 pages.
Notice of Reasons for Rejection for Japanese Application No. 2018-081980, dated Feb. 21, 2019, 7 pages.
International Search Report and Written Opinion for International Application No. PCT/US2013/072563, dated Feb. 7, 2014, 11 pages.
Extended European Search Report for European Application No. 16808502.5, dated Jan. 23, 2019, 5 pages.
International Search Report and Written Opinion for International Application No. PCT/US2016/037160, dated Sep. 30, 2016, 15 pages.
International Search Report and Written Opinion for International Application No. PCT/US2016/050380, dated Dec. 1, 2016, 6 pages.
International Search Report and Written Opinion for International Application No. PCT/US2018/36910, dated Sep. 4, 2018, 21 pages.
International Search Report and Written Opinion for International Application No. PCT/US2018/050621, dated Feb. 26, 2018, 11 pages.
International Search Report and Written Opinion for International Application No. PCT/US2018/064561, dated Feb. 11, 2019, 9 pages.
International Search Report and Written Opinion dated Aug. 22, 2019 for International Application No. PCT/US2019/034626, 16 pages.
Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.
BD Vacutainer Passive Shielding Blood Collection Needle Brochure; Becton Dickinson and Company (2005), 2 pages.
BD Saf-T-Intima Closed IV Catheter System, Becton, Dickinson and Company, 2015 Brochure. Retrieved from the Internet (Sep. 11, 2019) <https://www.bd.com/en-us/offerings/capabilities/infusion-therapy/iv-catheters/bd-saf-tintima-closed-iv-catheter-system>, 2 pages.
Barnard, D. R. & Arthur, M. M., "Fibronectin (cold insoluble globulin) in the neonate," Clinical and Laboratory Observations, 102(3): 453-455 (1983).
Baxter, "IV Tubing and Access Devices" authored by and published by Baxter, dated Nov. 6, 2006, 105 pages.
Brecher, M. E. et al., "Bacterial Contamination of Blood Components," Clinical Microbiology Reviews, 18(1):195-204 (2005).
Calam, R. R., "Recommended 'Order of Draw' for Collecting Blood Specimens Into Additive-Containing Tubes," Letter to the Editor, Clinical Chemistry, 28(6):1399 (1982).
Cartridge and Test Information, Abbott, Art: 714258-01O Rev. Date: Aug. 16, 2015, 6 pages.
Challiner, A. et al., Queen Alexandra Hospital, Portsmouth P06 3LY, "Venous/arterial blood management protection system," Correspondence, p. 169.
De Korte, D. et al., "Diversion of first blood volume results in a reduction of bacterial contamination for whole-blood collections," Vox Sanguinis, 83:13-16 (2002).
De Korte, D. et al., "Effects of skin disinfection method, deviation bag, and bacterial screening on clinical safety of platelet transfusions in the Netherlands," Transfusion, 46: 476-485 (2006).
Edwards Lifesciences, "Conservation. Safety. Simplicity. Edwards VAMP and VAMP Jr. Systems," 2002 Brochure. Retrieved from the Internet (Sep. 11, 2019) <https://www.medline.com/media/catalog/Docs/MKT/VAMPSYSTEMBROCHURE.PDF>, 4 pages.
Ernst, D. J. et al., "NCCLS simplifies the order of draw: a brief history," MLO, 26-27 (2004).
Gottlieb, T., "Hazards of Bacterial Contamination of Blood Products," Anaesth Intens Care, 21: 20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, 575-589 (2003).
Kim, J. Y. et al., "The Sum of the Parts is Greater Than the Whole: Reducing Blood Culture Contamination," Annals of Internal Medicine, 154:202-203 (2011).
Levin, P. D. et al., "Use of the Nonwire Central Line Hub to Reduce Blood Culture Contamination," Chest, 143(3):640-645 (2013).
"Leukotrap Filtration Systems for Whole Blood Derived Platelets: Leukotrap RC PL and Leukotrap PL Systems," 2005 Brochure, Pall Corporation, 2 pages.
Li, Y. et al., "Direct labeling and visualization of blood vessels with lipophilic carbocyanine dye DiI," Nature Protocols, 3(11): 1703-1708 (2008).
Liumbruno, G. M. et al., "Reduction of the risk of bacterial contamination of blood components through diversion of the first part of the donation of blood and blood components," Blood Transfus, 7: 86-93 (2009).
Mayer, G. A., "A Method for the Reliable Determination of Clotting Time in Whole Blood," Can Med Assoc J., 72(12): 927-929 (1955).
McDonald, C. P., "Interventions Implemented to Reduce the Risk of Transmission of Bacteria by Transfusion in the English National Blood Service," Transfus Med Hemother, 38:255-258 (2011).

(56) References Cited

OTHER PUBLICATIONS

Meissner, G. F. et al., "A Method Based on the Use of Whole Venous Blood in Capillary Tubes," American Journal of Clinical Pathology, 33(2): 29-31 (1963).
Murphy, M., "Better Blood Transfusion," Journal of the Intensive Core Society, 4(3): 78-80 (2003).
Napolitano, M. et al., "Quality control of bacterial contamination of blood components: the feasibility of diversion system testing," Blood Transfus, 2: 231-232 (2004).
Norberg, A. et al., "Contamination Rates of Blood Cultures Obtained by Dedicated Phlebotomy vs Intravenous Catheter," JAMA, 289(6): 726-729 (2003).
Order of Draw for Multiple Tube Collections, LabNotes, a newsletter from BD Diagnostics,—Preanalytical Systems, 17(1):3 (2007).
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).
Proehl, J. A. et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Schuur, J., "Blood Cultures: When Do they Help and When Do They Harm?" Brigham & Women's Hospital, Department of Emergency Medicine, (Jun. 21-23, 2012), 42 pages.
Sheppard, C. A. et al., "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1): 11-19 (2000).
Sibley, C. D. et al., "Molecular Methods for Pathogen and Microbial Community Detection and Characterization: Current and Potential Application in Diagnostic Microbiology," Infection, Genetics and Evolution 12:505-521 (2012).
Stohl, S. et al., "Blood Cultures at Central Line Insertion in the Intensive Care Unit: Comparison with Peripheral Venipuncture," Journal of Clinical Microbiology, 49(7):2398-2403 (2011).
Tang, M. et al., "Closed Blood Conservation Device for Reducing Catheter-Related Infections in Children After Cardiac Surgery," Critical Care Nurse, 34(5): 53-61 (2014).
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23:63-66 (2012).
Weinbaum, F. I. et al., "Doing It Right the First Time: Quality Improvement and the Contaminant Blood Culture," Journal of Clinical Microbiology, 35(3): 563-565 (1997).
Weinstein, M. P., "Current Blood Culture Methods and Systems: Clinical Concepts, Technology, and Interpretation of Results," Clinical Infectious Diseases, 23: 40-46 (1996).
Weinstein, M. P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Weinstein, M. P., "Minireview: Blood Culture Contamination: Persisting Problems and Partial Progress," Journal of Clinical Microbiology, 41(6): 2275-2278 (2003).
Ziegler, et al., "Controlled Clinical Laboratory Comparison of Two Supplemented Aerobic and Anaerobic Media Used in Automated Blood Culture Systems to Detect Bloodstream Infections," J. Clinical Microbiology, 36(3):657-661 (1998).
Zimmon, D. S. et al., "Effect of Portal Venous Blood Flow Diversion on Portal Pressure," J Clin Invest, 65(6): 1388-1397 (1980).
Zundert, A. V., "New Closed IV Catheter System," Acta Anaesth. Belg., 56: 283-285 (2005).
Exhibit 1—Defendant's Invalidity Contentions, Invalidity Claim Chart—U.S. Pat. No. 9,855,001 vs Barnard NPL, Aug. 30, 2019, 8 pages.
Exhibit 2—Defendant's Invalidity Contentions, Invalidity Claim Chart—U.S. Pat. No. 9,855,001 vs BD Needle NPL, Aug. 30, 2019, 7 pages.
Exhibit 3—Defendant's Invalidity Contentions, Invalidity Claim Chart—U.S. Pat. No. 9,855,001 vs U.S. Pat. No. 6,626,884, Aug. 30, 2019, 11 pages.
Exhibit 4—Defendant's Invalidity Contentions, Invalidity Claim Chart—U.S. Pat. No. 9,855,001 vs U.S. Pat. Pub. No. 2005/161112, Aug. 30, 2019, 22 pages.
Exhibit 5—Defendant's Invalidity Contentions, Invalidity Claim Chart—U.S. Pat. No. 9,855,001 vs U.S. Pat. No. 4,673,386, Aug. 30, 2019, 21 pages.
Exhibit 6—Defendant's Invalidity Contentions, Invalidity Claim Chart—U.S. Pat. No. 9,855,001 vs U.S. Pat. No. 4,904,240, Aug. 30, 2019, 15 pages.
Exhibit 7—Defendant's Invalidity Contentions, Invalidity Claim Chart—U.S. Pat. No. 9,855,001 vs Leukotrap NPL, Aug. 30, 2019, 38 pages.
Exhibit 9—Defendant's Invalidity Contentions, Invalidity Claim Chart—U.S. Pat. No. 9,855,001 vs U.S. Pat. No. 4,106,497, Aug. 30, 2019, 22 pages.
Exhibit 10—Defendant's Invalidity Contentions, Invalidity Claim Chart—U.S. Pat. No. 9,855,001 vs Stopcock-Syringe NPL, Aug. 30, 2019, 85 pages.
Exhibit 11—Defendant's Invalidity Contentions, Invalidity Claim Chart—U.S. Pat. No. 9,855,001 vs Ziegler NPL, Aug. 30, 2019, 8 pages.
Exhibit 12—Defendant's Invalidity Contentions, Invalidity Claim Chart—U.S. Pat. No. 10,028,689 vs Barnard NPL, Aug. 30, 2019, 12 pages.
Exhibit 13—Defendant's Invalidity Contentions, Invalidity Claim Chart—U.S. Pat. No. 10,028,689 vs U.S. Pat. No. 6,626,884, Aug. 30, 2019, 29 pages.
Exhibit 14—Defendant's Invalidity Contentions, Invalidity Claim Chart—U.S. Pat. No. 10,028,689 vs U.S. Pat. Pub. No. 2005/161112, Aug. 30, 2019, 48 pages.
Exhibit 15—Defendant's Invalidity Contentions, Invalidity Claim Chart—U.S. Pat. No. 10,028,689 vs U.S. Pat. No. 4,673,386, Aug. 30, 2019, 44 pages.
Exhibit 16—Defendant's Invalidity Contentions, Invalidity Claim Chart—U.S. Pat. No. 10,028,689 vs U.S. Pat. No. 4,904,240, Aug. 30, 2019, 31 pages.
Exhibit 17—Defendant's Invalidity Contentions, Invalidity Claim Chart—U.S. Pat. No. 10,028,689 vs Leukotrap NPL, Aug. 30, 2019, 113 pages.
Exhibit 19—Defendant's Invalidity Contentions, Invalidity Claim Chart—U.S. Pat. No. 10,028,689 vs U.S. Pat. No. 4,106,497, Aug. 30, 2019, 38 pages.
Exhibit 20—Defendant's Invalidity Contentions, Invalidity Claim Chart—U.S. Pat. No. 10,028,689 vs Stopcock-Syringe NPL, Aug. 30, 2019, 268 pages.
Exhibit 21—Defendant's Invalidity Contentions, Invalidity Claim Chart—U.S. Pat. No. 10,220,139 vs U.S. Pat. No. 6,626,884, Aug. 30, 2019, 35 pages.
Exhibit 22—Defendant's Invalidity Contentions, Invalidity Claim Chart—U.S. Pat. No. 10,220,139 vs U.S. Pat. Pub. No. 2005/161112, Aug. 30, 2019, 46 pages.
Exhibit 23—Defendant's Invalidity Contentions, Invalidity Claim Chart—U.S. Pat. No. 10,220,139 vs U.S. Pat. No. 4,207,870, Aug. 30, 2019, 20 pages.
Exhibit 24—Defendant's Invalidity Contentions, Invalidity Claim Chart—U.S. Pat. No. 10,220,139 vs U.S. Pat. No. 6,506,182, Aug. 30, 2019, 15 pages.

(56) References Cited

OTHER PUBLICATIONS

Exhibit 25—Defendant's Invalidity Contentions, Invalidity Claim Chart—U.S. Pat. No. 10,220,139 vs U.S. Pat. No. 4,673,386, Aug. 30, 2019, 53 pages.
Exhibit 26—Defendant's Invalidity Contentions, Invalidity Claim Chart—U.S. Pat. No. 10,220,139 vs U.S. Pat. No. 4,904,240, Aug. 30, 2019, 39 pages.
Exhibit 27—Defendant's Invalidity Contentions, Invalidity Claim Chart—U.S. Pat. No. 10,220,139 vs Leukotrap NPL, Aug. 30, 2019, 115 pages.
Exhibit 29—Defendant's Invalidity Contentions, Invalidity Claim Chart—U.S. Pat. No. 10,220,139 vs U.S. Pat. No. 4,106,497, Aug. 30, 2019, 45 pages.
Exhibit 30—Defendant's Invalidity Contentions, Invalidity Claim Chart—U.S. Pat. No. 10,220,139 vs Stopcock-Syringe NPL, Aug. 30, 2019, 246 pages.
Exhibit 31—Defendant's Invalidity Contentions, Invalidity Claim Chart—U.S. Pat. No. 10,220,139 vs U.S. Pat. No. 4,349,035, Aug. 30, 2019, 26 pages.
Exhibit 32—Defendant's Invalidity Contentions, Invalidity Claim Chart—U.S. Pat. No. 10,220,139 vs U.S. Pat. Pub. No. 2008/0145933A1, Aug. 30, 2019, 39 pages.
Exhibit 33—Defendant's Invalidity Contentions, Invalidity Claim Chart—U.S. Pat. No. 10,039,483 vs Barnard NPL, Aug. 30, 2019, 14 pages.
Exhibit 34—Defendant's Invalidity Contentions, Invalidity Claim Chart—U.S. Pat. No. 10,039,483 vs U.S. Pat. No. 6,626,884, Aug. 30, 2019, 22 pages.
Exhibit 35—Defendant's Invalidity Contentions, Invalidity Claim Chart—U.S. Pat. No. 10,039,483 vs U.S. Pat. Pub. No. 2005/161112, Aug. 30, 2019, 45 pages.
Exhibit 36—Defendant's Invalidity Contentions, Invalidity Claim Chart—U.S. Pat. No. 10,039,483 vs U.S. Pat. No. 4,673,386, Aug. 30, 2019, 47 pages.
Exhibit 37—Defendant's Invalidity Contentions, Invalidity Claim Chart—U.S. Pat. No. 10,039,483 vs U.S. Pat. No. 4,904,240, Aug. 30, 2019, 30 pages.
Exhibit 38—Defendant's Invalidity Contentions, Invalidity Claim Chart—U.S. Pat. No. 10,039,483 vs Leukotrap NPL, Aug. 30, 2019, 115 pages.
Exhibit 40—Defendant's Invalidity Contentions, Invalidity Claim Chart—U.S. Pat. No. 10,039,483 vs U.S. Pat. No. 4,106,497, Aug. 30, 2019, 45 pages.
Exhibit 41—Defendant's Invalidity Contentions, Invalidity Claim Chart—U.S. Pat. No. 10,039,483 vs Stopcock-Syringe NPL, Aug. 30, 2019, 214 pages.
Exhibit 42—Defendant's Invalidity Contentions, Invalidity Claim Chart—U.S. Pat. No. 10,039,483 vs U.S. Pat. Pub. No. 2008/0145933A1, Aug. 30, 2019, 38 pages.
Office Action for U.S. Appl. No. 14/926,784, dated Jan. 21, 2020, 17 pages.
Extended European Search Report for European Application No. 20176877.7, dated Dec. 1, 2020, 9 pages.

* cited by examiner

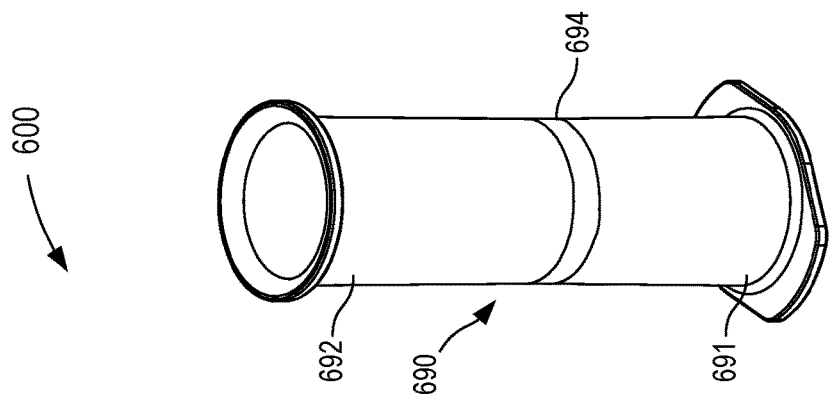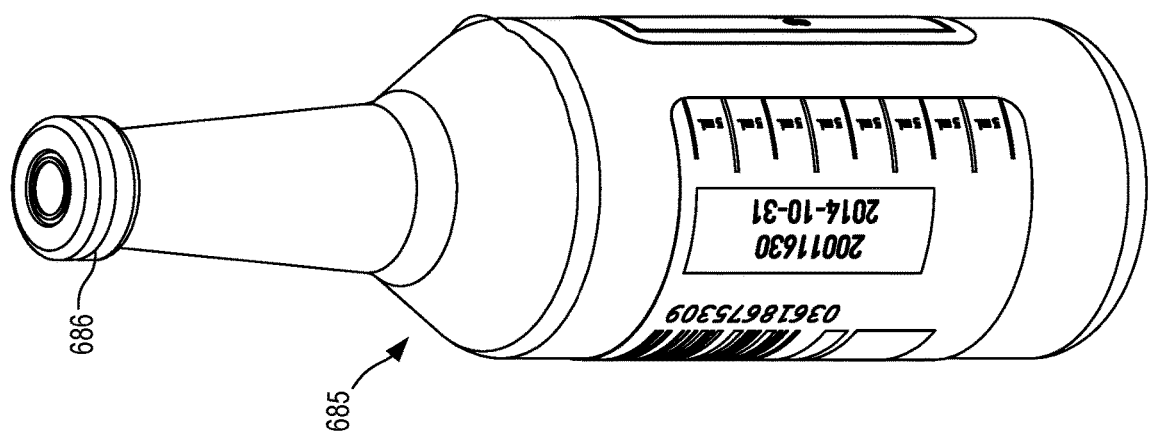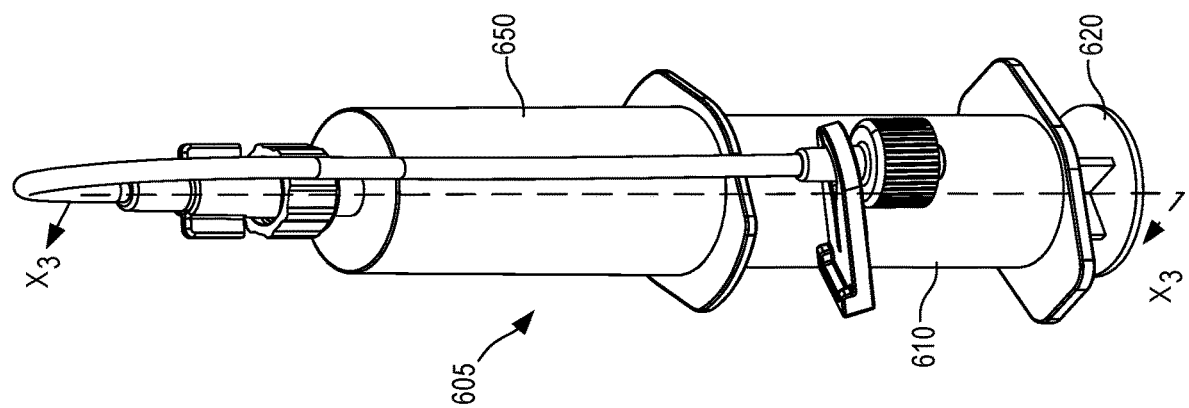
FIG. 18

DEVICES AND METHODS FOR SYRINGE-BASED FLUID TRANSFER FOR BODILY-FLUID SAMPLING

CROSS-REFERENCE TO RELATED APPLICATIONS

This application claims priority to and the benefit of U.S. Provisional Patent Application Ser. No. 62/174,890 entitled, "Devices and Methods for Syringe-Based Fluid Transfer for Bodily-Fluid Sampling," filed Jun. 12, 2015, the disclosure of which is incorporated herein by reference in its entirety.

BACKGROUND

Embodiments described herein relate generally to the parenteral procurement of bodily-fluid samples, and more particularly, to devices and methods for parenterally procuring bodily-fluid samples with reduced contamination from microbes or other contaminants exterior to the bodily-fluid source (e.g., dermally-residing microbes) via syringe-based fluid transfer and/or the like.

Health care practitioners routinely perform various types of tests (including microbial tests, tuberculosis tests, and the like) on patients using parenterally-obtained bodily-fluids. The in vitro diagnostics industry has expanded the types of approaches employed to identify, categorize, type, determine sensitivity and suitability (e.g., to specific antibiotics), and/or to otherwise discern desired information about bodily-fluid samples with increased speed, specificity, and accuracy. For example, some such approaches include DNA/RNA sequencing, biological marker identification, mass spectrometry, centrifuging, magnetic separation, microfluidic isolation, molecular analysis, polymerase chain reaction (PCR) analysis, interferon-gamma release assays, and/or the like. In some instances, such approaches can be used, for example, in microbial testing of parenterally obtained bodily-fluids to determine the presence of one or more potentially undesirable microbes, such as bacteria, fungi, or yeast (e.g., Candida).

In some instances, microbial testing may include diagnostic methods including but not limited to incubating patient samples in one or more sterile vessels containing culture media that is conducive to microbial growth, molecular sample analysis, gene sequencing, PCR-based approaches, mass spectrometry, and/or the like as noted above. Generally, when such microbes are present in the patient sample, the microbes flourish over time in the culture medium or can be detected and/or identified by one of the aforementioned technological approaches. When culture medium is utilized for microbial testing, after a variable amount of time (e.g., a few hours to several days), organism growth can be detected by automated, continuous monitoring (e.g., by detecting carbon dioxide and/or the like). The culture medium can then be tested for the presence of the microbes, which if present, suggests the presence of the same microbes in the patient sample and thus, in the bodily-fluid of the patient from which the sample was obtained. When other technologies are used for microbial testing, the amount of time required to determine a presence of microbes may vary (e.g. from nearly instantaneously to several minutes, hours, or days). These technologies, however, are still sensitive to the inherent quality and/or integrity of the specimen that is being analyzed. Accordingly, when microbes are determined to be present in the culture medium or identified by another diagnostic test, the patient may be prescribed one or more antibiotics or other treatments specifically designed to treat or otherwise remove the undesired microbes from the patient.

Patient samples, however, can become contaminated during procurement and/or otherwise can be susceptible to false positive results. For example, microbes from a bodily surface (e.g., dermally-residing microbes) that are dislodged during needle insertion into a patient, either directly or indirectly via tissue fragments, hair follicles, sweat glands, and other skin adnexal structures, can be subsequently transferred to a culture medium with the patient sample and/or included in the specimen that is to be analyzed for non-culture based testing. Another possible source of contamination is from the person drawing the patient sample. For example, a doctor, phlebotomist, nurse, etc. can transfer contaminants from their body (e.g., finger, arms, etc.) to the patient sample and/or to the equipment containing the patient sample. Specifically, equipment and/or devices used during a patient sample procurement process (e.g., patient to needle, needle/tubing to sample vessels, etc.) often include multiple fluidic interfaces that can each introduce points of potential contamination. In some instances, such contaminants may thrive in a culture medium and/or may be identified by another diagnostic technology and eventually yield a positive microbial test result, thereby falsely indicating the presence of such microbes in vivo.

In some instances, false positive results and/or false negative results can be attributed to a specific volume of the patient sample. For example, overfilling of volume-sensitive blood culture bottles can lead to false positive results as noted in the instructions for use and/or warning labeling from manufacturers of such culture bottles, as well as associated automated continuous monitoring microbial detection systems. On the other hand, insufficient patient sample volume within a culture medium can result in false negative results. By way of example, in a study performed by the Mayo Clinic entitled, Optimized Pathogen Detection with 30- Compared to 20-Milliliter Blood Culture Draws, Journal of Clinical Microbiology, December 2011, a patient sample volume of 20 milliliters (mL) can result in detection of about 80% of bacteremias present in a patient sample, a patient sample volume of 40 mL can result in detection of about 88% of the bacteremias, and a patient sample volume of 60 mL can result in detection of about 99% of the bacteremias. In some instances, such as in patients with sepsis, a concentration of colony forming units (CFUs) in the septic patient's bloodstream can be highly variable (including very low levels of less than 1 CFU per 10 ml of blood). Thus, ensuring that a sufficient amount of blood is collected and analyzed is desired for clinical confidence in the accuracy of the microbial test result.

While placing blood in a culture medium is a 'standard of care' today, a number of new technologies (examples of which are noted above) hold promise in increasing the pace with which microbes (and antibiotic susceptibility and/or sensitivity) can be identified in a bodily-fluid sample. However, procuring a sufficient volume of blood that is analyzed remains desirable as a small volume of blood may not contain a CFU that is actually present in the patient's bloodstream, thereby falsely indicating that a patient is not septic.

Such inaccurate results because of contamination, insufficient patient sample volume, and/or the like are a concern when attempting to diagnose or treat a suspected illness or condition. For example, false negative results from microbial tests may result in a misdiagnosis and/or delayed treatment of a patient illness, which, in some cases, could result in the death of the patient. Conversely, false positive results from microbial tests may result in the patient being unnecessarily subjected to one or more anti-microbial therapies, which may cause serious side effects to the patient including, for example, death, as well as produce an unnecessary burden and expense to the health care system due to extended length of patient stay and/or other complications associated with erroneous treatments. Additionally, the use of diagnostic imaging equipment attributable to these false positive results is also a concern from both a cost as well as patient safety perspective as unnecessary exposure to concentrated radiation associated with a variety of imaging procedures (e.g., CT scans) has many known adverse impacts on long-term patient health.

As such, a need exists for improved bodily-fluid transfer devices and methods that reduce microbial contamination in bodily-fluid test samples particularly in syringe-based fluid transfers.

SUMMARY

Devices for parenterally-procuring bodily-fluid samples with reduced contamination from microbes that are exterior to the bodily-fluid source, such as dermally-residing microbes, are described herein. In some embodiments, an apparatus includes a housing, defining an inner volume, and an actuator mechanism movably disposed therein. The actuator mechanism is configured to be transitioned from a first configuration to a second configuration to define a pre-sample reservoir fluidically couplable to receive a pre-sample volume of bodily-fluid via an inlet port of the housing. The actuator mechanism is movable from a first position to a second position within the housing after the pre-sample reservoir receives the pre-sample volume such that the housing and the actuator mechanism collectively define a sample reservoir to receive a sample volume of bodily-fluid via the inlet port. The outlet port is in fluid communication with the sample reservoir and is configured to be fluidically coupled to an external fluid reservoir after the sample volume is disposed in the sample reservoir to transfer at least a portion of the sample volume into the external fluid reservoir.

BRIEF DESCRIPTION OF THE DRAWINGS

FIG. 18 is a partially exploded view of a syringe-based transfer system according to an embodiment.

DETAILED DESCRIPTION

Figure 1:
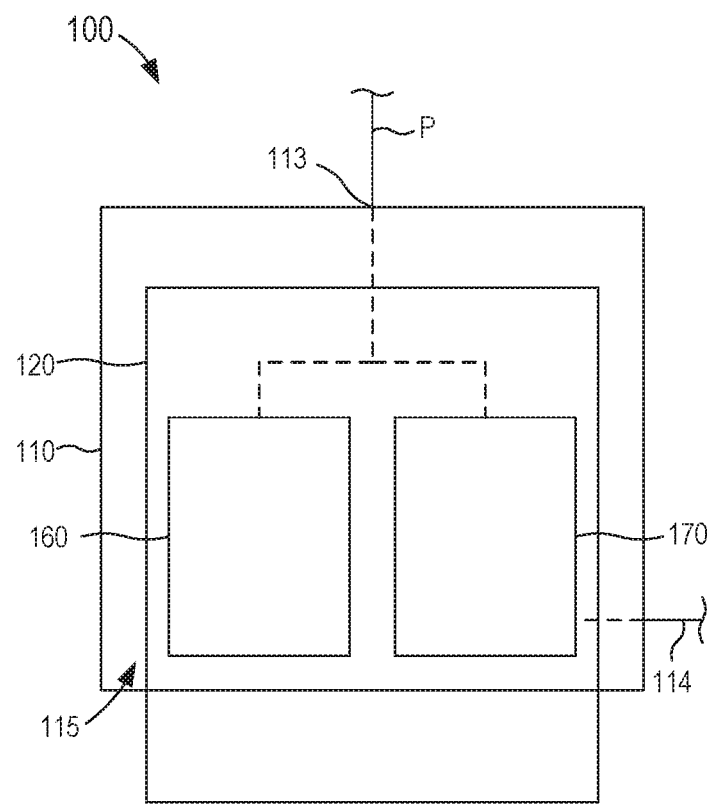
FIG. 1 is a schematic illustration of a syringe-based transfer device according to an embodiment.

Devices for parenterally-procuring bodily-fluid samples with reduced contamination from microbes that are exterior to the bodily-fluid source, such as dermally-residing microbes and/or other undesirable external contaminants that can distort diagnostic testing results are described herein. In some embodiments, an apparatus includes a housing, defining an inner volume, and an actuator mechanism movably disposed therein. The actuator mechanism is configured to be transitioned from a first configuration to a second configuration to define a pre-sample reservoir fluidically couplable to receive a pre-sample volume of bodily-fluid via an inlet port of the housing. The actuator mechanism is movable from a first position to a second position within the housing after the pre-sample reservoir receives the pre-sample volume such that the housing and the actuator mechanism collectively define a sample reservoir to receive a sample volume of bodily-fluid via the inlet port. The outlet port is in fluid communication with the sample reservoir and is configured to be fluidically coupled to an external fluid reservoir after the sample volume is disposed in the sample reservoir to transfer at least a portion of the sample volume into the external fluid reservoir.

In some embodiments, a system for syringe-based fluid transfer includes an adapter, a transfer device, and a coupler. The adapter includes a puncture member. The adapter is configured to place the puncture member in fluid communication with a portion of a patient. The transfer device includes a housing having an inlet port. The transfer device is configured to removably couple to the adapter such that a portion of the puncture member is disposed within the housing via the inlet port. The transfer device includes an actuator mechanism that defines a pre-sample reservoir. A portion of the actuator mechanism is movably disposed in the housing such that (1) the puncture member is in fluid communication with the pre-sample when the actuator mechanism is moved from a first configuration to a second configuration and (2) the puncture member is in fluid communication with a sample reservoir collectively defined by the housing and a portion of the actuator mechanism when the actuator mechanism is moved from the second configuration to a third configuration. The coupler has a first end portion that is configured to removably couple to the housing when the adapter is decoupled from the housing and a second end portion configured to removably couple to an external fluid reservoir. The coupler includes a medial portion configured to establish fluid communication between the transfer device and the external fluid reservoir when coupled therebetween.

In some embodiments, a method of using a syringe-based fluid transfer device having a housing and an actuator mechanism includes establishing fluid communication between a patient and the syringe-based transfer device. A first member of the actuator mechanism is moved relative to the housing from a first position to a second position. A portion of the first member moves within a second member of the actuator mechanism such that the first member and the second member collectively define a pre-sample reservoir. The pre-sample reservoir is in fluid communication with the patient as the first member is moved from the first position to the second position. A pre-sample volume of bodily-fluid is transferred to the pre-sample reservoir. After transferring the pre-sample volume, the first member is moved relative to the housing from the second position to a third position. The second member is moved by the first member when the first member moves from the second position to the third position such that a portion of the second member and a portion of the housing collectively define a sample reservoir fluidically isolated from the pre-sample reservoir. The sample reservoir is in fluid communication with the patient as the first member is moved from the second position to the third position. A sample volume is then transferred to the sample reservoir.

In some embodiments, a syringe-based device includes a housing defining an inner volume, and an actuator mechanism movably disposed therein. The housing has an inlet port in fluid communication with the inner volume and an outlet port in fluid communication with the inner volume. The inlet port is configured to receive bodily-fluids from the patient. The actuator mechanism is configured to be transitioned from a first configuration to a second configuration to define a pre-sample reservoir fluidically couplable to the inlet port to receive a pre-sample volume of bodily-fluid. The actuator mechanism is configured to be moved from a first position to a second position after the pre-sample volume of bodily-fluid is disposed in the pre-sample reservoir such that the housing and a portion of the actuator mechanism collectively define a sample reservoir configured to receive a sample volume of bodily-fluid via the inlet port. The actuator mechanism is configured to be moved from the second position toward the first position after the sample volume of bodily-fluid is disposed in the sample reservoir to expel at least a portion of the sample volume of bodily-fluid from the outlet port.

In some embodiments, a bodily-fluid transfer device can be configured to selectively divert a first, predetermined or variable amount of a flow of a bodily-fluid to a first reservoir before permitting the flow of a second amount of the bodily-fluid into a second reservoir. In this manner, the second amount of bodily-fluid can be used for diagnostic or other testing, while the first amount of bodily-fluid, which may contain microbes and/or other types of contaminants from a bodily surface and/or other external sources, is isolated from the bodily-fluid to be tested (e.g., to determine microbial presence, tuberculin, and/or the like) but can be used for other blood tests as ordered by clinician (e.g., complete blood count CBC).

As used in this specification, the term "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the terms "first, predetermined amount," "first amount," and "first volume" describe an amount of bodily-fluid received or contained by a first reservoir or a pre-sample reservoir. While the terms "first amount" and "first volume" do not explicitly describe a predetermined amount or volume, it should be understood that the first amount or first volume can be predetermined or can be variable. In some instances, a predetermined amount and/or predetermined volume can include a range of amounts and/or volumes. For example, in some instances, a predetermined amount of bodily-fluid can include a single drop of bodily fluid to a few drops of bodily-fluid. In some instances, a predetermined amount of bodily-fluid can include a range of amounts or fluids such as, for example, about 0.01 milliliters (mL) to about 10 mL or more. In other instances, a first amount or first volume of bodily-fluid need not be predetermined.

As used herein, the terms "second amount" and "second volume" describe an amount of bodily-fluid received or contained by a second reservoir or sample reservoir. The second amount can be any suitable amount of bodily-fluid and need not be predetermined. Conversely, when explicitly described as such, the second amount received and contained by the second reservoir or sample reservoir can be a second, predetermined amount.

FIG. 1 is a schematic illustration of a portion of a syringe-based transfer device 100, according to an embodiment. Generally, the syringe-based transfer device 100 (also referred to herein as "bodily-fluid transfer device," "transfer device," or "device") is configured to withdraw of bodily-fluid from a patient such that a first portion or amount of the withdrawn fluid is fluidically isolated and diverted away from a second portion or amount of the withdrawn fluid that is to be used as a biological sample, such as for testing for the purpose of medical diagnosis and/or treatment. In other words, the transfer device 100 can be a syringe-based device that is configured to transfer a first, predetermined amount of a bodily-fluid to a first collection reservoir and a second amount of bodily-fluid to one or more bodily-fluid collection reservoirs (e.g., sample reservoirs) fluidically isolated from the first collection reservoir, as described in more detail herein. In some embodiments, the transfer device 100 can be substantially similar to those described in U.S. Pat. No. 9,155,495 entitled, "Syringe-Based Fluid Diversion Mechanism For Bodily Fluid Sampling," filed Dec. 2, 2013, the disclosure of which is incorporated herein by reference in its entirety.

The transfer device 100 includes a housing 110, an actuator mechanism 120, a first fluid reservoir 160 (also referred to herein as "first reservoir" or "pre-sample reservoir"), and a second fluid reservoir 170 (also referred to herein as "second reservoir" or "sample reservoir"), different from the first reservoir 160. The housing 110 can be any suitable shape, size, or configuration and is described in further detail herein with respect to specific embodiments. As shown in FIG. 1, the housing 110 includes an inlet port 113 that can be at least temporarily physically and fluidically coupled to a medical device defining a pathway P for withdrawing and/or conveying the bodily-fluid from the patient to the transfer device 100. For example, the inlet port 113 can be a Luer-Lok® or the like that can be physically and fluidically coupled to a butterfly needle, a cannula, and/or other lumen-containing device. In other embodiments, the inlet port 113 can be monolithically formed with at least a portion of the lumen-containing device. Similarly, the housing 110 includes an outlet port 114 that can be at least temporarily coupled to a medical device such as, for example, a sample reservoir containing a culture medium, a Vacutainer™, a cartridge configured for insertion into a diagnostic analysis machine (e.g., a PCR diagnostic machine, a DNA diagnostic machine, etc.) or the like. As described in further detail herein, a user can manipulate the device 100 to withdraw a volume of bodily-fluid from a patient via the inlet port 113 of the housing 110 and subsequently can manipulate the device 100 to expel at least a portion of the volume of bodily-fluid into a sampling device or reservoir via the outlet port 114 defined by the housing 110.

As shown in FIG. 1, the housing 110 defines an inner volume 115 that is configured to receive a portion of the actuator mechanism 120. More specifically, the actuator mechanism 120 is at least partially disposed within the inner volume 115 of the housing 110 and is movable between a first position and a second position relative to the housing 110. Moreover, the housing 110 is configured to define and/or house at least a portion of the first reservoir 160 and at least a portion of the second reservoir 170. For example, in some embodiments, the first reservoir 160 can be defined by the actuator mechanism 120 and disposed within the housing 110, and the second reservoir 170 can be collectively defined by a portion of the housing 110 and a portion of the actuator mechanism 120 disposed within the inner volume 115. In other embodiments, the first reservoir 160 and/or the second reservoir 170 can be any suitable configuration, which can be placed in fluid communication with the inlet port 113 of the housing 110, for example, via at least a portion of the inner volume 115.

The actuator mechanism 120 can be any suitable shape, size, or configuration. For example, in some embodiments, the shape and size of at least a portion of the actuator mechanism 120 substantially corresponds to the shape and size of a portion of the housing 110 defining the inner volume 115. As described above, at least a portion of the actuator mechanism 120 is movably disposed within the inner volume 115 of the housing 110. For example, a distal end portion of the actuator mechanism 120 can be disposed within the inner volume 115 of the housing 110, while a proximal end portion of the actuator mechanism 120 is disposed substantially outside the housing 110. In this manner, a user can engage the proximal end portion of the actuator mechanism 120 to move the portion of the actuator mechanism 120 within the inner volume 115 between the first position and the second position relative to the housing 110. In some embodiments, the actuator mechanism 120 can be disposed in a third position (or storage configuration) relative to the housing 110, as further described herein.

While not shown in FIG. 1, in some embodiments, the actuator mechanism 120 can include a first member and a second member. In such embodiments, both the first member and the second member can be collectively moved within the inner volume 115 of the housing 110 to move the actuator mechanism 120 between the first position and the second position. In addition, the first member and the second member can be configured to move independently within the housing 110. For example, in some embodiments, the second member can be at least partially disposed in the first member and movable in an axial direction (e.g., proximal and/or distal direction) to transition the actuator mechanism 120 between a first configuration and a second configuration. In some embodiments, the first member and/or the second member can form and/or can include a piston or plunger configured to move within the inner volume 115. As such, a portion of the piston or plunger can form a substantially fluid tight seal with the walls of the housing 110 defining the inner volume 115. In this manner, the housing 110 and the actuator mechanism 120 can collectively form a substantially sealed, airtight cavity such that movement of the actuator mechanism 120 (or at least a portion of the actuator mechanism 120) introduces or otherwise facilitates the development of a vacuum within the inner volume 115. The vacuum can be created via a plurality of mechanisms including but not limited to manual user intervention, negative pressure created in manufacturing process, springs, coils or the like. In this manner, the device 100 can be arranged as a syringe or the like, as described in further detail herein.

The first reservoir 160 can be any suitable reservoir for containing the bodily-fluid. For example, in some embodiments, the first reservoir 160 is defined by a portion of the walls of the housing 110 defining the inner volume 115 and a portion of the actuator mechanism 120. In other embodiments, the first reservoir 160 is defined by only the actuator mechanism 120. For example, when the actuator mechanism 120 includes a first member and a second member, movement of the second member relative to the first member can be such that the first member and the second member collectively define the first reservoir 160. In still other embodiments, the first reservoir 160 can be a pre-sample reservoir described in detail in U.S. Pat. No. 8,197,420 entitled, "Systems and Methods for Parenterally Procuring Bodily-Fluid Samples with Reduced Contamination," filed Dec. 13, 2007, the disclosure of which is incorporated herein by reference in its entirety. In some embodiments, the first reservoir 160 can be any number of pre-sample reservoirs or a set of fluid reservoirs (e.g., more than one reservoir). Moreover, the first reservoir 160 can be selectively placed in fluid communication with the housing 110 or the actuator mechanism 120 either directly (e.g., physically and fluidically coupled to the housing 110 or the actuator mechanism 120) or indirectly (e.g., fluidically coupled via intervening structure such as sterile flexible tubing).

The first reservoir 160 is configured to receive and contain the first, predetermined amount of the bodily-fluid. That is to say, the first reservoir 160 can define any suitable volume configured to receive and contain the first, predetermined amount of the bodily-fluid. For example, in some embodiments, the first reservoir 160 can be a nanovial or microvial configured to receive one drop of bodily-fluid up to a few drops of bodily fluid. In other embodiments, the first reservoir 160 can be a container, reservoir, microvial, via, etc. configured to receive, for example, 0.01 mL, 0.05 mL, about 0.1 mL, about 0.5 mL, about 1.0 mL, about 2.0 mL, about 3.0 mL, about 4.0 mL, about 5.0 mL, about 6.0 mL, about 7.0 mL, about 8.0 mL, about 9.0 mL, about 10.0 mL, about 15.0 mL, about 20.0 mL or more.

In some embodiments, when the actuator mechanism 120 is in the first configuration, a portion of the actuator mechanism 120 and a portion of the housing 110 can define a first fluid flow path configured to fluidically couple the inlet port 113 of the housing 110 to the first reservoir 160. In some embodiments, the actuator mechanism 120 can be moved to the first configuration (e.g., from the third configuration described above) and can introduce a vacuum that facilitates the flow of the bodily-fluid through the first flow path and into the first reservoir 160. In some embodiments, the actuator mechanism 120 can include a one-way valve or the like, which can be transitioned from a closed configuration to an open configuration in response to the vacuum, thereby placing the first reservoir 160 in fluid communication with the inlet port 113. The first reservoir 160 is configured to contain the first amount of the bodily-fluid such that the first amount is fluidically isolated from a subsequently drawn, second amount of the bodily-fluid (different from the first amount of bodily-fluid).

The second reservoir 170 can be any suitable reservoir and is configured to receive and contain, at least temporarily, the second amount of the bodily-fluid. In some embodiments, the second reservoir 170 is defined by a portion of the walls of the housing 110 defining the inner volume 115 and a portion of the actuator member 120. In this manner, when the actuator mechanism 120 is moved from the first position (e.g., a distal position) to the second position (e.g., a proximal position), a portion of the actuator mechanism 120 and a portion of the housing 110 can define a second fluid flow path configured to fluidically couple the inlet port 113 to the second reservoir 170. In some embodiments, the movement of the actuator mechanism 120 to the second position can introduce a second vacuum force, which facilitates the flow of the bodily-fluid through the second flow path and into the second reservoir 170. The second amount of bodily-fluid can be an amount withdrawn from the patient subsequent to withdrawal of the first amount. In some embodiments, the second reservoir 170 is configured to contain the second amount of the bodily-fluid such that the second amount is fluidically isolated from the first amount of the bodily-fluid. Moreover, in some instances, the second reservoir 170 is configured to temporarily contain the second amount of the bodily-fluid. For example, once the second amount of bodily-fluid is disposed in the second reservoir 170, a user can manipulate the device 100 (e.g., the actuator mechanism 120) to expel at least a portion of the second amount of bodily-fluid through the outlet port 114 and into, for example, a sample reservoir and sampling device. In some embodiments, the second amount of bodily-fluid can be any suitable volume of bodily-fluid from, for example, one or a few drops of bodily-fluid (e.g., nanoliters or microliters) to 10 mL, 20 mL, 30 mL, 40 mL, 50 mL, 100 mL, 1,000 mL, 10,000 mL, or more (or any value or fraction of a value therebetween) of bodily-fluid.

As described above, the transfer device 100 can be used to transfer a bodily-fluid from a patient to the first reservoir 160 and/or second reservoir 170 included in the transfer device 100. In addition, the transfer device 100 can be used to transfer at least a portion of a volume of bodily-fluid disposed in the second reservoir 170 into a sample reservoir and/or sampling device via the outlet port 114. In some embodiments, a user can, for example, couple the inlet port 113 to a lumen-defining device and/or the like that defines the fluid pathway P between the patient and the inlet port 113. The user can then manipulate the actuator member 120 to begin a flow of the bodily-fluid into, for example, the first fluid reservoir 160. For example, in some embodiments, the user can manipulate the actuator mechanism 120 such that a second member of the actuator mechanism 120 is moved relative to a first member, thereby defining the first reservoir 160 and introducing a vacuum therein that is operable in drawing the flow of the first amount of bodily-fluid into the first reservoir 160. In some instances, the flow of the first amount of bodily-fluid transferred to the first reservoir 160 can include dermally-residing microbes dislodged during a venipuncture event and/or other external sources (e.g. ambient airborne microbes, transferred from the skin of the practitioner collecting the sample, etc.), which become entrained in the flow and are thereby transferred to the first reservoir 160.

The first amount of bodily-fluid can then be 160 fluidically isolated in the first reservoir 160 such that when the subsequent second amount is withdrawn into the second reservoir 170, the second amount is substantially free from the dermally-residing microbes or other undesirable external contaminants as described above. More specifically, with the first amount of bodily-fluid fluidically isolated in the first reservoir 160, a user can manipulate the actuator mechanism 120 by moving the actuator mechanism 120 from the first position (e.g., a distal position) to the second position (e.g., a proximal position) within the housing 110. In this manner, the movement of the actuator mechanism 120 within the inner volume 115 can define the second reservoir 170 and can introduce a vacuum therein, which in turn, is operable in drawing the flow of the second amount of bodily-fluid into the second reservoir 170. With a desired amount of bodily-fluid disposed in the second reservoir 170 (e.g., the second amount of the bodily-fluid), a user can manipulate the device 100 by coupling a sampling device and/or reservoir to the outlet port 114 if not already coupled thereto. The user can manipulate the actuator mechanism 120 by moving the actuator mechanism 120 from the second position toward the first position (e.g., in a distal position). In this manner, at least a portion of the second amount of bodily-fluid can be expelled from the outlet port 114 and into, for example, the sampling device and/or reservoir coupled thereto. Therefore, when the actuator mechanism 120 is moved toward the first position, the transfer device 100 can transfer a portion of the second amount of the bodily-fluid from the second reservoir 170 to any suitable container (e.g., a vile, a test tube, a petri dish, a culture medium, a test apparatus, or the like) such that the portion of the second amount of bodily-fluid can be tested. Moreover, in some instances, once a desired amount of the bodily-fluid is transferred into the desired container, the user can replace the container having the desired fill volume with an empty container (e.g., can decouple the filled container and couple a different, unused container). Once coupled, the user can manipulate the transfer device 100 to transfer a desired volume of bodily-fluid from the transfer device 100 into, for example, the unused container (e.g., a second container).

Although described above as being coupled to one or more external fluid reservoirs, containers, and/or devices, in other embodiments, the transfer device 100 can include and/or can pre-assembled with such an external reservoir(s), etc. In such embodiments, the preassembled and/or all-in-one syringe-based transfer device can include, for example, any suitable number of external fluid reservoirs (e.g., one fluid reservoir, two fluid reservoirs, three fluid reservoirs, four fluid reservoirs, or more) that can be preassembled and/or unitarily formed with and/or incorporated in (e.g., during manufacturing) the transfer device. For example, the transfer device 100 can be preassembled and/or unitarily formed with any suitable reservoir as described in, for example, U.S. Patent Publication No. 2015/0342510 entitled, "Sterile Bodily-Fluid Collection Device and Methods," filed Jun. 2, 2015, the disclosure of which is incorporated herein by reference in its entirety.

In some embodiments, the transfer device 100 can be configured such that the first amount of bodily-fluid need be conveyed to the first reservoir 160 before the transfer device 100 will permit the flow of the second amount of bodily-fluid to be conveyed through the second flow path to the second reservoir 160. In this manner, the transfer device 100 can be characterized as requiring compliance by a health care practitioner regarding the collection of the first, predetermined amount (e.g., a pre-sample) prior to collection of the second amount (e.g., a sample) of bodily-fluid. Similarly stated, the transfer device 100 can be configured to prevent a health care practitioner from collecting the second amount, or the sample, of bodily-fluid into the second reservoir 170 without first diverting the first amount, or pre-sample, of bodily-fluid into the first reservoir 160. In this manner, the health care practitioner is prevented from including (whether intentionally or unintentionally) the first amount of bodily-fluid, which is more likely to contain dermally-residing microbes and/or other external undesirable contaminants, in the bodily-fluid sample to be used for analysis. In other embodiments, the fluid transfer device 100 need not include a forced-compliance feature or component.

FIGS. 2-7 illustrate a syringe-based transfer device 200 according to an embodiment. The syringe-based transfer device 200 (also referred to herein as "bodily-fluid transfer device," "fluid transfer device," or "transfer device") includes a housing 210 and an actuator mechanism 220. Furthermore, the transfer device 200 is configured to include or define a first fluid reservoir 260 (also referred to herein as "first reservoir" or "pre-sample reservoir") and a second fluid reservoir 270 (also referred to herein as "second reservoir" or "sample reservoir"). The transfer device 200 can be any suitable shape, size, or configuration. For example, while shown in FIGS. 2 and 3 as being substantially cylindrical, the transfer device 200 can be square, rectangular, polygonal, and/or any other non-cylindrical shape.

Figure 2:
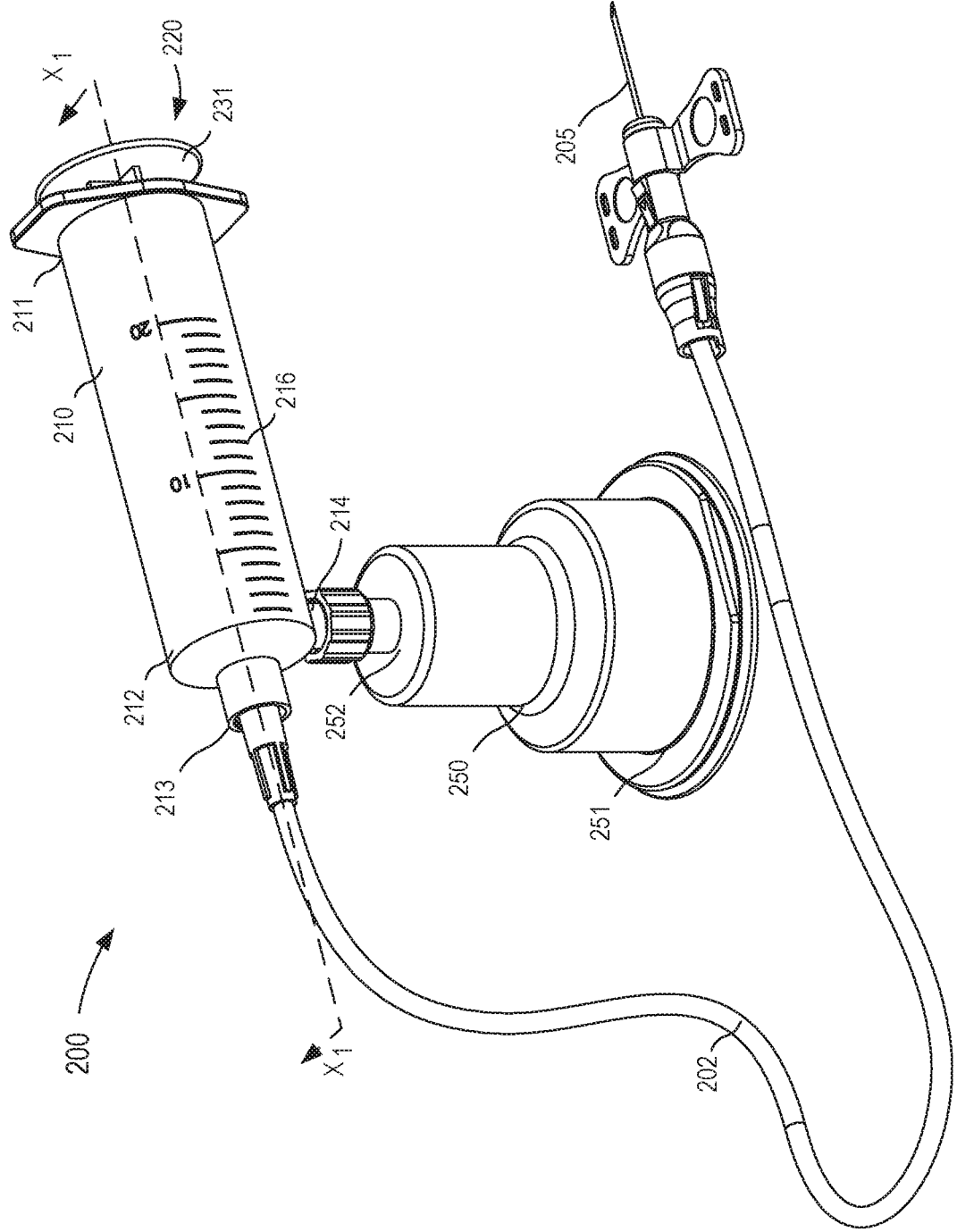
FIG. 2 is a perspective view of a syringe-based transfer device according to an embodiment.
Figure 3:
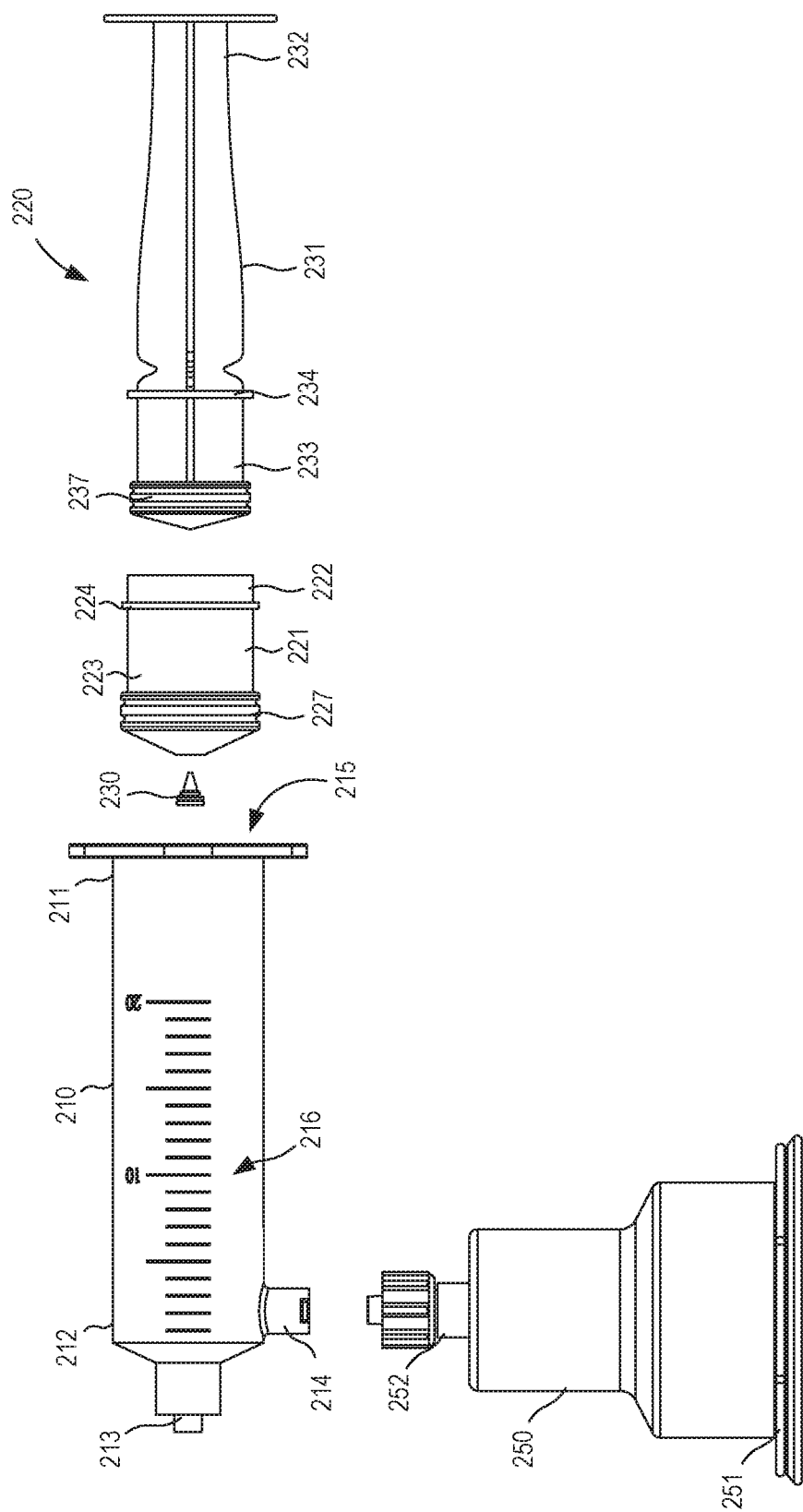
FIG. 3 is an exploded view of the syringe-based transfer device of FIG. 2.

As shown in FIGS. 2 and 3, the housing 210 includes a proximal end portion 211 and a distal end portion 212 and defines an inner volume 215 therebetween. In addition, the housing 210 includes an indicator portion 216. The indicator portion 216 can be any suitable arrangement configured to provide a visual indication associated with a volume of fluid disposed within the housing 210. For example, in some embodiments, the indicator portion 216 can be indicia such as, for example, a substantially uniform gradation of tick marks, lines, markings, and/or other suitable indicators that correspond to a position along the housing 210 that is associated with a given volume within the inner volume 215. Moreover, the housing 210 can be at least partially transparent to allow for a visualization of the inner volume 215. Thus, when a fluid is disposed within the inner volume 215, the indicator portion 216 can provide the user with a visual indication associated with a volume of the fluid disposed in the inner volume 215.

In other embodiments, the housing 210 does not include an indicator portion 216 and/or is not transparent. That is to say, in some embodiments, a housing does not provide a visual indication associated with a volume of fluid disposed therein. In such embodiments, a transfer device can include any suitable feature, component, mechanism, and/or the like configured to actuate and/or otherwise manipulate the transfer device to transfer a volume (e.g., a predetermined volume or a variable volume) of bodily-fluid into the housing. For example, a transfer device can be configured to define a negative pressure and/or can include a spring, a coil, and/or any other suitable mechanism configured to actuate at least a portion of the transfer device such that a desired amount of bodily-fluid is transferred to the transfer device.

In some embodiments, the housing 210 can be substantially similar to a syringe body. The proximal end portion 211 of the housing 210 is substantially open and movably receives at least a portion of the actuator mechanism 220. In other words, the portion of the actuator mechanism 220 is movably disposed within the inner volume 215. Furthermore, when the actuator mechanism 220 is disposed in the inner volume 215, an inner surface of the housing 210 that defines the inner volume and a surface of the actuator mechanism 220 collectively define at least a portion of the second fluid reservoir 270, as further described herein. The distal end portion 212 of the housing 210 includes an inlet port 213 and an outlet port 214, which are each selectively in fluid communication with the inner volume 215. The inlet port 213 and the outlet port 214 can be any suitable shape, size, or configuration. In some embodiments, the inlet port 213 and/or the outlet portion 214 can be monolithically formed with the housing 210 (e.g., as shown in FIGS. 2-7). In other embodiments, the inlet port 213 and/or outlet port 214 can be coupled to the distal end portion 212 in any suitable manner such as, for example, via a friction fit, a threaded coupling, a mechanical fastener, an adhesive (e.g. glue, bond, ultrasonic weld, and/or the like), any number of mating recesses, and/or any combination thereof. In some embodiments, at least a portion of the inlet port 213 can form a lock mechanism, which in turn, can physically and fluidically couple to a needle, a cannula, or other lumen-containing device (not shown in FIGS. 2-7).

By way of example, the inlet port 213 can be a Luer-Lok® or similar locking mechanism. In such embodiments, the inlet port 213 can include a valve or the like that can be transitioned between a closed configuration, in which the inner volume 215 of the housing 210 is fluidically isolated from at least a portion of the inlet port 213, to an open configuration, in which the inner volume 215 is in fluid communication with the inlet port 213. Such a valve can transition from the closed configuration to the open configuration, for example, in response to a negative pressure produced within the inner volume 215 (whether by user actuation or mechanically generated force), as described in further detail herein. In this manner, the inlet port 213 can be physically and fluidically coupled to a lumen-defining device at least partially disposed within a patient to define a portion of a fluid flow path between the patient and the inner volume 215, as further described herein.

The outlet port 214 can be substantially similar to the inlet port 213 and configured to selectively place the inner volume 215 in fluid communication with a sampling device and/or reservoir. In some embodiments, the outlet port 214 can include a valve or the like configured to transition from a closed configuration to an open configuration in response to an increase in pressure within the inner volume 215 (i.e., operate substantially opposite to the valve in the inlet port 213). As shown in FIGS. 2 and 3, the outlet port 214 can be physically and fluidically coupled to a portion of an adapter 250.

The adapter 250 can be any suitable shape, size, or configuration. As shown in FIG. 3, the adapter 250 includes a proximal end portion 251, a distal end portion 252, and a puncture member 253. The distal end portion 252 can include any suitable coupling mechanism, locking mechanism, and/or the like configured to physically and fluidically couple the adapter 250 to the outlet port 214 of the housing 210. For example, in some embodiments, the outlet port 214 can be a male Luer-Lok® and the distal end portion 252 of the adapter 250 can include and/or can form a corresponding female Luer-Lok®. The proximal end portion 251 is open and is configured to receive a portion of a sampling reservoir such as, for example, an ampoule, a vial, an evacuated container (e.g., a Vacutainer™), and/or the like. For example, in some embodiments, an evacuated container (not shown in FIGS. 2-7) can be inserted into the adapter 250 and positioned such that the puncture member 253 of the adapter 250 punctures and/or pierces a septum of the evacuated container. As such, the puncture member 253 (e.g., a needle), the distal end portion 252 of the adapter 250, and the outlet portion 214 of the housing 210 can collectively define a fluid flow path between the inner volume 215 of the housing 210 and an inner volume of the evacuated container (see e.g., FIG. 4), as described in further detail herein.

The actuator mechanism 220 of the device 200 is at least partially disposed within the inner volume 215 and is movable between a first position (e.g., a distal position relative to the housing 210) and a second position (e.g., a proximal position relative to the housing 210). The movement of the actuator mechanism 220 relative to the housing 210 can transition the device 200 between a first, a second, a third, and a fourth configuration as further described herein. As shown in FIG. 3, the actuator mechanism 220 includes a first member 221 and a second member 231. The first member 221 of the actuator mechanism 220 includes a proximal end portion 222 and a distal end portion 223 and defines an inner volume 226 therebetween. At least a portion of the inner volume 226 is configured to define the first reservoir 260, as further described herein.

The proximal end portion 222 of the first member 221 is open and configured to receive at least a portion of the second member 231 therethrough. The proximal end portion 222 also includes a protrusion 224 that extends from an outer surface of the first member 221 (e.g., an at least partially circumferential protrusion) configured to selectively engage the proximal end portion 211 of the housing 210 to limit a proximal movement of the first member 221, as described in further detail herein.

The distal end portion 223 of the first member 221 includes a plunger 227. The plunger 227 is configured to form a friction fit with the inner surface of the housing 210 that defines the inner volume 215 when the actuator mechanism 220 is disposed within the housing 210. Similarly stated, the plunger 227 defines a fluidic seal with the inner surface of the housing 210 that defines the inner volume 215 such that a portion of the inner volume 215 proximal to the plunger 227 is fluidically isolated from a portion of the inner volume 215 distal to the plunger 227.

Figure 4:
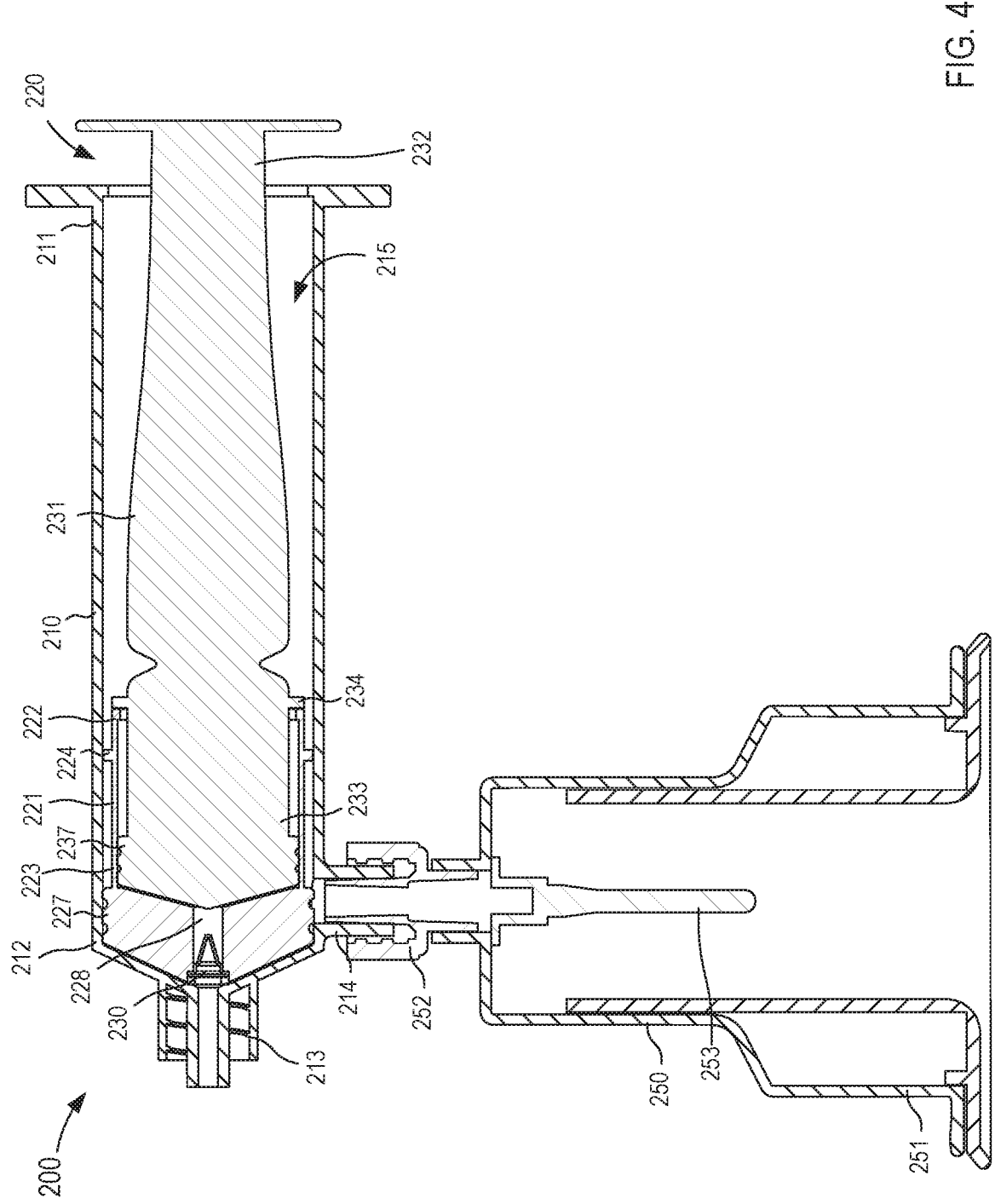
FIGS. 4-7 are cross-sectional views of the syringe-based transfer device illustrated in FIG. 2 taken along the line $X_1$-$X_1$, in the first configuration, a second configuration, a third configuration, and a fourth configuration, respectively.
Figure 5:
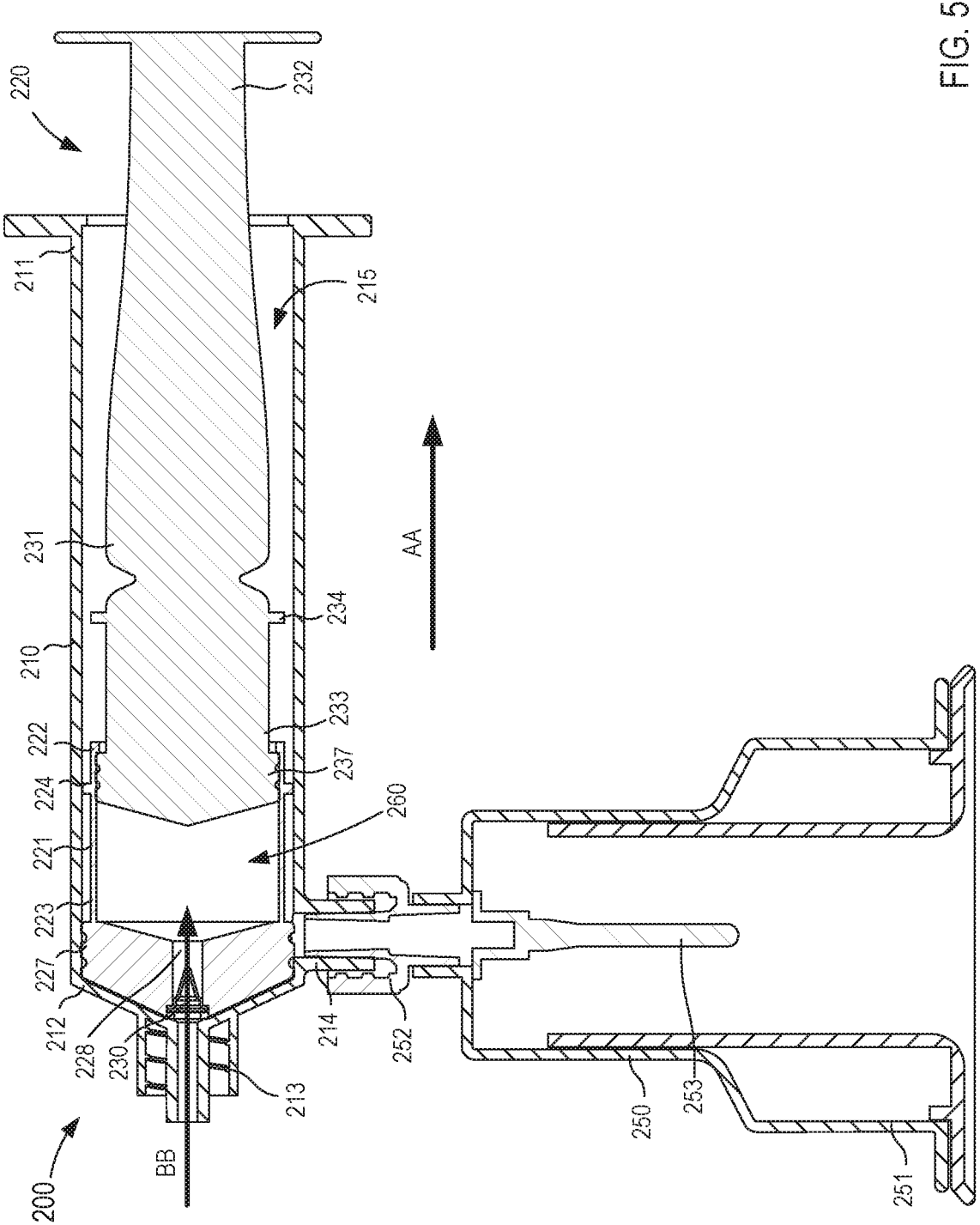
Figure 6:
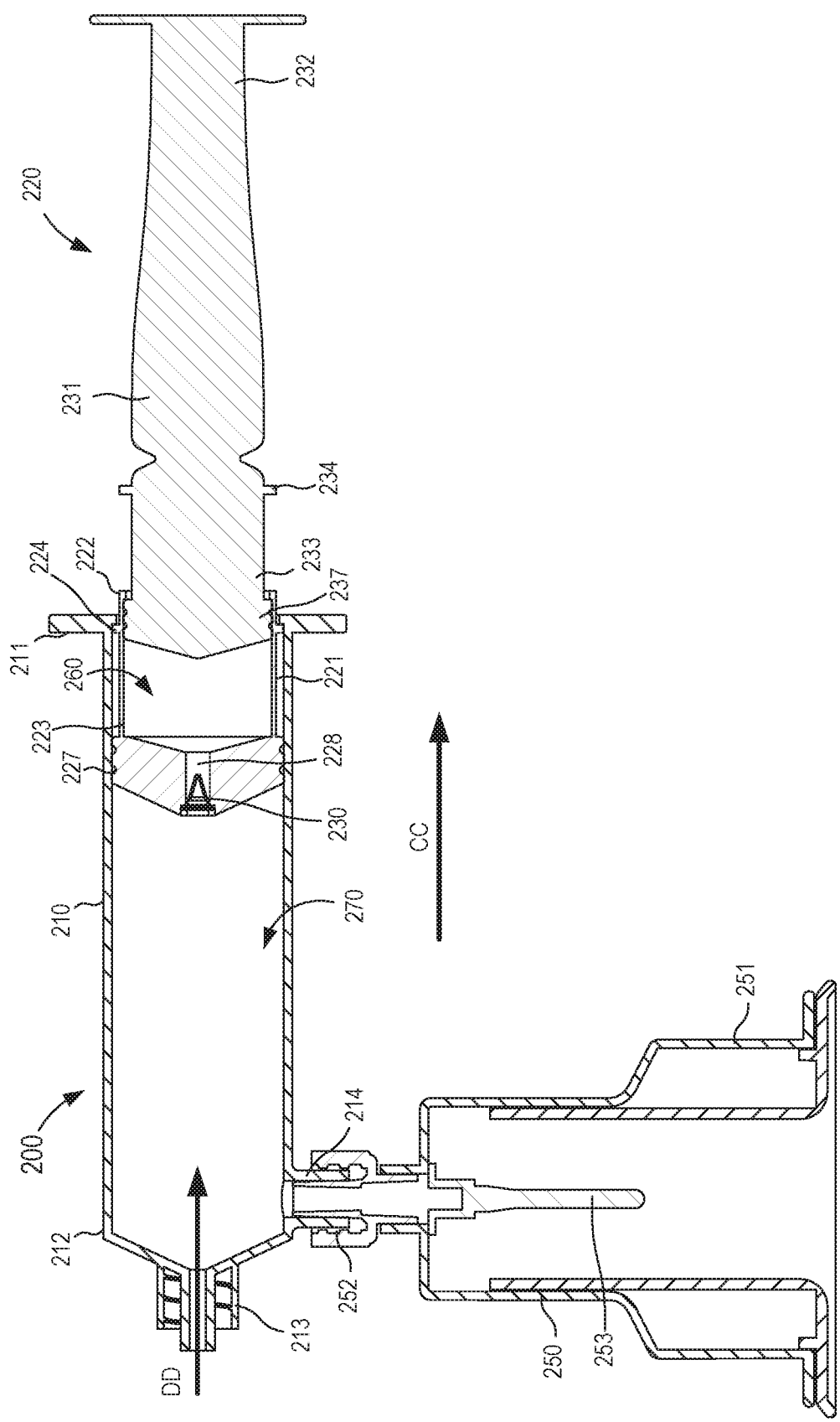

As shown in FIG. 4, the plunger 227 defines a channel 228 that extends through the plunger 227 (e.g., through a distal end and a proximal end of the plunger 227). In some embodiments, the channel 228 can receive a valve 230, which can be fixedly disposed therein by a friction fit, a snap fit, a treaded coupling, glue, bond, weld, and/or the like. As such, the valve 230 can form a substantially fluid tight seal with surface of the plunger 227 that defines at least a portion of the channel 228. The valve 230 can be any suitable valve (e.g., check valve, ball valve, float valve, etc.). Specifically, in this embodiment, the valve 230 is a one-way check valve configured to allow a flow of a fluid from a distal end of the valve 230 to a proximal end of the valve 230 but substantially not allow a flow of the fluid from the proximal end to the distal end. In this manner, when the valve 230 is in the open configuration, the inner volume 226 defined by the first member 221 is placed in fluid communication with the portion of the inner volume 215 of the housing 210 that is distal to the plunger 227, and when the valve is in the closed configuration, the inner volume 226 of the first member 221 is fluidically isolated from the portion of the inner volume 215 that is distal to the plunger 227. Although described above as the valve 230, in other embodiments, a transfer device can include any suitable means for selectively allowing a flow of fluid. For example, in some embodiments, a transfer device can include a diaphragm, membrane, tubing, and/or the like.

The second member 231 of the actuator mechanism 220 includes a proximal end portion 232 and a distal end portion 233. In some embodiments, the proximal end portion 222 can have a size and/or shape configured to facilitate a user's engagement thereof. For example, the proximal end portion 222 can include a flange, a tab, and/or the like that can be engaged by a user (e.g., a phlebotomist, a nurse, a technician, a physician, etc.) to move the first member 221 relative to the housing 210, as described in further detail herein. The distal end portion 233 includes a plunger 237 configured to form a friction fit with the inner surface of the first member 221 defining the inner volume 226 when the second member 231 is disposed therein. Similarly stated, the plunger 237 defines a fluidic seal with the inner surface first member 221 that defines the inner volume 226 such that a portion of the inner volume 226 proximal to the plunger 237 is fluidically isolated from a portion of the inner volume 226 distal to the plunger 237.

As described above, at least a portion the second member 231 is configured to be movably disposed within the inner volume 226 of the first member 221. More specifically, the second member 231 can be movable between a first position (e.g., a distal position) and a second position (e.g., a proximal position) thereby transitioning the actuator mechanism 220 between a first configuration and a second configuration, respectively. In addition, the second member 231 includes a protrusion 234 that extends in a radial direction to selectively engage a proximal surface of the first member 221. In this manner, the protrusion 224 of the first member 221 can be placed in contact with the proximal surface of the first member 221 to substantially limit a distal movement of the second member 231 relative the first member 221, as described in further detail herein.

In use, a user can engage the transfer device 200 to couple the inlet port 213 to a proximal end portion of a lumen-defining device (not shown) such as, for example, a butterfly needle, a cannula assembly, a trocar (which is some cases is used to insert a catheter into a patient), or the like. The distal end portion of the lumen-defining device can be disposed within a portion of the body of a patient (e.g., a vein). In this manner, the inlet port 213 is placed in fluid communication with the portion of the body. With the inlet port 213 coupled to the lumen-defining device, a user (e.g., a phlebotomist, a nurse, a technician, a physician, or the like) can transition the transfer device 200 from the first configuration (see e.g., FIG. 4) to the second configuration (see e.g., FIG. 5). More specifically, the user can engage the proximal end portion 232 of the second member 231 to move the second member 231 in the proximal direction relative to the first member 221 from its first position (e.g., a distal position) to its second configuration (e.g., a proximal position), thereby placing the transfer device 200 in the second configuration, as indicated by the arrow AA in FIG. 5. In some instances, the second member 231 of the actuator mechanism 220 is moved in a proximal direction relative to the first member 221 (e.g., the first member 221 does not substantially move in the proximal direction) until a proximal surface of the plunger 237 of the second member 231 is placed in contact with the proximal end portion 222 of the first member 221 (e.g., a tab or flange extending into the inner volume 226).

The arrangement of the second member 231 within the first member 221 is such that the proximal motion of the second member 231 increases the volume of the portion of the inner volume 226 that is distal to the plunger 237, thereby defining the first reservoir 260. Furthermore, with the plunger 237 forming a fluid tight seal with the inner surface of the walls defining the inner volume 226, the increase of volume can produce a negative pressure within the first reservoir 260, which can be sufficient to transition the valve 230 from a closed configuration to an open configuration. Thus, the inlet port 213, the valve 230, and the channel 228 define a fluid flow path that places the first reservoir 260 in fluid communication with the lumen-defining device and more particularly, the portion of the patient (e.g., the vein), as indicated by the arrow BB in FIG. 5. In other words, the negative pressure within the within the first reservoir 260 produced by the movement of the plunger 237 of the second member 231 within the inner volume 226 defined by the first member 221 introduces a suction force within the portion of the patient. As such, a volume of bodily-fluid is drawn through the inlet port 213 and the valve 230 and into the first reservoir 260. In some embodiments, the bodily-fluid can contain undesirable microbes such as, for example, dermally-residing microbes and/or other external contaminants (e.g., microbes within a lumen defined by the transfer device 200, microbes within the lumen defined by the lumen defining device, and/or any other undesirable microbe not present in the bodily-fluid source such as the bloodstream).

In some embodiments, the magnitude of the suction force can be modulated by increasing or decreasing the amount of a force applied to the actuation mechanism 220. For example, in some embodiments, it can be desirable to limit the amount of suction force introduced to a vein. In such embodiments, the user can reduce the amount of force applied to the proximal end portion 232 of the second member 231. In this manner, the rate of change (e.g., the increase) in the volume of the first reservoir 260 can be sufficiently slow to allow time for the negative pressure differential between the vein and the fluid reservoir to come to equilibrium before further increasing the volume of the first reservoir 260. Thus, the magnitude of the suction force can be modulated.

While in the second configuration (see e.g., FIG. 5), the transfer device 200 can be configured to transfer a desired amount (e.g., a predetermined amount) of bodily-fluid transferred to the first reservoir 260. In some embodiments, the first, predetermined amount can substantially correspond to the size of the first reservoir 260. In other embodiments, the first amount can substantially correspond to an equalization of pressure within the first reservoir 260 and the portion of the patient. Moreover, in such embodiments, the equalization of the pressure can be such that the valve 230 is allowed to return to the closed configuration. Thus, the first reservoir 260 is fluidically isolated from a volume substantially outside the first reservoir 260.

With the first amount fluidically isolated, the device 200 can be transitioned from the second configuration (FIG. 5) to the third configuration (FIG. 6) by further moving the actuator mechanism 220 in the proximal direction. For example, as indicated by the arrow CC in FIG. 6, the user can apply a force to the proximal end portion 232 of the second member 231 to move the actuator mechanism 220 relative to the housing 210. Expanding further, with the plunger 237 in contact with the proximal end portion 222 of the first member 221, the further application of force on the proximal end portion 232 of the second member 231 collectively moves the first member 221 and the second member 231 in the proximal direction relative to the housing 210.

The arrangement of the first member 221 within the inner volume 215 of the housing 210 is such that the proximal motion of the first member 221 increases the volume of the portion of the inner volume 215 that is distal to the plunger 227, thereby defining the second reservoir 270. Furthermore, with the plunger 227 forming a fluid tight seal with the inner surface of the housing 210 that defines the inner volume 215 and with the valve 230 in the closed configuration, the increase of volume produce a negative pressure within the second reservoir 270. Therefore, the second reservoir 270 is placed in fluid communication with the portion of the patient (e.g., the vein), as indicated by the arrow DD in FIG. 6. Expanding further, the negative pressure within the second reservoir 270 produced by the movement of the plunger 227 introduces a suction force within the portion of the patient that is sufficient to draw a volume of bodily-fluid through the inlet port 213 and into the second reservoir 270. In addition, by fluidically isolating the first reservoir 260, the bodily-fluid contained within the second reservoir 270 is substantially free from microbes generally found outside of the portion of the patient (as described above). In some embodiments, the user can visualize and/or otherwise quantify the volume of the bodily-fluid disposed in the second reservoir 270 via the indication portion 216 of the housing 210. For example, in some instances, the volume of the bodily-fluid disposed in the second reservoir 270 substantially corresponds to a line, gradation, marker, tic mark, etc. included in the indication portion 216. Thus, the user can withdraw a bodily-fluid from the patient until a desired volume of the bodily-fluid is disposed in the second reservoir 270.

With the desired volume of bodily-fluid disposed in the second reservoir 270, the transfer device 200 can be transitioned from the third configuration to the fourth configuration. For example, in some embodiments, with the desired amount of bodily-fluid disposed within the second fluid reservoir 270, the inlet port 213 of the housing 210 can be removed from the lumen-defining device and the adapter 250 can be coupled to a sampling container (e.g., a vile, a test tube, a petri dish, a culture medium, a test apparatus, a cartridge designed for use with an automated, rapid microbial detection system, or the like (not shown)) such that at least a portion of the volume of bodily-fluid can be transferred from the second reservoir 270 to the sampling container to be tested.

Figure 7:
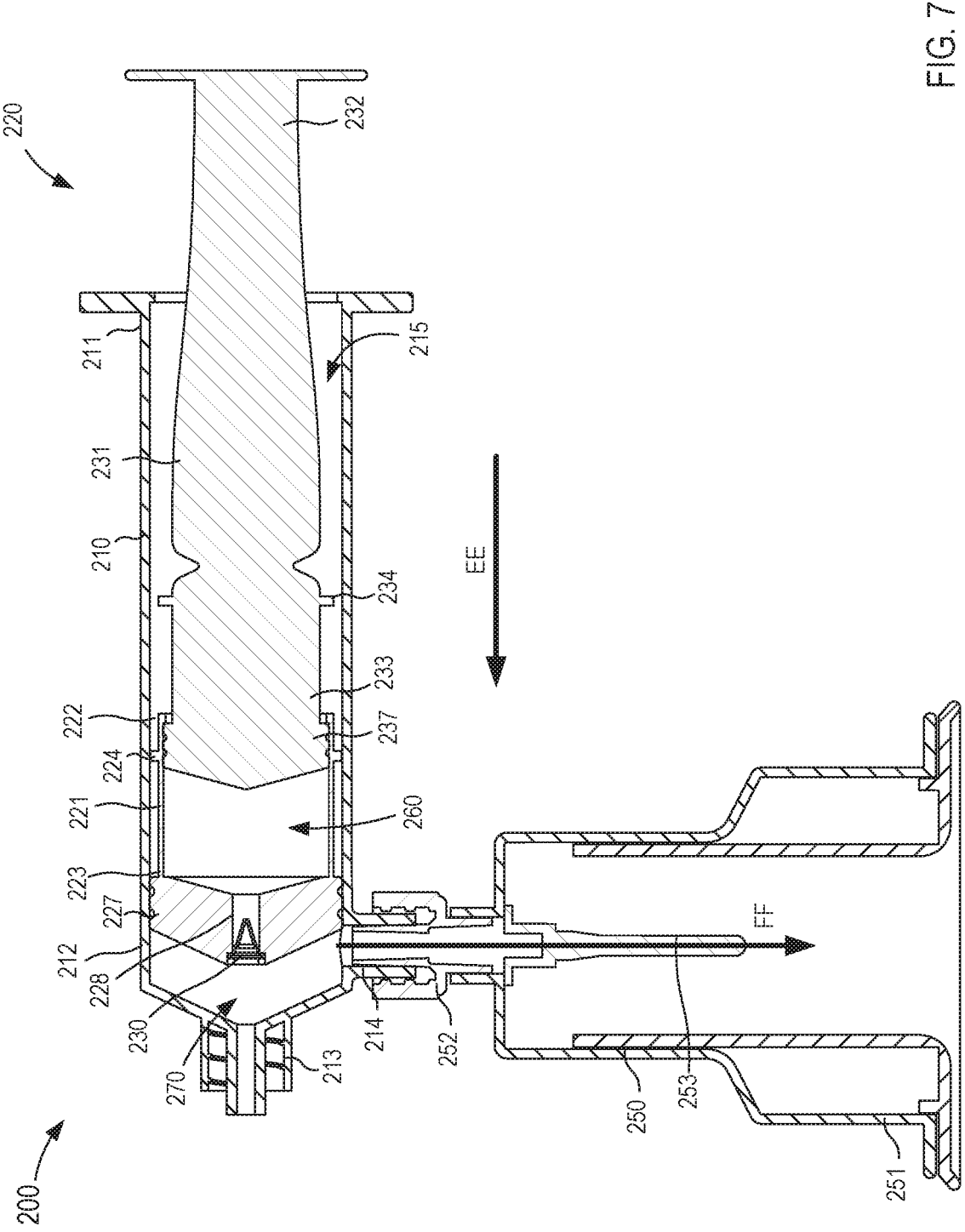

Expanding further, the user can apply a force to the proximal end portion 232 of the second member 231 to move the actuator mechanism 220 in the distal direction, as indicated by the arrow EE in FIG. 7. With the valve 230 in the closed configuration the bodily-fluid contained within the first reservoir 260 is maintained in fluid isolation with a volume outside the first reservoir 260. In some embodiments, the volume of the first reservoir 260 is sufficient to contain a drop of bodily-fluid or a few drops of bodily-fluid. In other embodiments, the volume of the first reservoir 260 is sufficient to contain the first centiliter or few centiliters of bodily-fluid. In other embodiments, the first reservoir 260 can be configured to contain from about 0.1 ml to about 3.0 ml. In still other embodiments, the first reservoir 260 can be configured to contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. Furthermore, the pressure within the first reservoir 260 can be such that the force applied to the second member 231 does not substantially move the second member 231 relative to the first member 221. Thus, the force applied to the proximal end portion 232 collectively moves the second member 231 and the first member 221 in the distal direction relative to the housing 210 to expel a desired portion of the second amount of bodily-fluid from the lumen-defining device and into the container via the outlet port 214 and adapter 250, as indicated by the arrow FF in FIG. 7. As such, the expelled bodily-fluid can be used for any number of testing processes or procedures such as, for example, blood culture testing, real-time diagnostics, and/or PCR-based approaches, while minimizing false results that might otherwise result from undesirable microbes or the like.

Although not shown in FIGS. 2-7, in some embodiments, the syringe-based transfer device 200 can be coupled to a device in fluid communication with the patient that is also configured to reduce contamination of a patient sample. For example, in some embodiments, the syringe-based transfer device 200 can be used with a device configured to selectively occlude a lumen of a needle or the like such as those described in U.S. Patent Publication No. 2014/0276578 entitled, "Methods and Apparatus for Selectively Occluding the Lumen of a Needle," filed Mar. 7, 2014 (the "'578" publication); U.S. Pat. No. 9,149,576 entitled, "Systems and Methods for Delivering a Fluid to a Patient with Reduced Contamination," filed Oct. 9, 2013 (the "'576 patent"); and/or U.S. Provisional Patent Application Ser. No. 62/250,612 entitled, "Systems and Methods for Sample Collection with Reduced Hemolysis," filed Nov. 4, 2015 (the "'612 application"), the disclosures of which are incorporated herein by reference in their entireties. In this manner, the transfer device 200 can be coupled to a device configured to selectively occlude a lumen of a needle (e.g., during insertion into the body), a device configured to selectively deliver fluid into the body (e.g., reinfuse a portion of a pre-sample or sample volume of bodily-fluid and/or infuse a volume of fluid such as a medicament or the like otherwise contained in the transfer device 200), and/or a device configured to reduce hemolysis of a blood sample withdrawn from a portion of the body by selectively controlling fluid flow and/or pressures within a portion of the device.

In some embodiments, a transfer device (e.g., the transfer device 200) can be configured to selectively occlude an inlet port and/or an outlet port during withdrawal of a bodily-fluid (e.g., occlusion of the outlet port) and/or during expulsion of the bodily-fluid (e.g., occlusion of the inlet port). By way of example, in some embodiments, a transfer device can include and/or can be coupled to a needle in fluid communication with a lumen defined by an inlet port of the transfer device. In such embodiments, the needle can be configured to retract after venipuncture and withdrawal of a desired volume of bodily-fluid into the transfer device (e.g., a second reservoir such as the second reservoir 270). The retraction of the needle can result in a portion of the needle retracting into the lumen of the inlet port, thereby occluding the lumen. In some embodiments, the needle can be operably coupled to an actuator mechanism (e.g., the actuator mechanism 220) such that a proximal movement of the actuator mechanism results in a corresponding proximal movement of the needle (i.e., retraction). In other embodiments, after withdrawing a desired amount of bodily-fluid, a needle can be removed from the patient and disposed in, for example, an external seal member or the like, which in turn, occludes a lumen of the needle and thus, a lumen of an inlet port coupled thereto. In some embodiments, a decoupling of a needle from an inlet port can be operable in transitioning a valve from an open configuration to a closed configuration (e.g., a spring loaded valve, a septum, and/or the like).

In some embodiments, an inlet port can include a valve (e.g., a one-way valve, a force balance check valve, a ball valve, and/or the like) configured to transition between a first configuration (e.g., an open configuration) to a second configuration (e.g., a closed configuration) after a desired volume of bodily-fluid is transferred to a fluid reservoir. For example, in some embodiments, coupling a sampling device and/or container (e.g., a culture bottle) to an outlet port can push, rotate, and/or otherwise transition a valve of an inlet port from a first, open configuration to a second, closed configuration. In other embodiments, the inlet port and/or the outlet port can include a flow controller such as, for example, an actuator disposed exterior to the inlet port and/or outlet port and operably coupled to the valve. In such embodiments, actuation (e.g., translation, rotation, and/or other movement) of the actuator can be operable in transitioning the valve from its open configuration to its closed configuration. By way of example, once a desired volume of bodily-fluid is transferred into a transfer device a user can rotate an actuator of an inlet port, thereby transitioning a valve of the inlet port to a closed configuration, and can rotate an actuator of an outlet port, thereby transitioning a valve of the inlet port to an open configuration. In other embodiments, an actuator can be configured to control a flow of bodily-fluid through an inlet port and/or an outlet port via a flow controller, a diverter, and/or the like.

In some embodiments, actuation of at least a portion of an actuator mechanism (e.g., translational motion, rotational motion, etc.) can transition a valve from an open configuration to a closed configuration. For example, in some such embodiments, movement of the actuator mechanism in the proximal direction beyond a position associated with the collection of about 20 milliliters (mL) of bodily-fluid can "trigger" and/or otherwise result in the valve being transitioned to a closed configuration. In other embodiments, the coupling of a sampling device to an outlet port and/or an actuation of an actuator mechanism can push, rotate, move, and/or otherwise position an occlusion member such as a gate or seal about a proximal end portion of the inlet port, thereby fluidically isolating the inlet port from a remaining inner volume (e.g., a fluid reservoir) of a transfer device. For example, a portion of an actuator mechanism can be operably coupled to a valve and/or occlusion member via a tether, rod, a rack and pinion linkage, and/or the like.

In still other embodiments, an inlet port and/or an outlet port can be transitioned between an open configuration and a closed configuration via an electromechanical device and/or mechanism such as a pressure die and battery, a solenoid, servomotor, and/or the like. By way of example, a differential pressure sensor can detect a flow of fluid through an outlet port, and in response, an electromechanical device can closes a valve of the inlet port. In some embodiments, a gauge pressure sensor can detect a drop in pressure associated with, for example, about 20 mL of bodily-fluid being disposed in the transfer device and in response, can close a valve of an inlet port. In other embodiments, an air detection sensor can sense a flow of air within the inlet port and/or outlet port and in response can open or close a valve. For example, the air detection sensor can sense an airflow at the outlet port associated with coupling an evacuated container thereto and in response, can be operable in transitioning the valve of the inlet port to a closed configuration and the valve of the outlet port to an open configuration.

In other embodiments, a valve of an inlet port and/or an outlet port can be passively transitioned in response to a change in pressure. For example, an inlet port can include a valve configured to transition to an open configuration in response to a negative pressure within a fluid reservoir and transition of a closed configuration in response to a positive pressure within the fluid reservoir. Conversely, an outlet port can include a valve configured to transition to a closed configuration in response to the negative pressure and to transition to an open configuration in response to the positive pressure. In other words, a one-way valve can have pressure threshold to allow flow of bodily-fluid therethrough. In some instances, actuating an actuator mechanism (e.g., a syringe) creates a sufficient pressure drop to overcome the threshold associated with the valve of the inlet port, thereby allowing bodily-fluid to flow therethrough. Conversely, a culture bottle, a Vacutainer™ or any other suitable sample vessel can be coupled to an outlet port and can create a pressure drop that is insufficient to overcome the threshold of associated with the valve of the inlet port while being sufficient to overcome a threshold associated with the valve of the outlet port.

Figure 8:
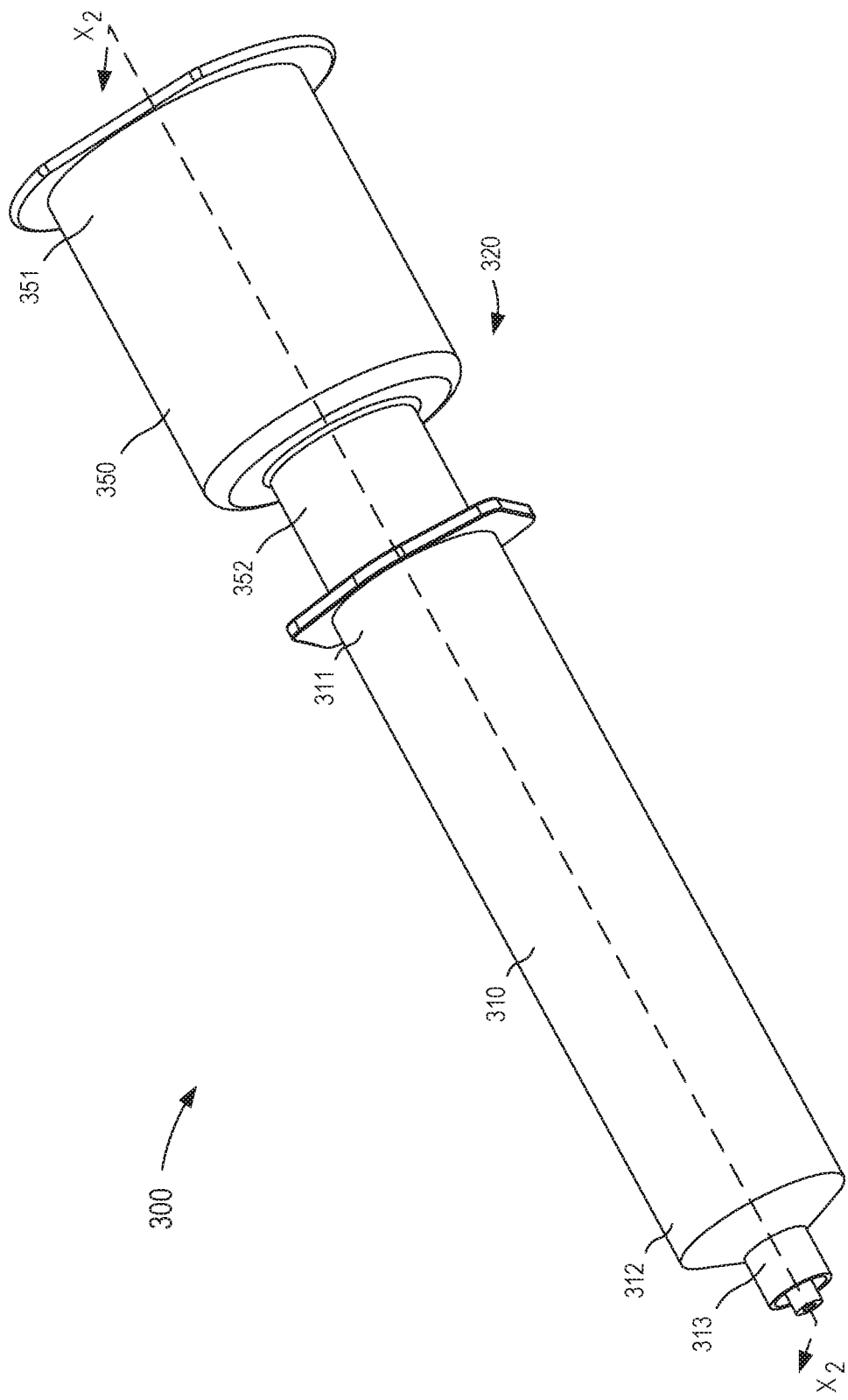
FIG. 8 is a perspective view of a syringe-based transfer device according to another embodiment.
Figure 9:
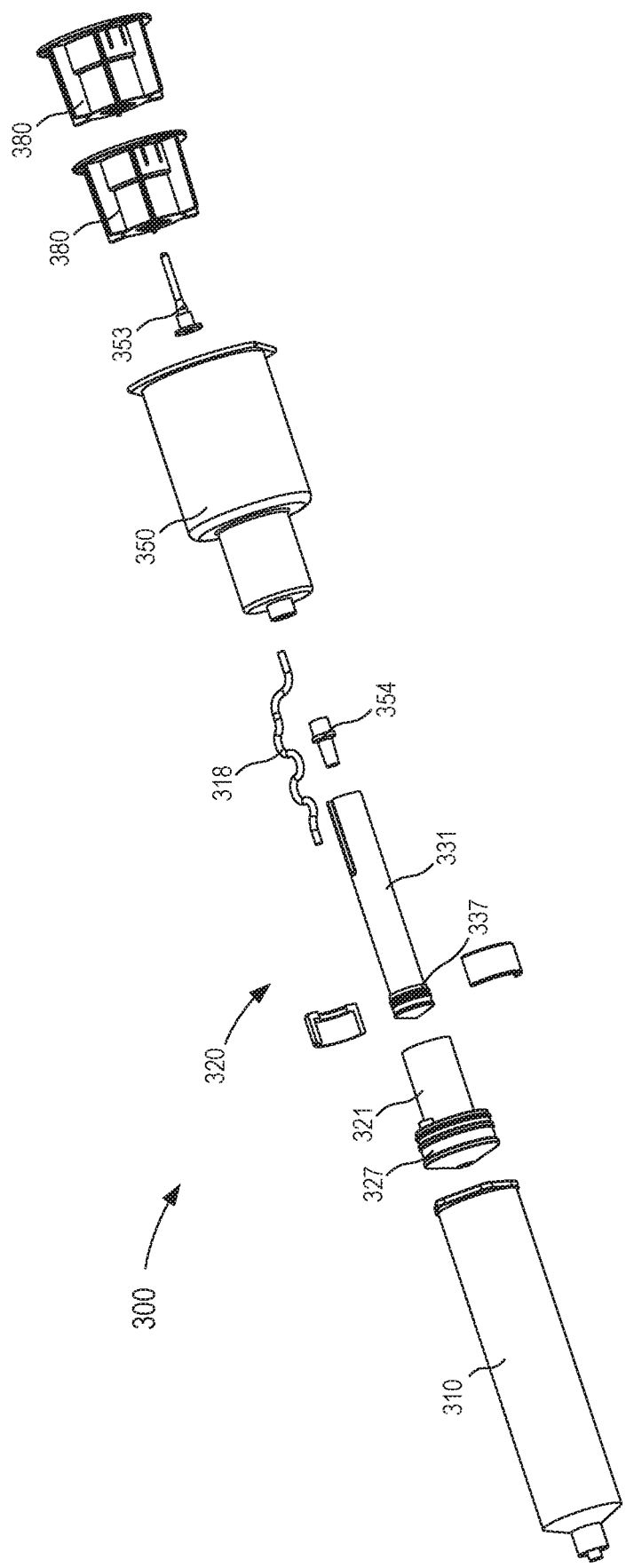
FIG. 9 is an exploded view of the syringe-based transfer device of FIG. 8.
Figure 10:
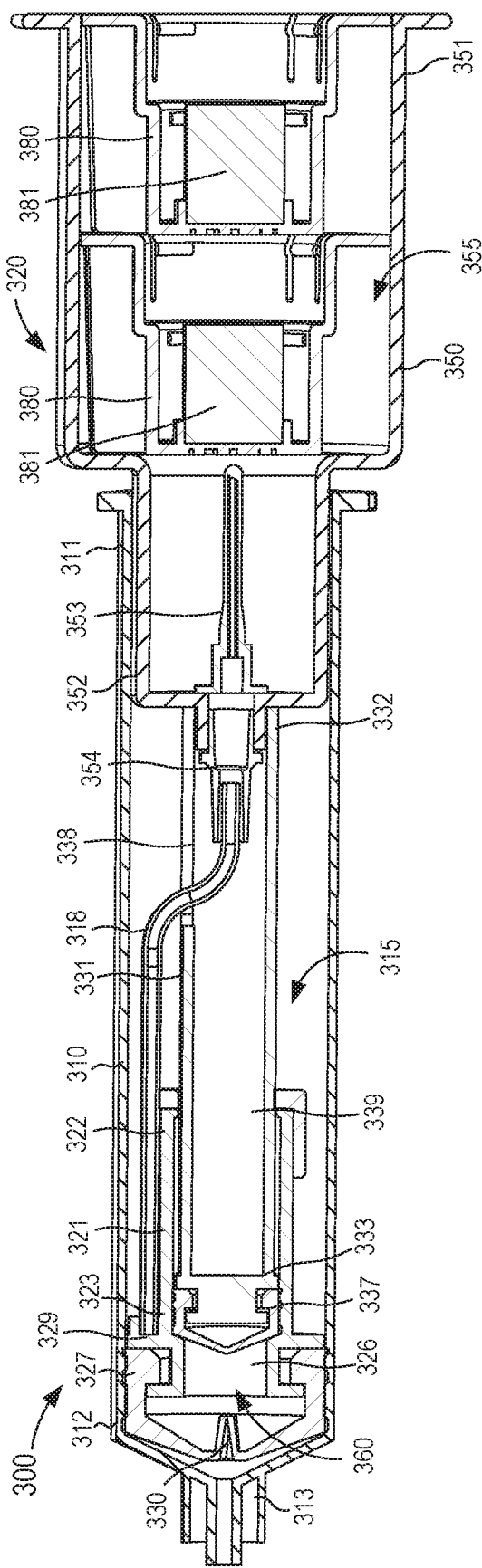
FIG. 10 is a cross-sectional view of the syringe-based transfer device illustrated in FIG. 8 taken along the like $X_2$-$X_2$.

While the transfer device 200 is particularly shown in FIGS. 2-7 as having the port 213 disposed at or near the distal end portion 212 of the housing 210, in other embodiments, a syringe-based transfer device can be arranged in any suitable configuration. For example, FIGS. 8-10 illustrate a syringe-based transfer device 300 according to another embodiment. The syringe-based transfer device 300 (also referred to herein as "transfer device") includes a housing 310, an actuator mechanism 320, an adapter 350, and one or more sterilization members 380. The transfer device 300 is also configured to include or define a first fluid reservoir 360 (also referred to herein as "first reservoir" or "pre-sample reservoir") and a second fluid reservoir 370 (also referred to herein as "second reservoir" or "sample reservoir"). The transfer device 300 can be any suitable shape, size, or configuration. For example, in some embodiments, at least a portion of the transfer device 300 can be similar in form and/or function to the transfer device 200, described above with reference to FIGS. 2-7. As such, portions of the transfer device 300 that are similar to associated portions of the transfer device 200 are not described in further detail herein.

As shown in FIGS. 8-10, the housing 310 includes a proximal end portion 311 and a distal end portion 312 and defines an inner volume 315 therebetween. The proximal end portion 311 of the housing 310 is substantially open and movably receives at least a portion of the actuator mechanism 320. As described in further detail herein, when the actuator mechanism 320 is disposed in the inner volume 315, an inner surface of the housing 310 that defines the inner volume 315 and a surface of the actuator mechanism 320 collectively define at least a portion of the second fluid reservoir 370. Moreover, as shown in FIG. 10, the inner volume 315 of the housing 310 includes and/or houses a transfer conduit 318 configured to selectively place a portion of the inner volume 315 in fluid communication with a portion of the actuator mechanism 320, as described in further detail herein.

The distal end portion 312 of the housing 310 includes an inlet port 313 that is selectively in fluid communication with the inner volume 315. The inlet port 313 can be any suitable shape, size, or configuration. For example, in some embodiments, the inlet port 313 can be substantially similar to the inlet port 213 of the transfer device 200. More specifically, in some embodiments, at least a portion of the inlet port 313 can form a lock mechanism (e.g., a Luer-Lok®, which in turn, can physically and fluidically couple to a needle, a cannula, or other lumen-containing device (not shown in FIGS. 8-10).

Although not shown in FIGS. 8-10, in some embodiments, the housing 310 can include an indicator portion or the like configured to provide a visual indication associated with a volume of fluid disposed within the housing 310. For example, in some embodiments, the housing 310 can include an indicator portion substantially similar to the indicator portion 216 included in the transfer device 200.

The actuator mechanism 320 of the transfer device 300 is at least partially disposed within the inner volume 315 and is movable between a first position (e.g., a distal position relative to the housing 310) and a second position (e.g., a proximal position relative to the housing 310). The movement of the actuator mechanism 320 relative to the housing 310 can transition the device 300 between any suitable configurations, as further described herein. As shown in FIGS. 9 and 10, the actuator mechanism 320 includes a first member 321 and a second member 331. The first member 321 of the actuator mechanism 320 includes a proximal end portion 322 and a distal end portion 323 and defines an inner volume 326 therebetween. At least a portion of the inner volume 326 is configured to define the first reservoir 360, as further described herein.

The proximal end portion 322 of the first member 321 is open and configured to receive at least a portion of the second member 331. The distal end portion 323 of the first member 321 includes a plunger 327. The plunger 327 is configured to form a friction fit with the inner surface of the housing 310 that defines the inner volume 315 when the actuator mechanism 320 is disposed within the housing 310. Similarly stated, the plunger 327 defines a fluidic seal with the inner surface of the housing 310 that defines the inner volume 315 such that a portion of the inner volume 315 proximal to the plunger 327 is fluidically isolated from a portion of the inner volume 315 distal to the plunger 327.

As shown in FIG. 10, the plunger 327 includes a port 329 and a valve 330. The valve 330 can be any suitable valve, diaphragm, membrane, and/or the like and can be fixedly coupled to the plunger 327 via a friction fit, a snap fit, a treaded coupling, glue, bond, weld, and/or the like. In some embodiments, the valve 330 can be substantially similar to the valve 230 included in the transfer device 200 and thus, is not described in further detail herein. The port 329 is configured to be coupled to and/or to receive a portion of a transfer conduit 318. Although not shown in FIG. 10, in some embodiments, the port 329 can define a channel, opening, passageway, valve, membrane, diaphragm, and/or the like configured to selectively place the transfer conduit 318 in fluid communication with a portion of the inner volume 315 that is distal to the plunger 327, as described in further detail herein.

The second member 331 of the actuator mechanism 320 includes a proximal end portion 332 and a distal end portion 333 and defines an inner volume 339. The proximal end portion 332 of the second member 331 is substantially open and is configured to be coupled to a distal end portion 352 of the adapter 350. More specifically, the distal end portion 352 of the adapter 350 includes an inlet port 354 that is disposed within the inner volume 339 of the second member 331 and that is in fluid communication with the transfer conduit 318. For example, as shown in FIG. 10, that proximal end portion 332 of the second member 331 defines a slot 338 that receives a portion of the transfer conduit 318 such that an end portion of the transfer conduit 318 can physically and fluidically couple to the inlet port 354 of the adapter 350, as described in further detail herein.

The distal end portion 333 includes a plunger 337 configured to form a friction fit with the inner surface of the first member 321 defining the inner volume 326 when the second member 331 is disposed therein. Similarly stated, the plunger 337 defines a fluidic seal with the inner surface first member 321 that defines the inner volume 326 such that a portion of the inner volume 326 proximal to the plunger 337 is fluidically isolated from a portion of the inner volume 326 distal to the plunger 337. Moreover, at least a portion of the second member 331 is movable within the inner volume 326 of the first member 321 between a first position (e.g., a distal position) and a second position (e.g., a proximal position). In some instances, such movement of the second member 331 can, in turn, transition the actuator mechanism 320 between a first configuration and a second configuration, respectively.

The adapter 350 included in the transfer device can be any suitable shape, size, or configuration. As shown in FIGS. 8-10, the adapter 350 includes a proximal end portion 351, the distal end portion 352, the inlet port 354, and a puncture member 353. The distal end portion 352 includes and/or is coupled to the inlet port 354 and the puncture member 353, as shown in FIG. 10. Furthermore, the inlet port 354 and the puncture member 353 collectively define a fluid flow path between a volume substantially outside of the adapter 350 (e.g., distal to the adapter 350 such as the inner volume 339 of the second member 331) and an inner volume 355 of the adapter 350. Although not shown in FIGS. 8-10, in some embodiments, the distal end portion 352 of the adapter 350 can include any suitable coupling mechanism, locking mechanism, and/or the like (not shown) configured to physically and fluidically couple the adapter 350 to the second member 331 of the actuator mechanism 320. In other embodiments, the distal end portion 352 of the adapter 350 can be coupled to the second member 331 via a friction fit, a snap fit, a press fit, and/or the like. As described above, the inlet port 354 of the adapter 350 is physically and fluidically coupled to the transfer conduit 318 when the adapter 350 is coupled to the second member 331. Thus, with the inlet port 354 in fluid communication with the puncture member 353 and with the transfer conduit 318 in fluid communication with the port 329 of the first member 321, the puncture member 353 can be selectively placed in fluid communication with a portion of the inner volume 315 of the housing 310 that is distal to the plunger 327 of the first member 321, as described in further detail herein.

The proximal end portion 351 of the adapter 350 is open and is configured to receive a portion of a sample reservoir such as, for example, an ampoule, a vial, an evacuated container (e.g., a Vacutainer™), a culture bottle, and/or the like. For example, in some embodiments, an evacuated container (not shown in FIGS. 8-10) can be inserted into the adapter 350 and positioned such that the puncture member 353 of the adapter 350 punctures and/or pierces a septum of the evacuated container. As such, the puncture member 353 (e.g., a needle), the distal end portion 352 of the adapter 350, and the outlet portion 314 of the housing 310 can collectively define a fluid flow path between at least a portion of the inner volume 315 of the housing 310 and an inner volume of the evacuated container, as described in further detail herein.

The adapter 350 includes at least one sterilization member 380. Specifically, in this embodiment, the adapter 350 includes two sterilization members 380, as shown in FIGS. 9 and 10. The sterilization members 380 can be any suitable shape, size, and/or configuration. For example, in some embodiments, the sterilization members 380 can have a size and/or shape associated with a given fluid reservoir, culture bottle, and/or the like. Expanding further, the sterilization members 380 include a sterilization pad 381 that is configured to sterilize a surface of a given fluid reservoir when the fluid reservoir is placed in contact with the sterilization member 380. In some embodiments, for example, a portion of a fluid reservoir can be inserted into the sterilization member 380 to place the sterilization pad 381 in contact with a surface of the fluid reservoir, which in turn, can be punctured by the puncture member 353 of the adapter 350. In some embodiments, the sterilization member 380 is configured to be temporarily coupled to the fluid reservoir when the portion of the fluid reservoir is disposed therein. As such, a user can move the fluid reservoir relative to the transfer device 300 to remove the sterilization member 380 from the adapter 350. In this manner, the adapter 350 can be configured to force compliance with sterilization protocols and/or the like. In some embodiments, the sterilization members 380 can be substantially similar in form and function to those described in U.S. Patent Publication No. 2015/0246352 entitled, "Apparatus and Methods for Disinfection of a Specimen Container," filed Mar. 3, 2015, the disclosure of which is incorporated herein by reference in its entirety.

In use, a user can engage the transfer device 300 to couple the inlet port 313 to a proximal end portion of a lumen-defining device (not shown) such as, for example, a butterfly needle, a cannula assembly, a trocar (which is some cases is used to insert a catheter into a patient), and/or any of the devices described above with reference to the transfer device 200 in FIGS. 2-7. The distal end portion of the lumen-defining device can be disposed within a portion of the body of a patient (e.g., a vein), as described in detail above with reference to the transfer device 200 in FIGS. 2-7. With the inlet port 313 coupled to the lumen-defining device, a user (e.g., a phlebotomist, a nurse, a technician, a physician, or the like) can transition the transfer device 300 from a first configuration (FIG. 10) to a second configuration. More specifically, the user can engage the proximal end portion 332 of the second member 331 and/or the adapter 350 to move the second member 331 in the proximal direction relative to the first member 321 from its first position (e.g., a distal position) to its second configuration (e.g., a proximal position), thereby placing the transfer device 300 in the second configuration, as described in detail above with reference to the transfer device 200. Thus, the inlet port 313 of the housing 310 and the valve 330 disposed within the plunger 327 of the first member 321 define a fluid flow path that places the first reservoir 360 in fluid communication with the lumen-defining device and more particularly, the portion of the patient (e.g., the vein), as described in detail above with reference to the transfer device 200. As such, a volume of bodily-fluid is drawn through the inlet port 313 and the valve 330 and into the first reservoir 360, which, in some instances, can contain undesirable microbes such as dermally-residing microbes and/or other external contaminants (e.g., microbes within a lumen defined by the transfer device 300, microbes within the lumen defined by the lumen defining device, and/or any other undesirable microbe not present in the bodily-fluid source such as the bloodstream). As described above, in some instances, the magnitude of the suction force can be modulated by increasing or decreasing the amount of a force applied to the actuation mechanism 320. In this manner, the rate of change (e.g., the increase) in the volume of the first reservoir 360 can be sufficiently slow to allow time for the negative pressure differential between the vein and the first reservoir 360 to come to equilibrium before further increasing the volume of the first reservoir 360.

While in the second configuration, the transfer device 300 can be configured to transfer a desired amount (e.g., a predetermined amount) of bodily-fluid transferred to the first reservoir 360. In some embodiments, the first, predetermined amount can substantially correspond to the size of the first reservoir 360. In other embodiments, the first amount can substantially correspond to an equalization of pressure within the first reservoir 360 and the portion of the patient. Moreover, in such embodiments, the equalization of the pressure can be such that the valve 330 is allowed to return to the closed configuration. Thus, the first reservoir 360 is fluidically isolated from a volume substantially outside the first reservoir 360.

With the first amount fluidically isolated, the device 300 can be transitioned from the second configuration to a third configuration by further moving the actuator mechanism 320 in the proximal direction. For example, the user can apply a force to the proximal end portion 332 of the second member 331 to move the actuator mechanism 320 relative to the housing 310. Expanding further, in some embodiments, the plunger 337 of the second member 331 can be in contact with the proximal end portion 322 of the first member 321, such that further application of force on the proximal end portion 332 of the second member 331 collectively moves the first member 321 and the second member 331 in the proximal direction relative to the housing 310. The arrangement of the first member 321 within the inner volume 315 of the housing 310 is such that the proximal motion of the first member 321 increases the volume of the portion of the inner volume 315 that is distal to the plunger 327, thereby defining the second reservoir 370. Furthermore, with the plunger 327 forming a fluid tight seal with the inner surface of the housing 310 that defines the inner volume 315 and with the valve 330 in the closed configuration, the increase of volume produce a negative pressure within the second reservoir 370, as described in detail above with reference to the transfer device 200.

As described above, the negative pressure within the second reservoir 370 produced by the movement of the plunger 327 introduces a suction force within the portion of the patient that is sufficient to draw a volume of bodily-fluid through the inlet port 313 and into the second reservoir 370. In addition, by fluidically isolating the first reservoir 360, the bodily-fluid contained within the second reservoir 370 is substantially free from microbes generally found outside of the portion of the patient (as described above). Thus, the user can withdraw a bodily-fluid from the patient until a desired volume of the bodily-fluid is disposed in the second reservoir 370.

In some embodiments, with the desired amount of bodily-fluid disposed within the second fluid reservoir 370, the inlet port 313 of the housing 310 can be removed from the lumen-defining device and the adapter 350 can be coupled to a sampling container (e.g., a vile, a test tube, a petri dish, a culture medium, a test apparatus, a cartridge designed for use with an automated, rapid microbial detection system, or the like (not shown) such that at least a portion of the volume of bodily-fluid can be transferred from the second reservoir 370 to the sampling container to be tested. More specifically, in some instances, a user can insert a portion of a sampling container (e.g., specimen container, culture bottle, and/or the like) into the adapter 350 and a sterilization member 380 to place a surface of the sampling container and/or the like in contact with the sterilization pad 381. Once the surface is sufficiently sterilized, the sterilization member 380 can be removed from the sampling container and a portion of the sampling container can be re-inserted into the adapter 350 such that the puncture member 353 punctures the surface of the sampling container. In other embodiments, the puncture member 353 can penetrate through the sterilization member 380 and/or the sterilization pad 381 to prevent having to remove the sterilization member 380 prior to facilitating fluid communication with the sampling container. With the sampling container in fluid communication with the puncture member 353, at least a portion of the bodily-fluid disposed within the second reservoir 370 can be transferred to the sampling container via, for example, the port 328 of the first member 321, the transfer conduit 318, and the outlet port 319, and the puncture member 353. Moreover, in some embodiments, the sampling container (e.g., culture bottle and/or the like) can define a negative pressure and/or any other suitable mechanism configured to produce a negative pressure differential that is operable in drawing a volume of bodily-fluid from the second reservoir 370 and into an inner volume of the sampling container and/or fluid reservoir. As such, the bodily-fluid within the sampling container can be used for any number of testing processes or procedures such as, for example, blood culture testing, real-time diagnostics, and/or PCR-based approaches, while minimizing false results that might otherwise result from undesirable microbes or the like.

Although described above as transferring at least a portion of the volume of bodily-fluid disposed in the second volume 370 into the culture bottle and/or the like, in other embodiments, the user can manipulate the transfer device 300 to move the actuator mechanism 320 relative to the housing 310 in the distal direction. As such, at least a portion of the bodily-fluid disposed in the second volume 370 can be expelled therefrom and into, for example, an assay, dish, fluid reservoir, and/or the like used in, for example, blood culture testing, real-time diagnostics, and/or PCR-based approaches, while minimizing false results that might otherwise result from undesirable microbes or the like, as described in detail above with reference to the transfer device 200.

FIGS. 11-15 illustrate a syringe-based transfer device 400 according to an embodiment. The syringe-based transfer device 400 (also referred to herein as "bodily-fluid transfer device," "fluid transfer device," or "transfer device") includes a housing 410 and an actuator mechanism 420. The transfer device 400 is configured to include or define a first fluid reservoir 460 (also referred to herein as "first reservoir" or "pre-sample reservoir") and a second fluid reservoir 470 (also referred to herein as "second reservoir" or "sample reservoir"). The transfer device 400 can be any suitable shape, size, or configuration. For example, while shown in FIGS. 11-15 as being substantially cylindrical, the transfer device 400 can be square, rectangular, polygonal, and/or any other non-cylindrical shape. Moreover, portions of the transfer device 400 can be substantially similar in form and/or function to portions of the transfer devices 200 and/or 300 described above. Therefore, such portions are not described in further detail herein.

The housing 410 of the transfer device 400 includes a proximal end portion 411 and a distal end portion 412 and defines an inner volume configured to at least partially define the second fluid reservoir 470 (as described in further detail herein). The proximal end portion 411 of the housing 410 is substantially open and movably receives at least a portion of the actuator mechanism 420. The distal end portion 412 of the housing 410 includes an inlet port 413 that is in selective fluid communication with the inner volume of the housing 410 and a volume defined by the actuator mechanism 420 (e.g., the first fluid reservoir 460). As described above, in some embodiments, at least a portion of the inlet port 413 can form a lock mechanism, which in turn, can physically and fluidically couple to a needle, a cannula, and/or other lumen-containing device (not shown in FIGS. 11-15) configured to be inserted into a portion of a patient. In this manner, the inlet port 413 can define at least a portion of a fluid flow path between the patient and the inner volume of the housing 410, the first fluid reservoir 460, and/or the second fluid reservoir 470, as further described herein.

Figure 11:
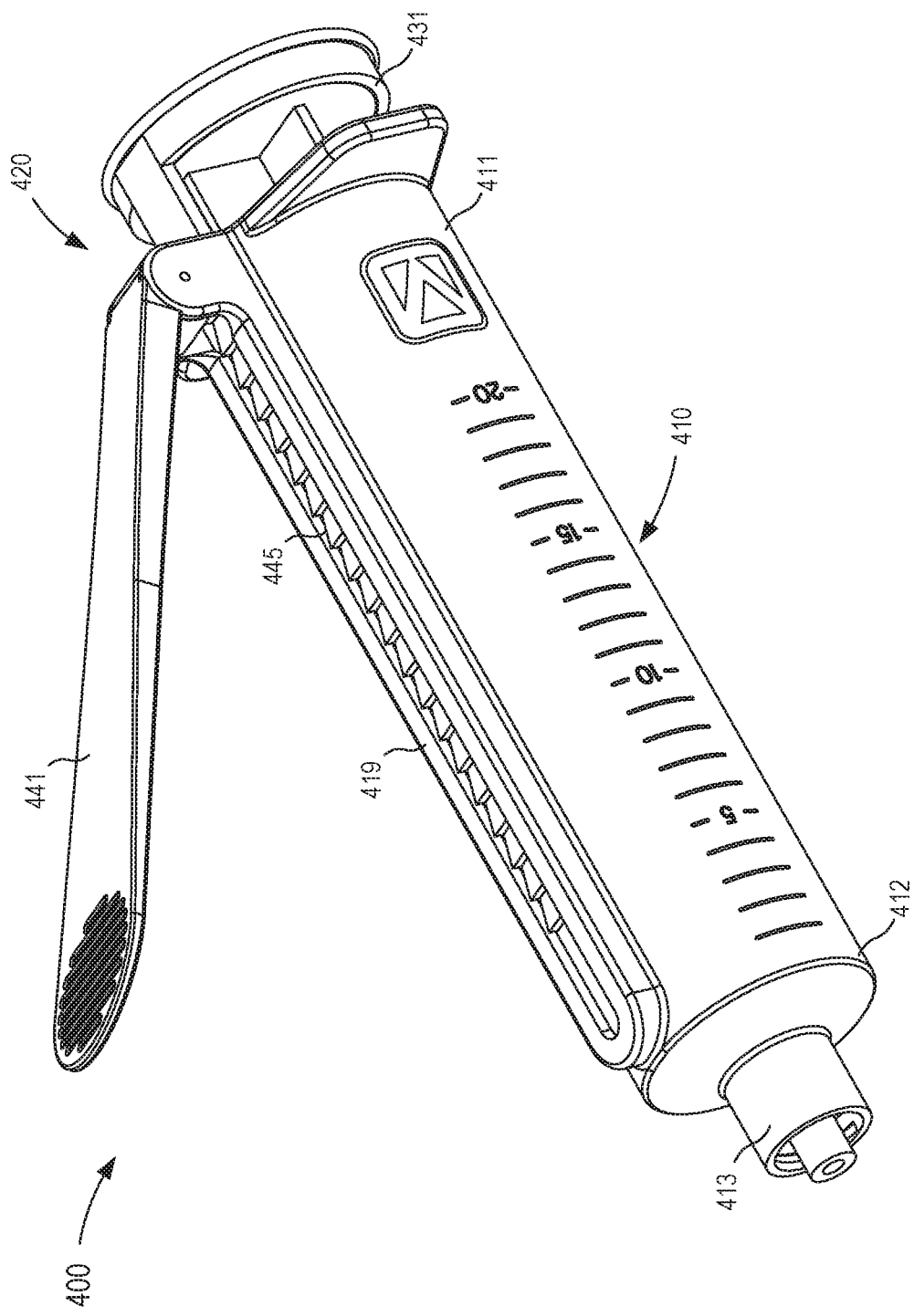
FIG. 11 is a perspective view of a syringe-based transfer device according to another embodiment.

As shown in FIG. 11, the housing 410 also includes an indicator portion 416 configured to provide a visual indication associated with a volume of fluid disposed within the housing 410. The indicator portion 416 can be any suitable configuration. For example, in some embodiments, the indicator portion 416 can be substantially similar to the indicator portion 216 of the housing 210 described above with reference to the transfer device 200 and thus, is not described in further detail herein. In other embodiments, the housing 410 does not include an indicator portion and as an alternative, includes any suitable feature or mechanism configured to indicate a volume of bodily-fluid within the housing 410 and/or configured to otherwise dictate an amount of bodily-fluid that is transferred into the housing 410 (e.g., an expandable volume, a predetermined level of negative pressure, and/or the like).

Figure 12:
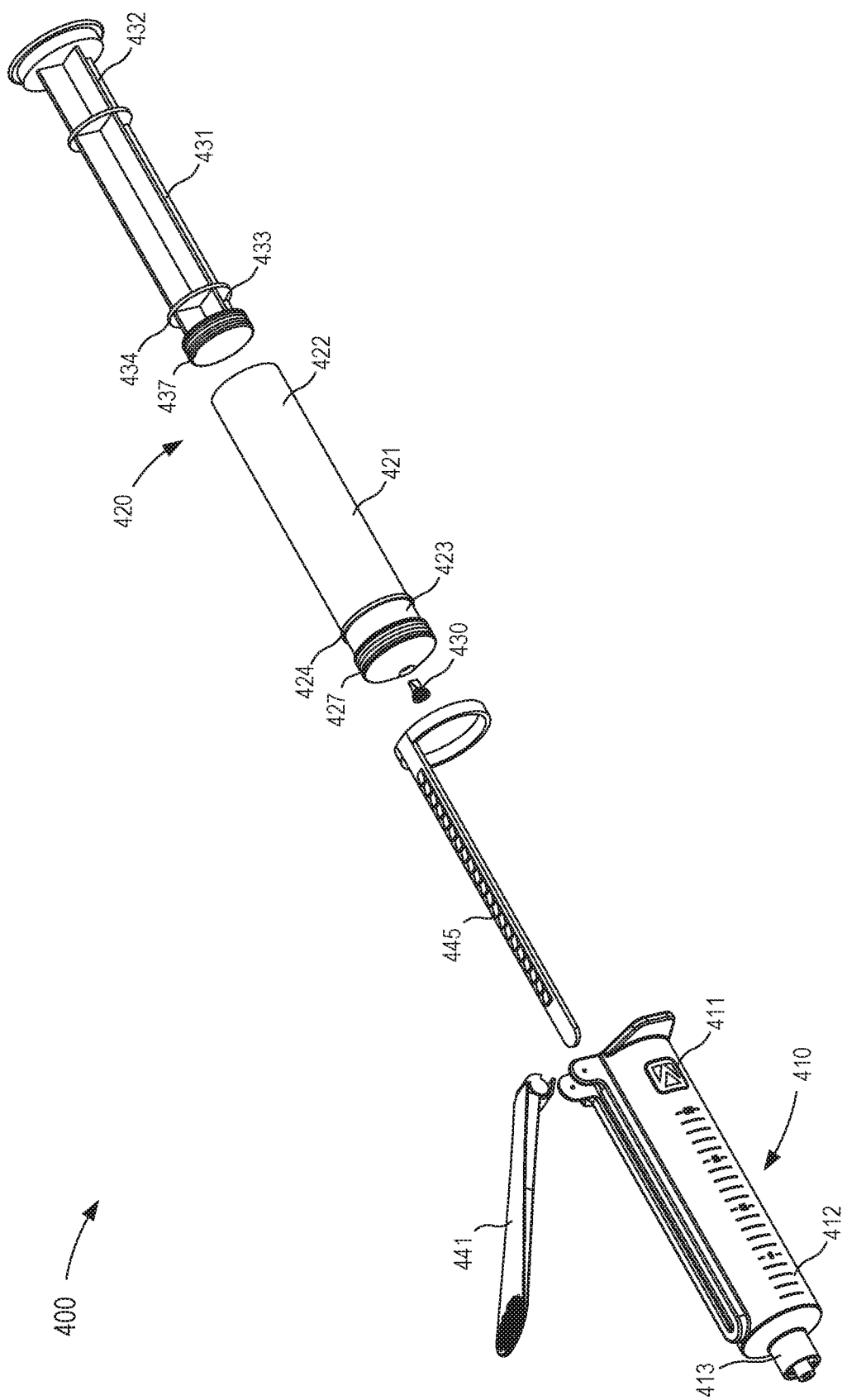
FIG. 12 is an exploded view of the syringe-based transfer device of FIG. 11.
Figure 13:
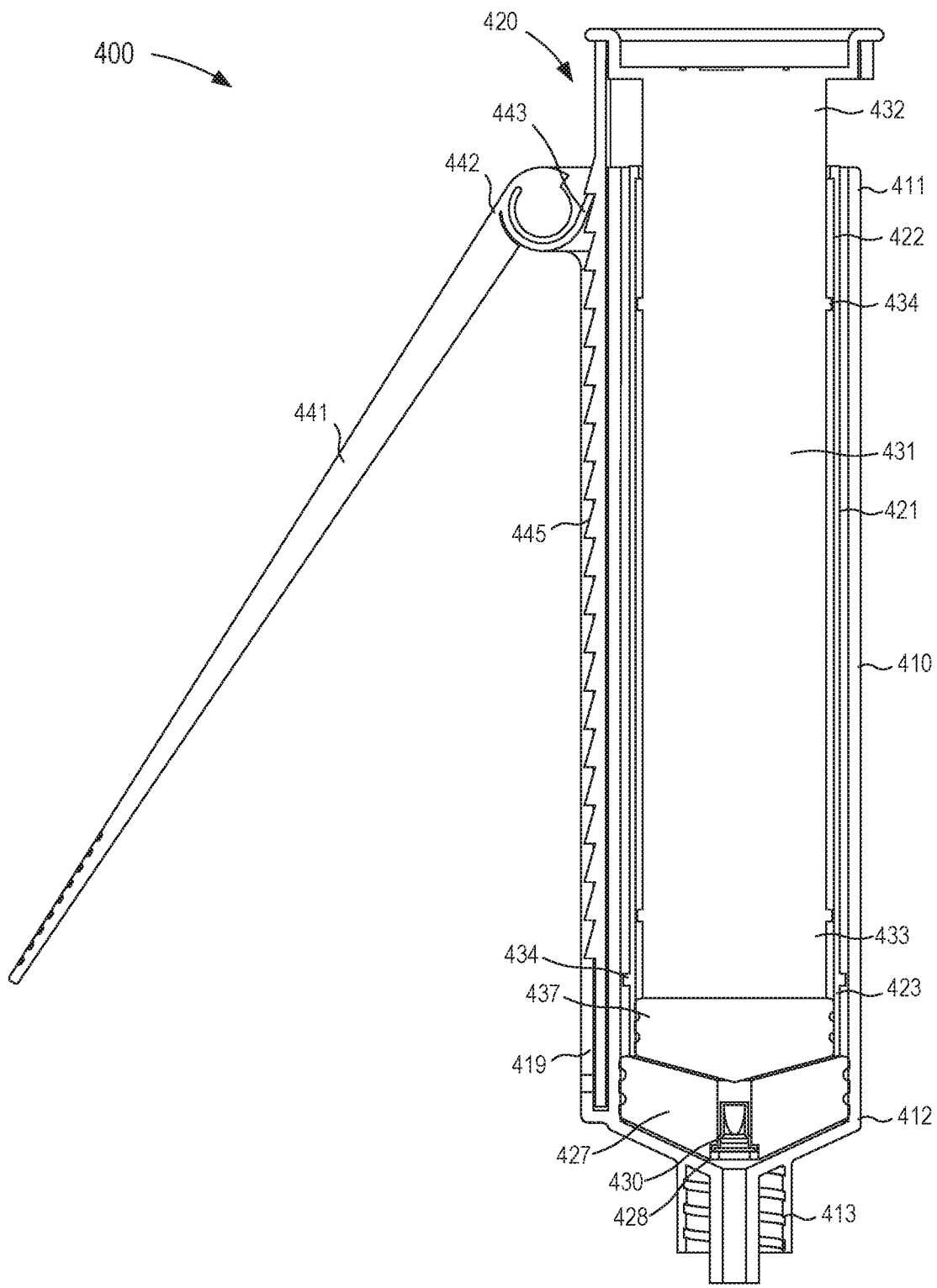
FIGS. 13-15 are cross-sectional views of the syringe-based transfer device of FIG. 11 taken along the line $X_3$-$X_3$, in a first configuration, a second configuration, and a third configuration, respectively.

The actuator mechanism 420 of the device 400 is at least partially disposed within the inner volume and is movable between a first position (e.g., a distal position relative to the housing 410) and a second position (e.g., a proximal position relative to the housing 410). The movement of the actuator mechanism 420 relative to the housing 410 can transition the device 400 between at least a first, a second, and a third configuration, as further described herein. As shown in FIGS. 11 and 12, the actuator mechanism 420 includes a first member 421, a second member 431, an actuator lever 441, and a rack 445. The actuator lever 441 and the rack 445 are movably coupled to the housing 410 and are operable in moving the first member 421 and/or the second member 431 relative to the housing 410. The actuator lever 441 is coupled to a portion of the housing 410 and is configured to move relative thereto in a rotational or pivoting motion to selectively engage the rack 445. More particularly, the actuator lever 441 includes a clip 443 or the like configured to selectively engage the rack 445 as the actuator lever 441 is rotated relative to the housing 410.

The rack 445 is slidably disposed in a channel 419 (e.g., a slot, track, etc.) defined by an outer portion of the housing 410 and is configured to move relative thereto in a translational motion (e.g., in a proximal and/or a distal direction) in response to being engaged and/or moved by the actuator lever 441. For example, as shown in FIGS. 11 and 12, the rack 445 includes a set of linearly arranged teeth or the like that are selectively engaged by the clip 443 of the actuator lever 441 when the actuator lever 441 is rotated relative to the housing 410. An end portion of the rack 445 is coupled to the second member 431 of the actuator mechanism 420. In this manner, a user can manipulate the actuator lever 441 to move the first member 421 and/or the second member 431 of the actuator mechanism 420 relative to the housing 410, as described in further detail herein.

The first member 421 of the actuator mechanism 420 can be any suitable shape, size, and/or configuration. For example, in some embodiments, the first member 421 can be substantially similar in form and/or function to the first member 221 of the transfer device 220 and thus, similar aspects are not described in further detail herein. As shown, for example, in FIGS. 12-15, the first member 421 includes a proximal end portion 422 and a distal end portion 423 and defines an inner volume therebetween configured to define at least a portion of the first reservoir 460, as further described herein. The proximal end portion 422 of the first member 421 is open and configured to receive at least a portion of the second member 431 therethrough. The distal end portion 423 of the first member 421 includes a plunger 427. The plunger 427 is configured to form a friction fit with the inner surface of the housing 410 that defines the inner volume to collectively define a fluidic seal therebetween. As described above with reference to the first member 221 of the transfer device 200, the plunger 427 defines a channel 428, which receives and/or includes a valve 430. The valve 430 can be any suitable valve such as those described herein and is configured to selectively place the inner volume defined by the first member 421 (e.g., the first fluid reservoir 460) in fluid communication with the inlet port 413 of the housing 410 (e.g., when in an open configuration).

The second member 431 of the actuator mechanism 420 includes a proximal end portion 432 and a distal end portion 433. The proximal end portion 432 is coupled to the rack 445 such that movement of the rack 445 results in movement of the second member 431, as described in further detail herein. The distal end portion 433 of the second member 431 includes a plunger 437 configured to form a friction fit with an inner surface of the first member 421 defining the inner volume to collectively define a fluidic seal therebetween.

As described above, at least a portion the second member 431 is configured to be movably disposed within the inner volume of the first member 421. The second member 431 can be movable between a first position (e.g., a distal position) and a second position (e.g., a proximal position) thereby transitioning the actuator mechanism 420 between a first configuration and a second configuration, respectively. The second member 431 includes a protrusion 434 that extends in a radial direction to selectively engage a proximal surface of the first member 421 (see e.g., FIGS. 14 and 15), which in turn, selectively limits a distal movement of the second member 431 relative the first member 421, as described in further detail herein.

In use, a user can engage the transfer device 400 to couple the inlet port 413 to a proximal end portion of a lumen-defining device (not shown) such as, for example, a butterfly needle, a cannula assembly, a trocar (which is some cases is used to insert a catheter into a patient), and/or any of the devices described above with reference to the transfer device 200 in FIGS. 2-7. The distal end portion of the lumen-defining device can be disposed within a portion of the body of a patient (e.g., a vein). In this manner, the inlet port 413 is placed in fluid communication with the portion of the body. With the inlet port 413 coupled to the lumen-defining device, a user (e.g., a phlebotomist, a nurse, a technician, a physician, or the like) can transition the transfer device 400 from the first configuration (see e.g., FIG. 13) to the second configuration (see e.g., FIG. 14).

Figure 14:
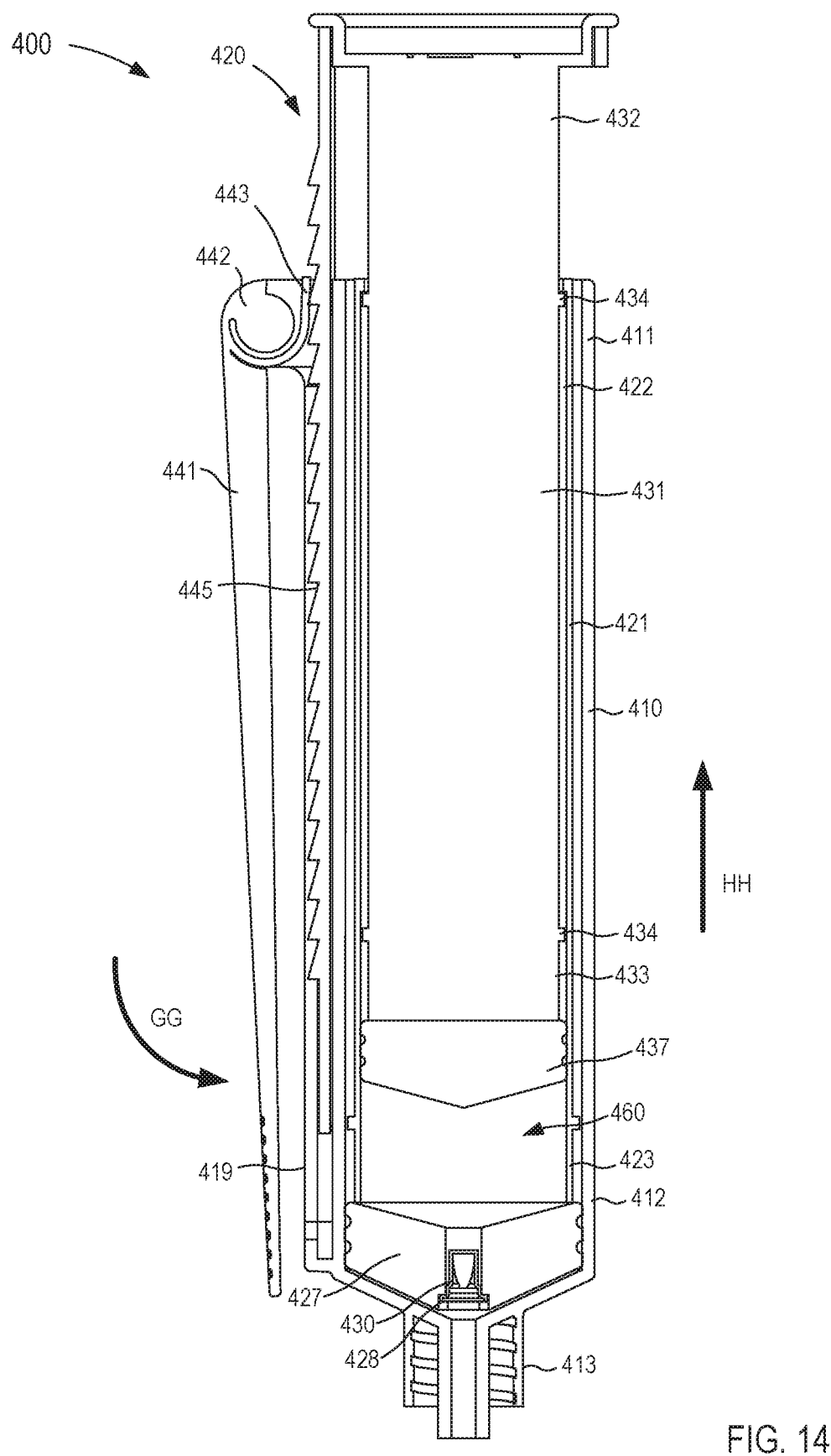

In some instances, for example, the user can engage the actuator lever 441 to pivot the actuator lever 441 relative to the housing 410, as indicated by the arrow GG in FIG. 14.

The rotation of the actuator lever 441 results in a similar rotation of the clip 443, which in turn, engages and/or contacts at least a portion of the rack 445, thereby moving the rack 445 in a linear direction along or within the channel 419 of the housing 410. More specifically, the rotation of the actuator lever 441 and the clip 443 moves the rack 445 relative to the housing 410 in the proximal direction, as indicated by the arrow HH in FIG. 14. Thus, with the rack 445 coupled to the second member 431 of the actuator mechanism 420, the movement of the rack 445 in the proximal direction results in a similar movement of the second member 431 in the proximal direction relative to the first member 421, as indicated by the arrow HH. As shown in FIG. 14, in some instances, the second member 431 is moved in the proximal direction relative to the first member 421 (e.g., the first member 421 does not substantially move in the proximal direction) until the protrusion 434 of the second member 431 is placed in contact with a surface of the first member 421 (e.g., a protrusion extending from an inner surface of the first member 421 at or near the proximal end portion 423.

The arrangement of the second member 431 within the first member 421 is such that the proximal motion of the second member 431 increases a distance between the plunger 427 of the first member 421 and the plunger 437 of the second member 431. In other words, the movement of the second member 431 relative to the first member 421 increases a volume of the first member 421 defined between the plungers 427 and 437. As described above with reference to the transfer device 200, the increase in the volume is such that the first reservoir 460 is defined between the plungers 427 and 437, as shown in FIG. 14. Furthermore, with the plunger 437 forming a fluid tight seal with the inner surface of the first member 421, the increase of volume produces a negative pressure within the first reservoir 460, which can be sufficient to transition the valve 430 from a closed configuration to an open configuration, as described above with reference to the transfer device 200. Thus, the inlet port 413, the valve 430, and the channel 428 define a fluid flow path that places the first reservoir 460 in fluid communication with the lumen-defining device and more particularly, the portion of the patient (e.g., the vein) such that a volume of bodily-fluid can flow from the patient and into the first reservoir 460. In some embodiments, the bodily-fluid can contain undesirable microbes such as, for example, dermally-residing microbes and/or other external contaminants (e.g., microbes within a lumen defined by the transfer device 400, microbes within the lumen defined by the lumen defining device, and/or any other undesirable microbe not present in the bodily-fluid source such as the bloodstream), as described above with reference to the transfer device 200.

As the actuator mechanism 420 is transitioned to the second configuration and/or while the actuator mechanism 420 is in the second configuration (see e.g., FIG. 14), the transfer device 400 transfers a desired amount (e.g., a predetermined amount) of bodily-fluid to the first reservoir 460. In some embodiments, the first, predetermined amount can substantially correspond to the size of the first reservoir 460. In other embodiments, the first amount can substantially correspond to an equalization of pressure within the first reservoir 460 and the portion of the patient. Moreover, in such embodiments, the equalization of the pressure can be such that the valve 430 returns to the closed configuration. Thus, the first reservoir 460 is fluidically isolated from a volume substantially outside the first reservoir 460.

With the first amount fluidically isolated within the first fluid reservoir 460, the device 400 can be transitioned from the second configuration (FIG. 14) to the third configuration (FIG. 15) by further manipulating the actuator lever 441. For example, although not shown in FIGS. 11-15, the actuator lever 441 can include and/or can be coupled to a bias member such as a rotational spring or the like that can bias the actuator lever 441 in the first position (e.g., in the position shown in FIG. 13). In some embodiments, for example, the clip 443 can be a bias member or the like. As such, the user can remove and/or reduce a force applied on the actuator lever 441 that can allow and/or can result in the actuator lever 441 rotating relative to the housing 410 in a substantially opposite direction (e.g., such that the end portion of the actuator lever 441 is moved away from the housing 410. Moreover, the arrangement of the rack 445 can be such that the clip 441 moves along the rack 445 as the actuator lever 441 is moved toward the first position. In this manner, the rack 445 can remain in a substantially fixed position relative to the housing 410 and/or the actuator lever 441 as the actuator lever 441 moves to the first position. Once, the actuator lever 441 is in the first position and/or after the actuator lever 441 is moved from the second position (FIG. 14), the user can again exert a force on the actuator lever 441 to rotate the actuator lever 441 in the direction of the arrow GG in FIG. 14. In this manner, the actuator lever 441 can act as a ratchet or trigger that can be manipulated a series or number of times to move the rack 445 relative to the housing 410.

Figure 15:
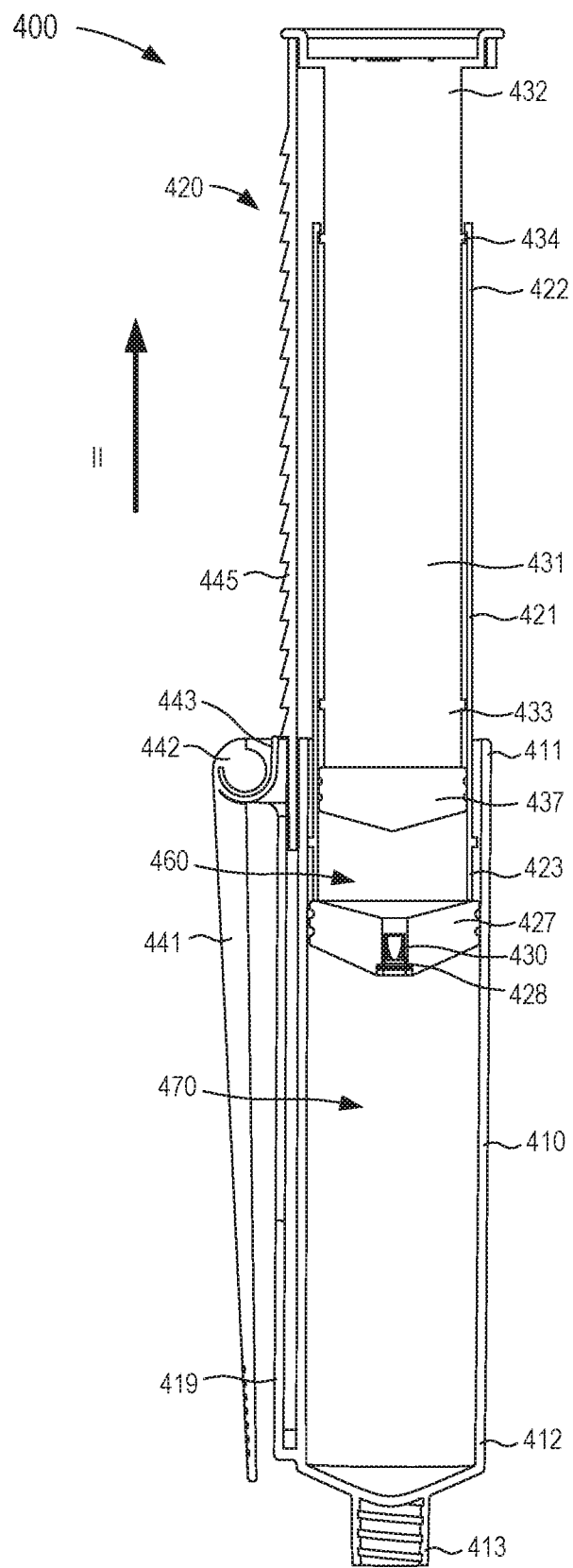

The actuator lever 441 can be actuated and/or manipulated any number of times to move the second member 431 to a third position, as indicated by the arrow II in FIG. 15. As shown, the first member 421 is configured to move with the second member 431 as the second member 431 is moved from the second position to the first position. More specifically, once the protrusions 434 of the second member 431 are placed in contact with the portion of the first member 421, any further movement of the second member 431 in the proximal direction results in a similar movement of the first member 421 in the proximal direction (see e.g., FIGS. 14 and 15).

As described above with reference to the second member 431, the arrangement of the first member 421 within the housing 410 is such that the proximal motion of the first member 421 increases a volume within the housing 410 that is distal to the plunger 427, thereby defining the second reservoir 470, as shown in FIG. 15. Furthermore, with the plunger 427 forming a fluid tight seal with the inner surface of the housing 410 and with the valve 430 in the closed configuration, the increase of volume produce a negative pressure within the second reservoir 470. Therefore, the negative pressure within the second reservoir 470 produced by the movement of the plunger 427 introduces a suction force within the portion of the patient that is sufficient to draw a volume of bodily-fluid through the inlet port 413 and into the second reservoir 470. In addition, by fluidically isolating the first reservoir 460, the bodily-fluid contained within the second reservoir 470 is substantially free from microbes generally found outside of the portion of the patient (as described above). In some embodiments, the user can visualize and/or otherwise quantify the volume of the bodily-fluid disposed in the second reservoir 470 via the indication portion 416 of the housing 410. For example, in some instances, the volume of the bodily-fluid disposed in the second reservoir 470 substantially corresponds to a line, gradation, marker, tic mark, etc. included in the indication portion 416. Thus, the user can withdraw a bodily-fluid from the patient until a desired volume of the bodily-fluid is disposed in the second reservoir 470, as described in detail above with reference to the transfer device 200.

Although not shown in FIGS. 11-15, once the desired volume of bodily-fluid is disposed in the second reservoir 470, the transfer device 400 can be transitioned from the third configuration to a fourth configuration. For example, in some embodiments, the inlet port 413 of the housing 410 can be removed from the lumen-defining device and can be coupled to a sampling container (e.g., a vile, a test tube, a petri dish, a culture medium, a test apparatus, a cartridge designed for use with an automated, rapid microbial detection system, or the like (not shown)) such that at least a portion of the volume of bodily-fluid can be transferred from the second reservoir 470 to the sampling container to be tested, as described above with reference to the transfer device 200. For example, the bodily-fluid can be expelled from the second fluid reservoir 470 to be used for any number of testing processes or procedures such as, for example, blood culture testing, real-time diagnostics, and/or PCR-based approaches, while minimizing false results that might otherwise result from undesirable microbes or the like.

In some embodiments, the arrangement of the actuator lever 441 and the rack 445 can, for example, control and/or limit a magnitude and/or rate of pressure change within the fluid reservoirs 460 and/or 470. For example, in some instances, it may be desirable to limit the amount of suction force introduced to a vein to avoid collapse of the vein and/or hemolysis of at least a portion of the bodily-fluid (e.g., blood). In this manner, the rate of change (e.g., the increase) in the volume of the first reservoir 460 and/or the second reservoir 470 can be sufficiently slow to allow time for the negative pressure differential between the vein and the fluid reservoirs 460 and/or 470 to come to equilibrium before further increasing the volume. Thus, the magnitude of the suction force can be modulated.

Figure 16:
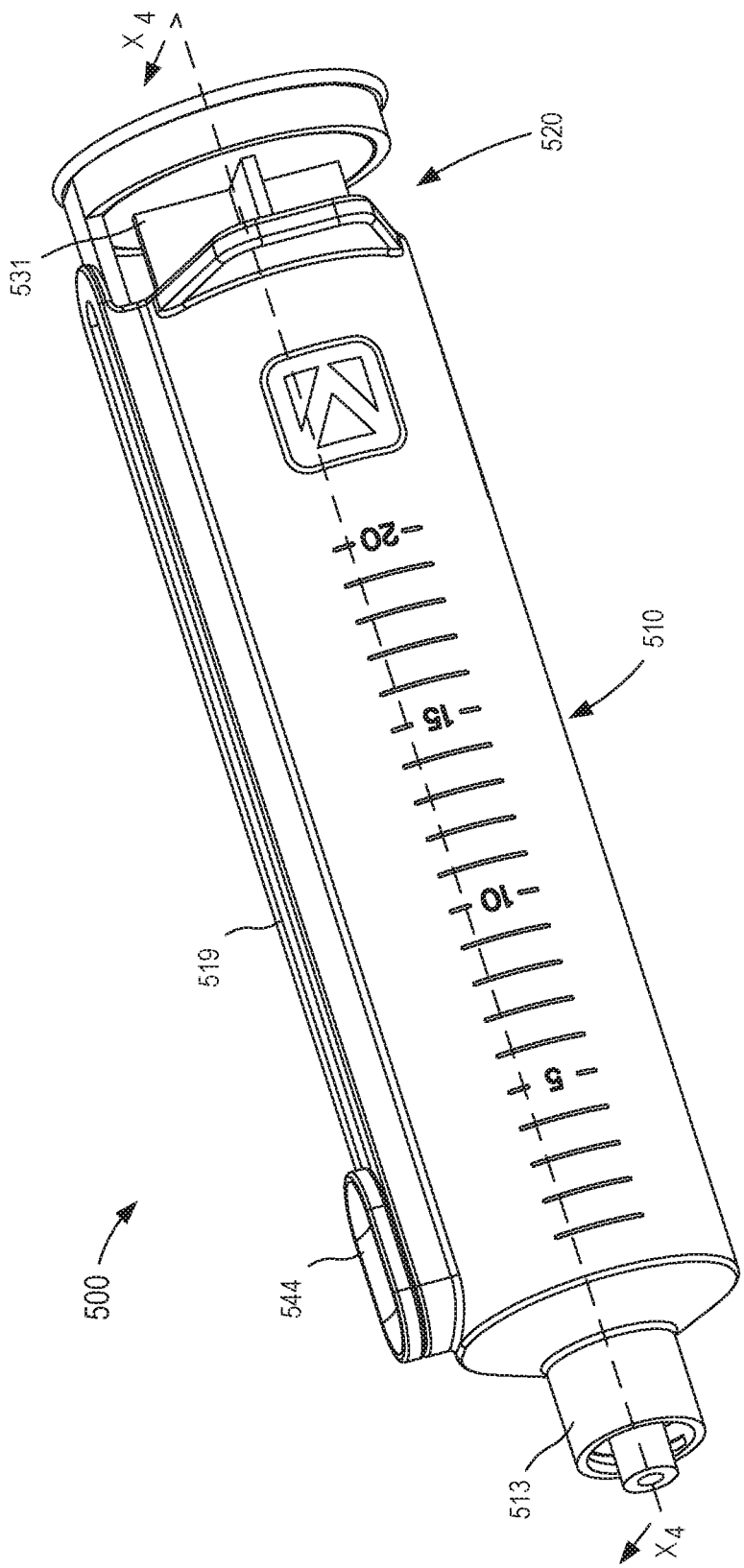
FIG. 16 is a perspective view of a syringe-based transfer device according to another embodiment.
Figure 17:
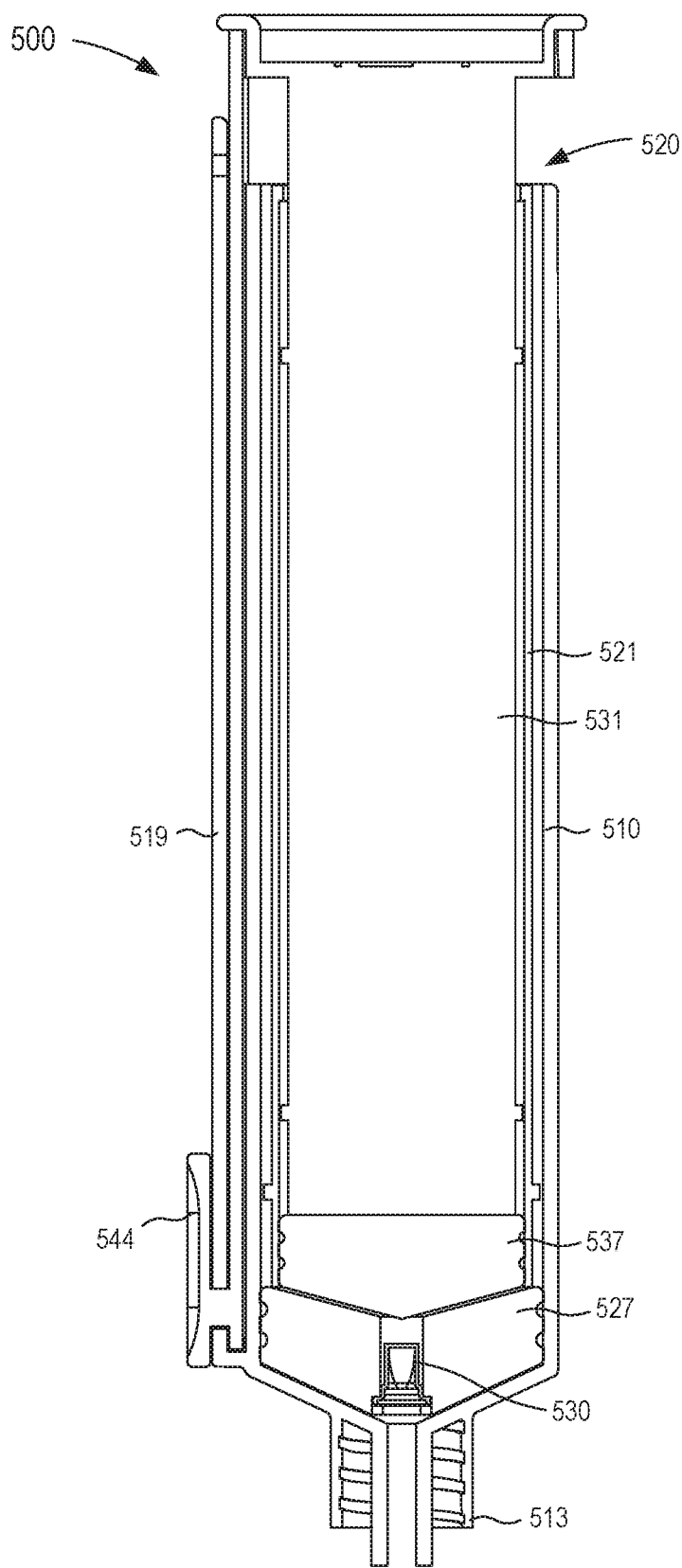
FIG. 17 is a cross-sectional view of the syringe-based transfer device of FIG. 16 taken along the line $X_4$-$X_4$.

While the actuator mechanism 420 is shown and described above as including the actuator lever 441 and the rack 445 that are operable in moving the first member 421 and the second member 431 relative to the housing 410, in other embodiments, a transfer device can include an actuator mechanism configured to move relative to a housing in response to any suitable input or the like. FIGS. 16 and 17 illustrate a syringe-based transfer device 500 according to an embodiment. The syringe-based transfer device 500 (also referred to herein as "bodily-fluid transfer device," "fluid transfer device," or "transfer device") includes a housing 510 and an actuator mechanism 520. The transfer device 500 is configured to include or define a first fluid reservoir 560 (also referred to herein as "first reservoir" or "pre-sample reservoir") and a second fluid reservoir 570 (also referred to herein as "second reservoir" or "sample reservoir"). The transfer device 500 can be substantially similar in form and/or function to transfer device 400 described above. Therefore, portions of the transfer device 500 that are similar to the transfer device 400 are briefly discussed below to identify relevant components but are not described in further detail herein.

As shown in FIGS. 16 and 17, the housing 510 of the transfer device 500 is substantially similar to the housing 410 of the transfer device 400. The housing 510 defines an inner volume configured to at least partially define the second fluid reservoir 570 (as described in further detail herein). A proximal end portion of the housing 510 is substantially open and movably receives at least a portion of the actuator mechanism 520. A distal end portion 512 of the housing 510 includes an inlet port 513 that is in selective fluid communication with the inner volume of the housing 510 and a volume defined by the actuator mechanism 520 (e.g., the first fluid reservoir 560). As described above, in some embodiments, at least a portion of the inlet port 513 can form a lock mechanism, which in turn, can physically and fluidically couple to a needle, a cannula, and/or other lumen-containing device (not shown in FIGS. 11-15) configured to be inserted into a portion of a patient. In this manner, the inlet port 513 can define at least a portion of a fluid flow path between the patient and the inner volume of the housing 510, the first fluid reservoir 560, and/or the second fluid reservoir 570, as further described herein.

The actuator mechanism 520 of the device 500 is at least partially disposed within the inner volume and is movable between a first position (e.g., a distal position relative to the housing 510) and a second position (e.g., a proximal position relative to the housing 510). The movement of the actuator mechanism 520 relative to the housing 510 can transition the device 500 between at least a first, a second, and a third configuration, as further described herein. As shown in FIGS. 16 and 17, the actuator mechanism 520 includes a first member 521, a second member 531, and a slider 544. In some embodiments, the actuator mechanism 520 can be substantially similar to the actuator mechanism 420 described above with reference to FIGS. 11-15.

The first member 521 of the actuator mechanism 520 can be any suitable shape, size, and/or configuration. For example, in some embodiments, the first member 521 can be substantially similar in form and/or function to the first member 421 of the transfer device 420 and thus, similar aspects are not described in further detail herein. As shown in FIG. 17, the first member 521 is movably disposed in the housing 510. A proximal end portion of the first member 521 is substantially open to allow the second member 531 to be movably disposed within an inner volume defined by the first member 521 such that the first member 521 and the second member 531 collectively define the first fluid reservoir 560, as described above with reference to the transfer devices 200, 300, and/or 400. A distal end portion of the first member 521 includes and/or is coupled to a plunger 527 configured to form a friction fit with the inner surface of the housing 510 such that the first member 521 and the housing 510 collectively define the second fluid reservoir 570. As described above with reference to the transfer devices 200, 300, and/or 400, the plunger 527 receives and/or includes a valve 530 configured to selectively place the inner volume defined by the first member 521 (e.g., the first fluid reservoir 560) in fluid communication with the inlet port 513 of the housing 510 (e.g., when in an open configuration).

The second member 531 of the actuator mechanism 520 can be any suitable shape, size, and/or configuration. For example, in some embodiments, the second member 531 can be substantially similar in form and/or function to the second member 431 of the transfer device 420 and thus, similar aspects are not described in further detail herein. As shown, a proximal end portion of second member 531 is coupled to an end portion of the slider 544 such that movement of the slider 544 results in movement of the second member 531 (e.g., similar to the rack 445 coupled to the second member 431 of the transfer device 400), as described in further detail herein. A distal end portion of the second member 531 includes and/or is coupled to a plunger 537 configured to form a friction fit with an inner surface of the first member 521 defining the inner volume to collectively define a fluidic seal therebetween. In this manner, the second member 531 can be movable between a first position (e.g., a distal position) and a second position (e.g., a proximal position)

thereby transitioning the actuator mechanism 520 between a first configuration and a second configuration, respectively.

The slider 544 of the actuator mechanism 520 is slidably disposed in a channel 519 (e.g., a slot, track, etc.) defined by an outer portion of the housing 510 and is configured to move relative thereto in a translational motion (e.g., in a proximal and/or a distal direction) in response to being engaged and/or moved by a user. For example, a first portion of the slider 544 can be movably or slidably disposed within the channel 519, while a second portion (e.g., an engagement portion or the like) is disposed outside of the channel 519. In this manner, a user can exert a force on the second portion that is operable in moving the slider 544 (e.g., first portion and the second portion of the slider 544) relative to the housing 510. Although not shown in FIGS. 16 and 17, the transfer device 500 can be transitioned between a first configuration (e.g., prior to use), a second configuration (e.g., the second member 531 is in a second position relative to the first member 521), and a third configuration (e.g., the first member 521 is in a second position relative to the housing 510) in a manner substantially similar to that described above with reference to the transfer device 400. The use of the transfer device 500 differs from the use of the transfer device 400 (described in detail above) in that the actuator mechanism 520 is moved relative to the housing 510 by exerting a manual force on the slider 544 rather than in response to movement of the actuator lever 441 included in the transfer device 400. Thus, the use of the transfer device 500 is not described in further detail herein.

While the housings 210, 310, 410, and 510 each include an inlet port configured to be coupled, externally, to a lumen defining device such as a needle or catheter, in other embodiments, a syringe-based transfer device can include a port or the like configured to receive at least of a device configured to establish fluid communication between an inner volume of the transfer device and a volume outside of the transfer device. For example, FIGS. 18-24 illustrate a syringe-based fluid transfer system 600 according to an embodiment. As described above, the syringe-based fluid transfer system 600 ("fluid transfer system" or "transfer system") can be used to receive and/or transfer a volume of fluid with reduced contamination such as dermally residing microbes or the like.

The transfer system 600 includes a transfer device 605, an adapter 650, an external fluid reservoir 685 (e.g., a sample bottle or the like), and a coupler 690. The transfer device 605 can be substantially similar in form and/or function to any of the transfer devices 200, 300, 400, and/or 500 described herein. Thus, such portions are described hereinbelow to identify relevant components and/or features of the transfer device 605 but are not described in further detail.

As shown, the transfer device 605 includes a housing 610 and an actuator mechanism 620, and includes and/or defines a first fluid reservoir 660 and a second fluid reservoir 670. The housing 610 of the transfer device 605 can be any suitable shape, size, or configuration. For example, in some embodiments, the housing 610 can be substantially similar in form and/or function to the housings 210, 310, 410, and/or 510 described above. For example, the housing 610 includes a proximal end portion 611 and a distal end portion 612 and defines an inner volume configured to at least partially define the second fluid reservoir 670, as described above, for example, with reference to the housing 210. The proximal end portion 611 of the housing 610 is substantially open and movably receives at least a portion of the actuator mechanism 620. The distal end portion 612 of the housing 610 includes an inlet port 613 that is in selective fluid communication with the inner volume of the housing 610 and a volume defined by the actuator mechanism 620 (e.g., the first fluid reservoir 660).

While the housing 610 is similar to the housings 210, 310, 410, and/or 510 described above, in this embodiment, the inlet port 613 can be arranged to receive a portion of a device configured to establish fluid communication between the inner volume of the housing 610 and/or a volume defined by the actuator mechanism 620 (described in further detail herein). For example, as shown in FIGS. 19-23, the inlet port 613 can be a septum, a frangible seal, a membrane, a cap, a self-healing port, a saline lock, a heparin lock, and/or any other suitable port configured to transition between a closed configuration and an open configuration.

Figure 19:
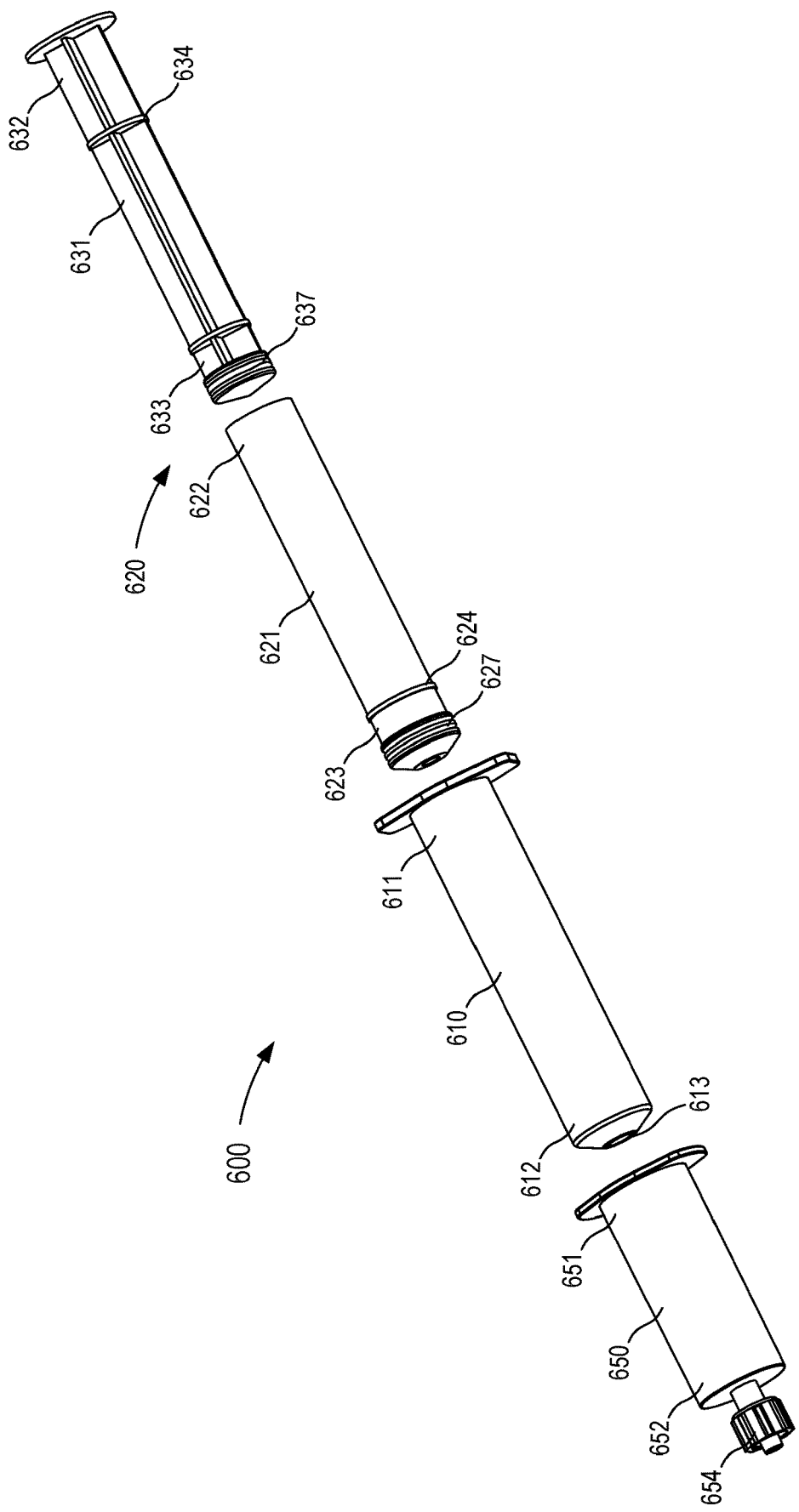
FIG. 19 is an exploded view of a syringe-based transfer device and a transfer adapter included in the syringe-based transfer system of FIG. 18.
Figure 20:
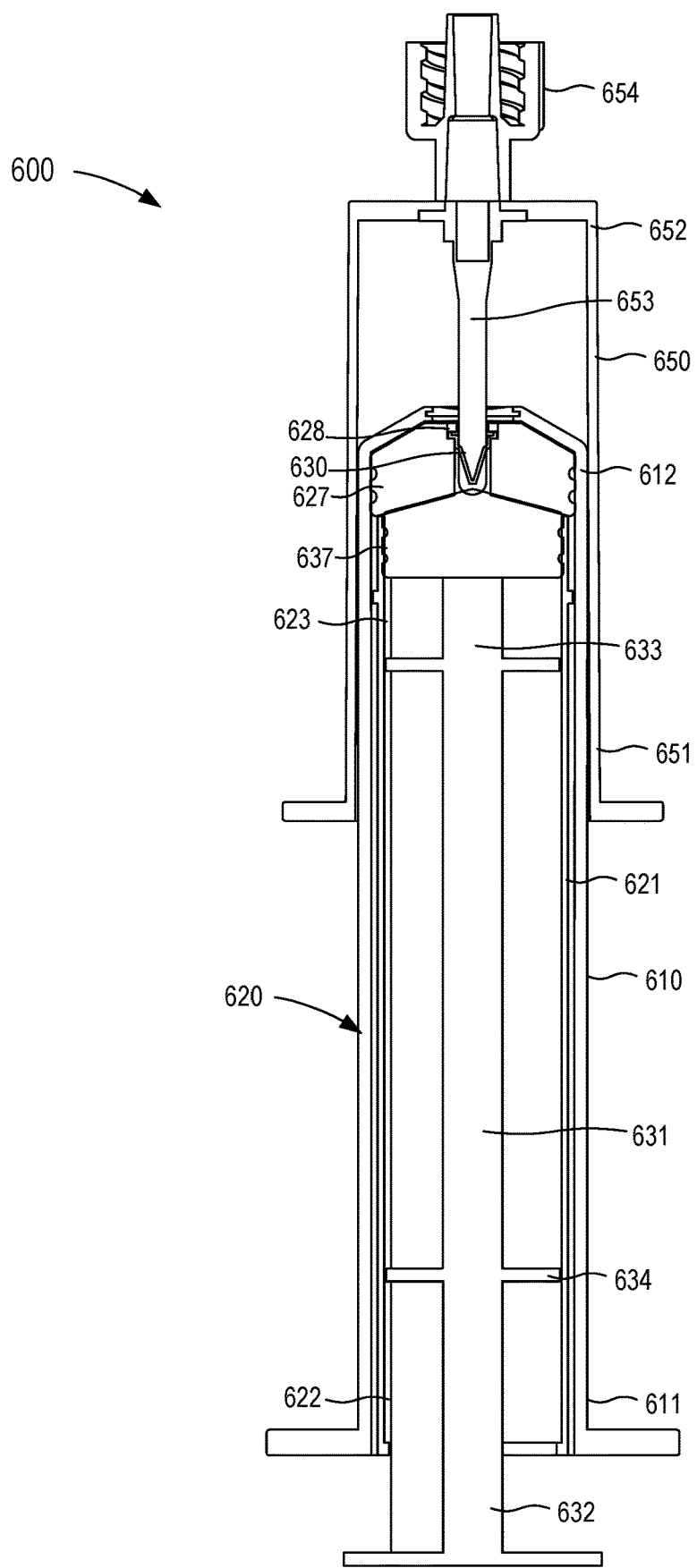
FIGS. 20-22 are cross-sectional view of the syringe-based transfer device and the transfer adapter taken along the line $X_5$-$X_5$, in a first configuration, a second configuration, and a third configuration, respectively.

As shown in FIGS. 18-20, the distal end portion 612 of the housing 610 is configured to be coupled to and/or disposed within the transfer adapter 650. Said another way, at least a portion of the transfer adapter 650 can be disposed about the proximal end portion 612 of the housing 610 to at least temporarily couple the transfer adapter 650 to the housing 610. As shown in FIG. 20, the transfer adapter 650 includes a proximal end portion 651 and a distal end portion 652. The proximal end portion 651 is substantially open to allow at least a portion of the transfer device 605 to be disposed therein. The distal end portion 652 includes a port 654 in fluid communication with a puncture member 653. The port 654 can be substantially similar to any of the inlet ports described above (e.g., the inlet port 213). For example, the port 654 can form a lock mechanism, which in turn, can physically and fluidically couple to a needle, a cannula, and/or other lumen-containing device (see e.g., FIG. 18) configured to establish fluid communication with a portion of a patient. Moreover, the puncture member 653 (e.g., a needle), is configured to puncture, pierce, and/or otherwise open the port 613 of the housing 610 when the adapter 650 is coupled thereto (see e.g., FIG. 20). In this manner, the port 654 and the puncture member 653 can define at least a portion of a fluid flow path between the patient and the inner volume of the housing 610, the first fluid reservoir 660, and/or the second fluid reservoir 670, as further described herein.

The actuator mechanism 620 of the transfer device 605 is at least partially disposed within the inner volume of the housing 610 and is movable between a first position (e.g., a distal position relative to the housing 610) and a second position (e.g., a proximal position relative to the housing 610). The movement of the actuator mechanism 620 relative to the housing 610 can transition the device 605 between at least a first configuration (FIG. 20), a second configuration (FIG. 21), and a third configuration (FIG. 22), as further described herein.

As shown, the actuator mechanism 620 includes a first member 621 and a second member 631. The first member 621 of the actuator mechanism 620 can be any suitable shape, size, and/or configuration. For example, in some embodiments, the first member 621 can be substantially similar in form and/or function to the first member 221 of the transfer device 220 and thus, similar aspects are not described in further detail herein. As shown, for example, in FIG. 20, the first member 621 includes a proximal end portion 622 and a distal end portion 623 and defines an inner volume therebetween configured to define at least a portion of the first reservoir 660, as further described herein. The proximal end portion 622 of the first member 621 is open and configured to receive at least a portion of the second member 631 therethrough. The distal end portion 623 of the first member 621 includes a plunger 627. The plunger 627 is configured to form a friction fit with the inner surface of the housing 610 that defines the inner volume to collectively define a fluidic seal therebetween. The plunger 627 defines a channel 628 that receives and/or includes a valve 630, as described above, for example, with reference to the first member 221 of the transfer device 200.

The second member 631 of the actuator mechanism 620 includes a proximal end portion 632 and a distal end portion 633. The proximal end portion 632 can be any suitable shape, size, and/or configuration. For example, in some embodiments, the proximal end portion 632 can have a size and/or shape that allows a user to engage the proximal end portion 632 to move the second member 631 relative to the first member 621. The distal end portion 633 of the second member 631 includes a plunger 637 configured to form a friction fit with an inner surface of the first member 621 defining the inner volume to collectively define a fluidic seal therebetween.

As described above, at least a portion the second member 631 is configured to be movably disposed within the inner volume of the first member 621. The second member 631 can be movable between a first position (e.g., a distal position) and a second position (e.g., a proximal position) thereby transitioning the actuator mechanism 620 between a first configuration and a second configuration, respectively. The second member 631 includes a protrusion 634 that extends in a radial direction to selectively engage a proximal surface of the first member 621 (see e.g., FIGS. 21 and 22), which in turn, selectively limits a distal movement of the second member 631 relative the first member 621, as described in further detail herein.

Figure 22:
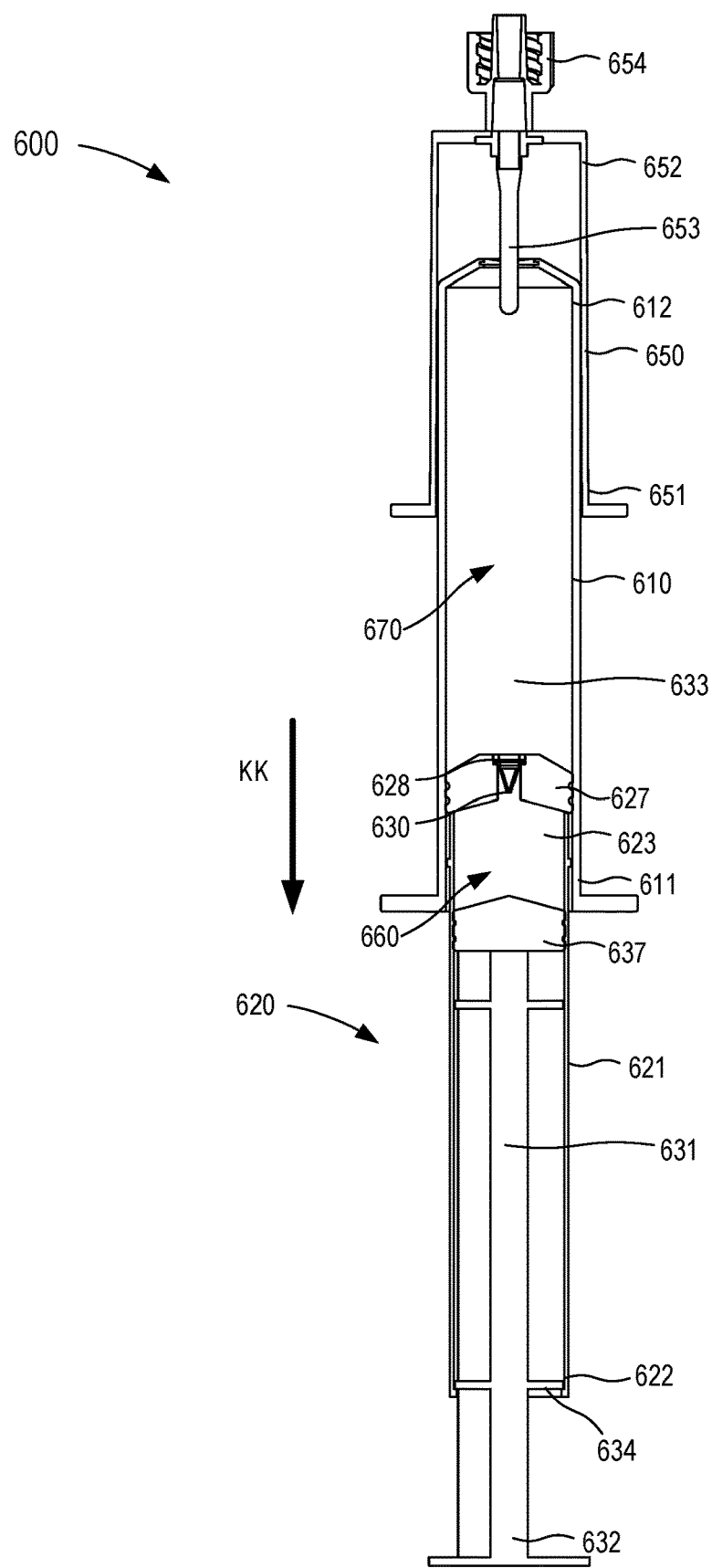
Figure 23:
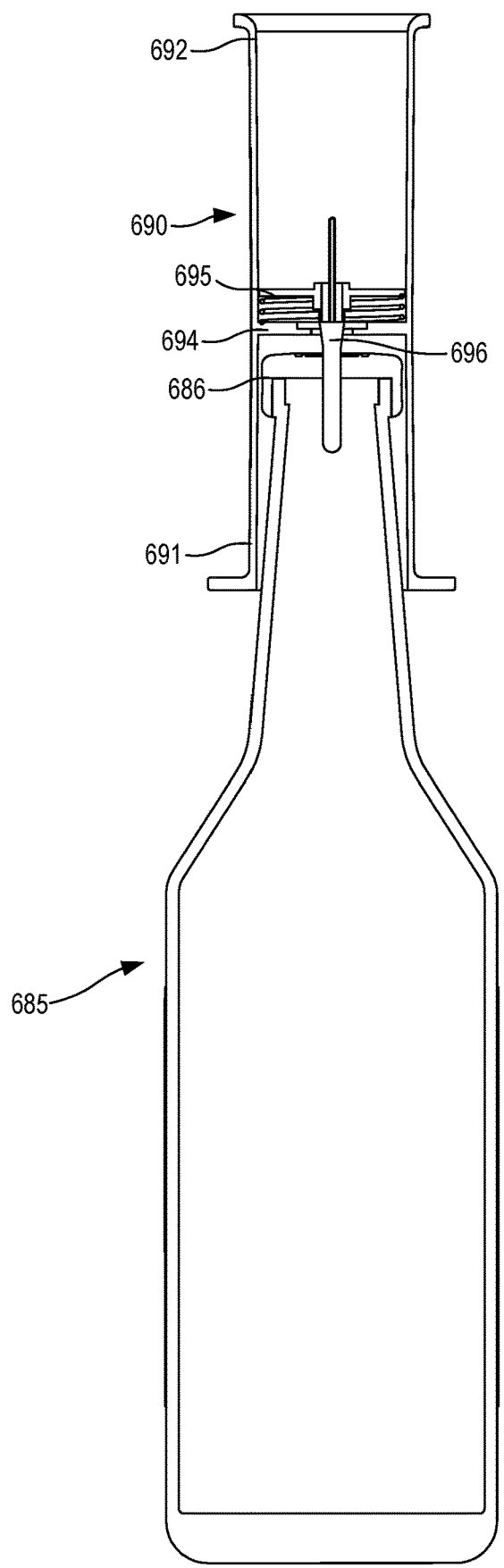
FIGS. 23 and 24 are a cross-sectional view of the syringe-based transfer system of FIG. 18.
Figure 24:
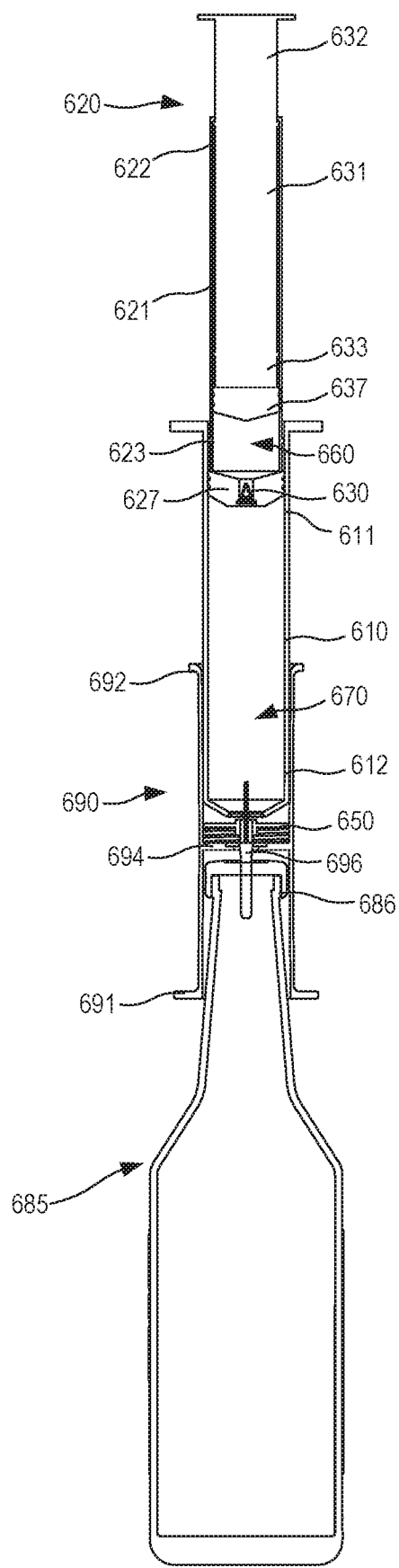
Figure 25:
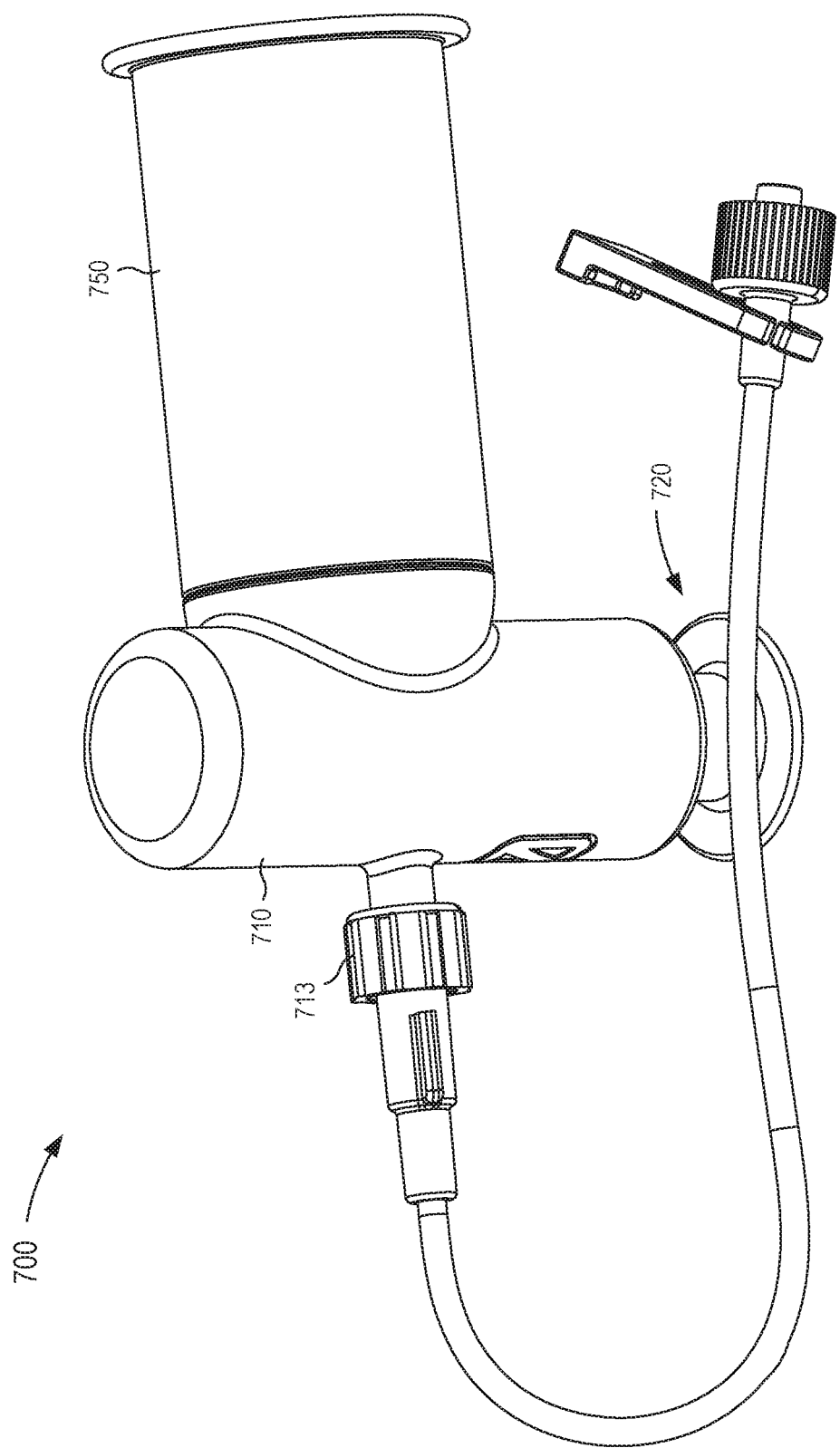
FIG. 25 is a perspective view of a syringe-based transfer device according to another embodiment.

As described in further detail herein, the coupler 690 can be any suitable device configured to establish fluid communication between the transfer device 605 and the external fluid reservoir 685 (see e.g., FIGS. 23 and 24). For example, the coupler 690 includes a first end portion 691 configured to be coupled to the external fluid reservoir 685 and a second end portion 692 configured to be coupled to the transfer device 605. As described in further detail herein, the coupler 690 includes a medial portion 694 coupled to and/or including a puncture member 696. In the embodiment shown in FIGS. 18-24, the puncture member 696 is a double sided puncture member or needle. In other embodiments, the puncture member 696 can have any suitable arrangement. The puncture member 696 is configured to engage a portion of the transfer device 605 and a portion of the external fluid reservoir 685 when the coupler 695 is coupled to the transfer device 605 and the external fluid reservoir 685, thereby fluidically coupling the transfer device 605 to the external fluid reservoir 685, as described in further detail herein.

In use, a user can manipulate the transfer device 605 to couple the adapter 650 to the distal end portion 612 of the housing 610 (see e.g., FIG. 20). Thus, in some embodiments, the puncture member 653 can puncture, pierce, and/or otherwise be inserted through the inlet port 613 to place the puncture member 653 and the port 654 of the adapter 650 in fluid communication with an inner volume defined by the housing 610. In other embodiments, such as the embodiment shown in FIG. 20, the puncture member 653 can extend through the valve 630 disposed within the plunger 627, which in turn, places the puncture member 653 and the port 654 in fluid communication with the inner volume defined by the first member 621 of the actuator mechanism 620 (e.g., the first fluid reservoir 660). Moreover, prior to or after coupling the adapter 650 to the housing 610, a lumen-defining device (see e.g., FIG. 18) coupled to the port 654 can be placed in fluid communication with a portion of a patient (e.g., via a needle, catheter, and/or the like), thereby defining a fluid flow path from the patient, through the lumen-defining device, through the port 654 and the puncture member 653, and into the transfer device 605 (e.g., the first fluid reservoir 660 and/or the second fluid reservoir 670). In other embodiments, the adapter 650 can be coupled to any of the devices described above with reference to the transfer device 200 in FIGS. 2-7.

Figure 21:
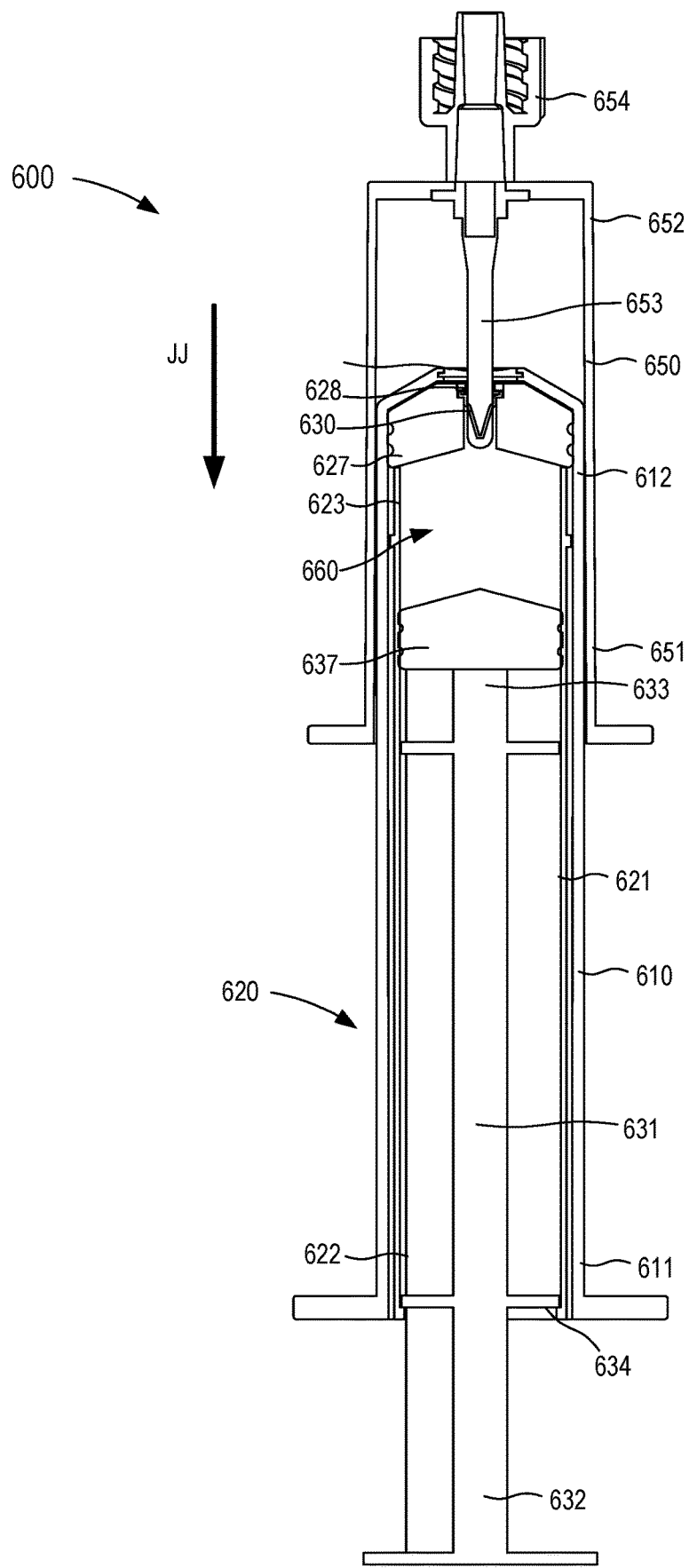

With the fluid communication established between the patient and the transfer device 605, the user can engage the proximal end portion 632 of the second member 631 and can exert a force operable to move the second member 631 relative to the first member 621 and the housing 610, as indicated by the arrow JJ in FIG. 21. The arrangement of the second member 631 within the first member 621 is such that the proximal motion of the second member 631 increases a distance between the plunger 627 of the first member 621 and the plunger 637 of the second member 631. In other words, the movement of the second member 631 relative to the first member 621 increases a volume of the first member 621 defined between the plungers 627 and 637. As described above with reference to the transfer device 200, the increase in the volume is such that the first reservoir 660 is defined between the plungers 627 and 637, as shown in FIG. 21. Furthermore, with the plunger 637 forming a fluid tight seal with the inner surface of the first member 621, the increase of volume produces a negative pressure within the first reservoir 660, which can be sufficient to draw a volume of bodily-fluid through the fluid flow path (described above) and into the first fluid reservoir 660. In some embodiments, the bodily-fluid can contain undesirable microbes such as, for example, dermally-residing microbes and/or other external contaminants (e.g., microbes within a lumen defined by the transfer device 605, microbes within the lumen defined by the lumen defining device, and/or any other undesirable microbe not present in the bodily-fluid source such as the bloodstream), as described above with reference to the transfer device 200.

As the actuator mechanism 620 is transitioned to the second configuration and/or while the actuator mechanism 620 is in the second configuration (see e.g., FIG. 21), the transfer device 605 transfers a desired amount (e.g., a predetermined amount) of bodily-fluid to the first reservoir 660. In some embodiments, the first, predetermined amount can substantially correspond to the size of the first reservoir 660. In other embodiments, the first amount can substantially correspond to an equalization of pressure within the first reservoir 660 and the portion of the patient. Moreover, in such embodiments, the equalization of the pressure can be such that the valve 630 returns to the closed configuration. Thus, the first reservoir 660 is fluidically isolated from a volume substantially outside the first reservoir 660.

With the first amount fluidically isolated within the first fluid reservoir 660, the device 605 can be transitioned from the second configuration (FIG. 21) to the third configuration (FIG. 22) by further manipulating the proximal end portion 632 of the second member 631. For example, a user can continue to exert a force on the proximal end portion 632 of the second member 631 to move the second member 631 to a third position, as indicated by the arrow KK in FIG. 22. As shown, the first member 621 is configured to move with the second member 631 as the second member 631 is moved from the first position to the second position. More specifically, once the protrusions 634 of the second member 631 are placed in contact with the portion of the first member 621, any further movement of the second member 631 in the proximal direction results in a similar movement of the first member 621 in the proximal direction (see e.g., FIGS. 21 and 22). In some embodiments, the movement of the second member 631 and the first member 621 can be substantially continuous. That is to say, the second member 631 can be moved from the first position through the second position and to the third position in a substantially smooth and/or continuous manner. In other instances, the second member 631 can be moved from the first position to the second position in a first movement and the second member 631 can be moved from the second position to the third position in a second movement discreet or non-continuous with the first movement.

As described above with reference to the second member 631, the movement of the first member 621 within the housing 610 results in an increased volume within the housing 610 that is distal to the plunger 627 of the first member 621, thereby defining the second reservoir 670, as shown in FIG. 22. Furthermore, with the plunger 627 forming a fluid tight seal with the inner surface of the housing 610 and with the valve 630 in the closed configuration, the increase of volume produce a negative pressure within the second reservoir 670 that is sufficient to draw a volume of bodily-fluid from the patient, through the fluid flow path, and into the second reservoir 670. In addition, by fluidically isolating the first reservoir 660, the bodily-fluid contained within the second reservoir 670 is substantially free from microbes generally found outside of the portion of the patient (as described above). As described in detail above with reference to the transfer device 200, in some instances, the user can visualize and/or otherwise quantify the volume of the bodily-fluid disposed in the second reservoir 670 via an indication portion of the housing 610 and/or the like. Thus, the user can withdraw a bodily-fluid from the patient until a desired volume of the bodily-fluid is disposed in the second reservoir 670, as described in detail above with reference to the transfer device 200.

After the desired volume of bodily-fluid is disposed in the second reservoir 670, the transfer device 605 can be transitioned from the third configuration to a fourth configuration. For example, as shown in FIGS. 23 and 24, the user can manipulate the coupler 690 by disposing a first end portion 691 of the coupler 690 about the external fluid reservoir 685. More specifically, the coupler 690 is coupled to the external fluid reservoir 685 such that a first side of the puncture member 696 punctures, pierces, breaks, opens, and/or otherwise moves through a port 686 of the external fluid reservoir 685 to be placed in fluid communication with an inner volume thereof. For example, referring back to FIG. 18, the external fluid reservoir 685 can include a cap, a top, and/or any suitable closure means. The cap, for example, can include and/or define the port 686. In some embodiments, the port 686 can be a seal, a membrane, a frangible seal, a self-healing port, and/or any other suitable port.

With the first end portion of the puncture member 696 in fluid communication with the external fluid reservoir 685, the user can manipulate the transfer device 605 by inserting a portion of the transfer device 605 the second end portion 692 of the coupler 690. In this manner, a second side of the puncture member 696 opposite the first side can puncture, pierce, open, and/or otherwise move through the port 613 included in the housing 610, which in turn, places the puncture member 696 in fluid communication with the second fluid reservoir 670 defined by a portion of the inner volume of the housing 610 that is distal to the plunger 627 of the first member 621 of the actuator mechanism 620, as shown in FIG. 24. Thus, the puncture member 696 establishes fluid communication between the second fluid reservoir 670 and an inner volume of the external fluid reservoir 685 (e.g., a vile, a test tube, a petri dish, a test apparatus, a cartridge designed for use with an automated, rapid microbial detection system, an evacuated container or microcontainer, and/or any other suitable reservoir). With fluid communication established between the transfer device 605 and the external fluid reservoir 685, the user can exert a force on the proximal end portion 632 of the second member 631 that is operable in moving the second member 631 and the first member 621 in the distal direction such that at least a portion of the volume of bodily-fluid can be transferred from the second reservoir 670 to the external fluid reservoir 685, as described above with reference to the transfer device 200. For example, the bodily-fluid can be expelled from the second fluid reservoir 670 to be used for any number of testing processes or procedures such as, for example, blood culture testing, real-time diagnostics, and/or PCR-based approaches, while minimizing false results that might otherwise result from undesirable microbes or the like.

While the transfer devices 200, 300, 400, 500, and 605 are shown and described above as including actuator mechanisms 220, 320, 420, 520, and 620, respectively, configured to move along a single axis (e.g., in a proximal and/or a distal direction), in other embodiments, a fluid transfer device can include one or more members configured to move along at least two different axes. For example, FIGS. 25-29 illustrate a fluid transfer device 700 according to an embodiment.

As shown, the transfer device 700 includes a housing 710, an actuator mechanism 720, and an adapter 750, and includes and/or defines a first fluid reservoir 760 and a second fluid reservoir 770. The housing 710 of the transfer device 700 can be any suitable shape, size, or configuration. For example, the housing 710 includes an actuator portion 788 and an adapter portion 789. The actuator portion 788 of the housing 710 is substantially open at one end and is configured to movably receive the actuator mechanism 720 (see e.g., FIGS. 27-29). In other words, the actuator portion 788 of the housing 710 can form a first bore or the like with one open side and one closed side.

The actuator portion 788 of the housing 710 includes an inlet port 713 that is in selective fluid communication with one or more portions of the housing 710 (e.g., the first fluid reservoir 760 and/or the second fluid reservoir 770), as described in further detail herein. The port 713 can be any suitable port. For example, in some embodiments, the port 713 is substantially similar to the port 213 described above with reference to the transfer device 200. As such, the port 713 is configured to physically and fluidically couple to a lumen-defining device such as a needle and/or cannula to be placed in fluid communication with a portion of a patient, as described in detail above with reference to the transfer device 200.

Figure 27:
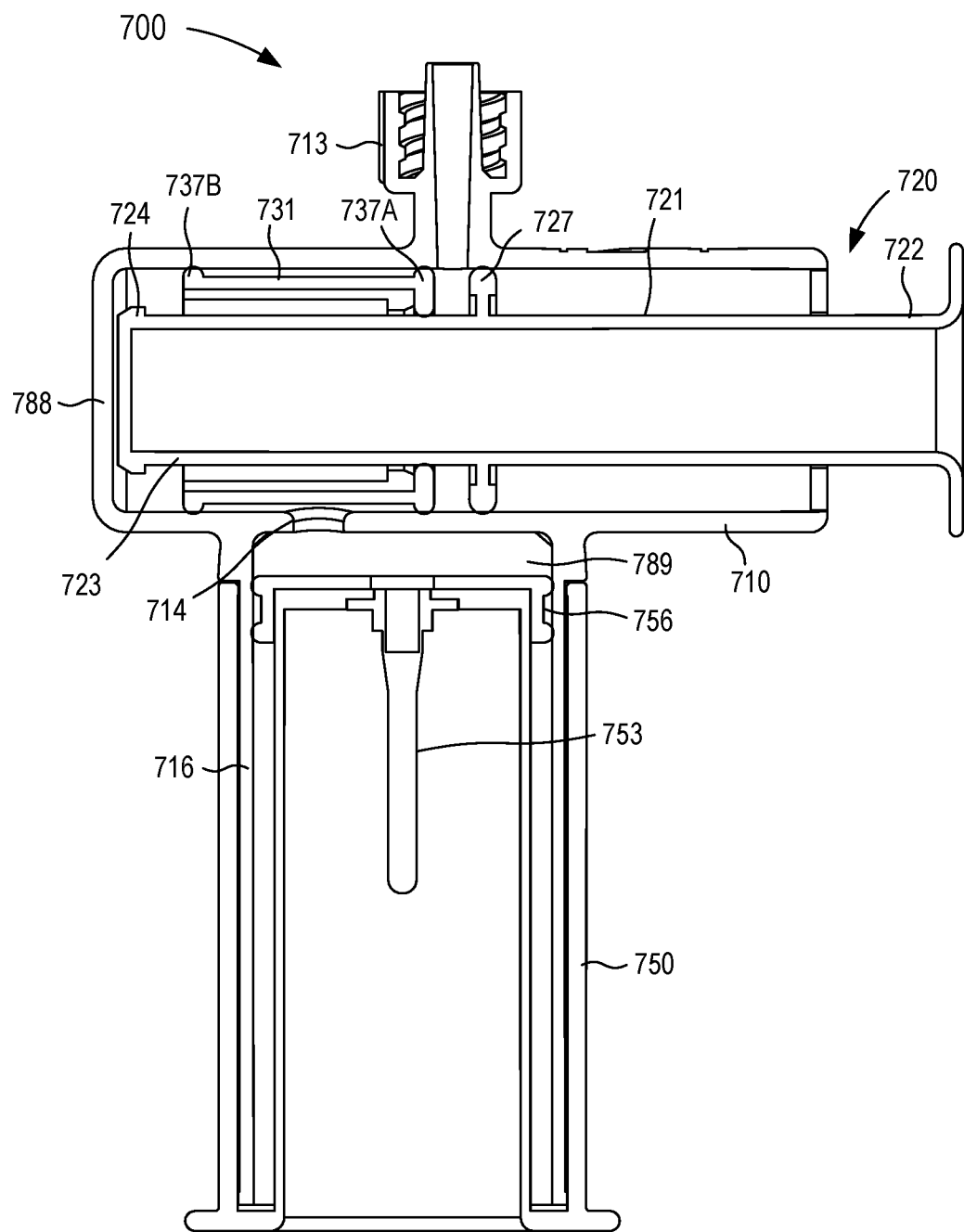
FIGS. 27-29 are cross-sectional view of the syringe-based transfer device and the transfer adapter taken along the line $X_6$-$X_6$, in a first configuration, a second configuration, and a third configuration, respectively.
Figure 28:
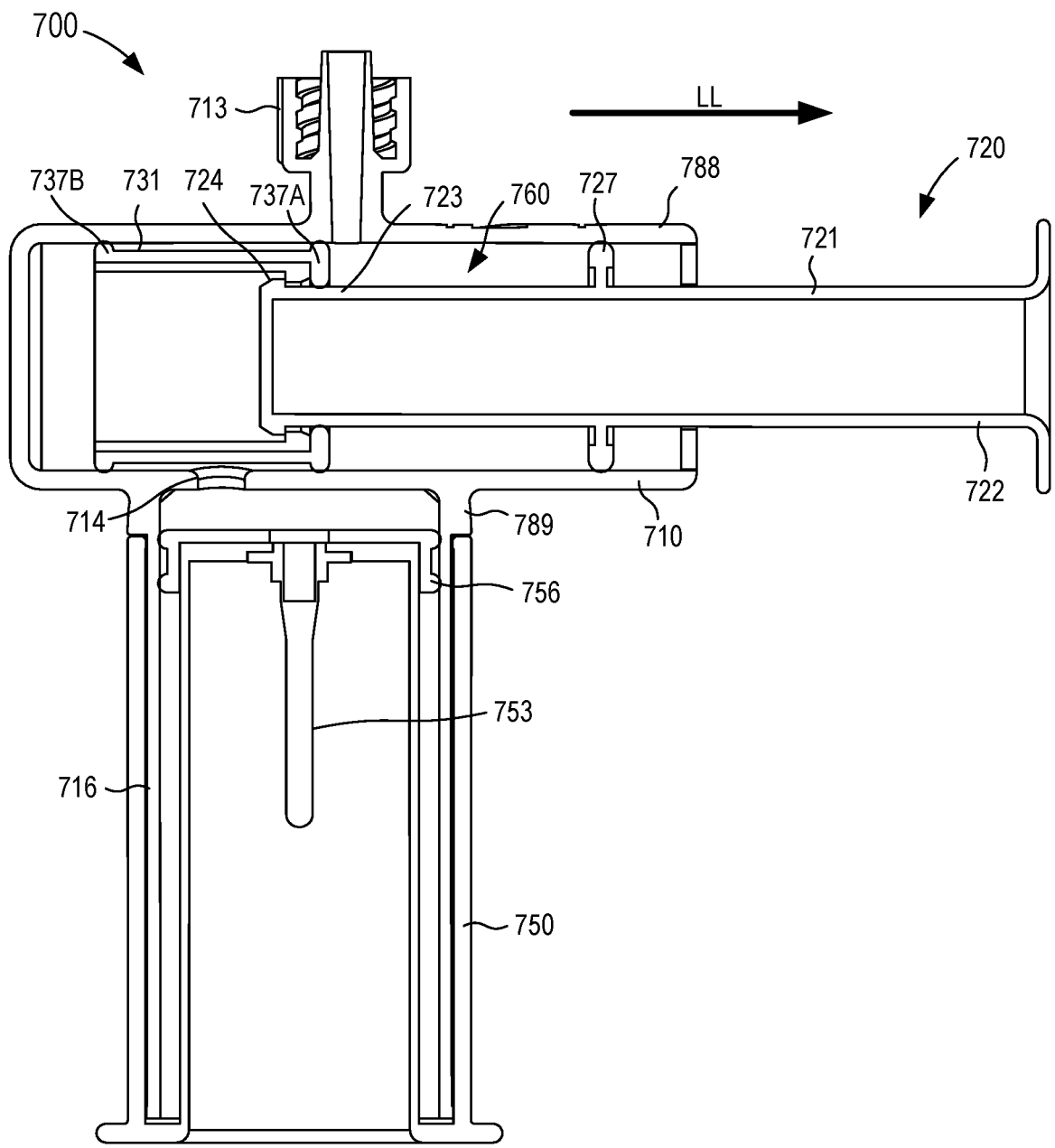
Figure 29:
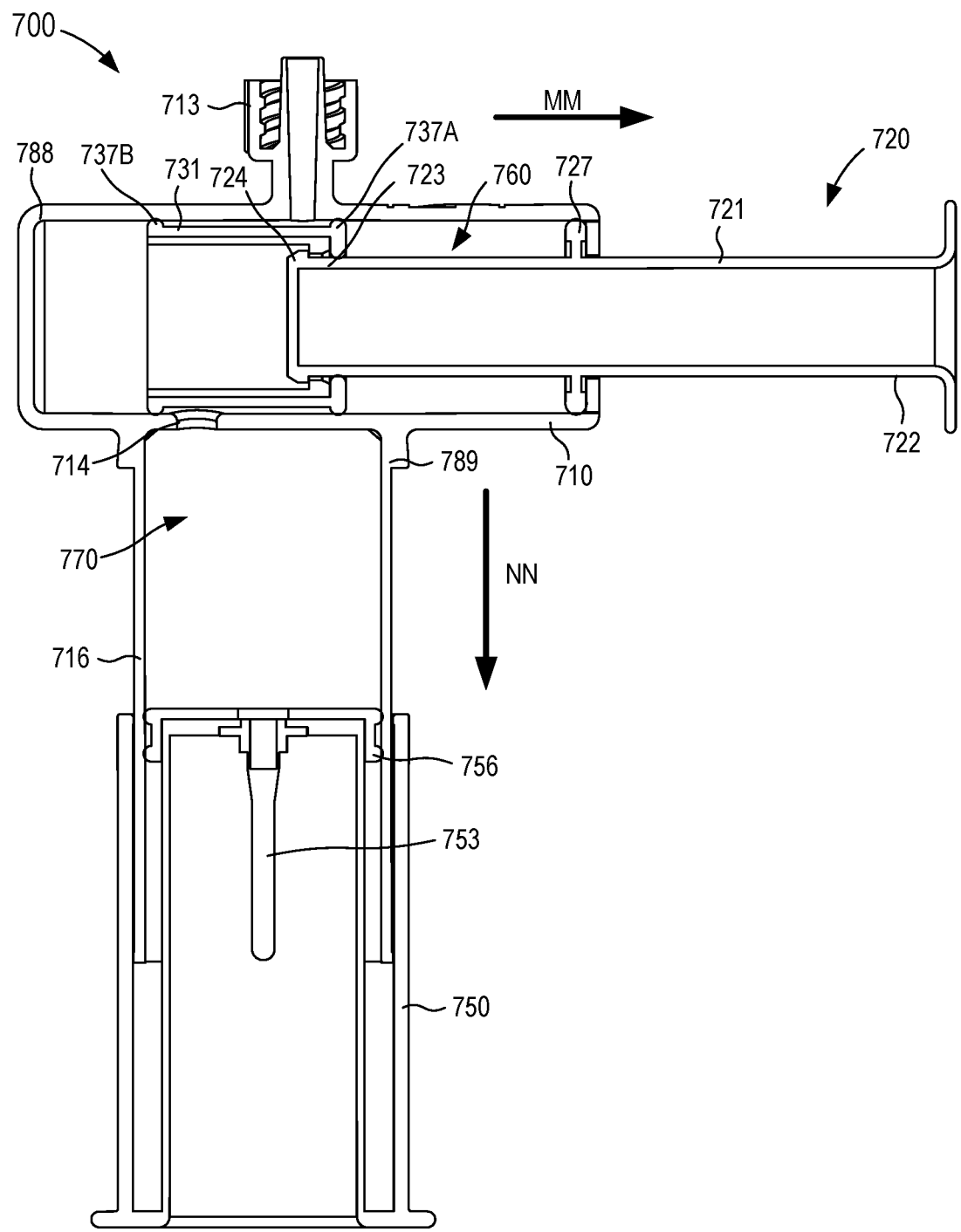

The adapter portion 789 of the housing 710 is coupled to the actuator portion 788 and is arranged in a transverse or substantially perpendicular orientation relative to the actuator portion 788. As shown, for example, in FIG. 27, the adapter portion 789 is in fluid communication with a portion of the actuator portion 788 via an opening 714 (an outlet port or the like) in a wall of the housing 710 otherwise isolating the actuator portion 788 from the adapter portion 789. The adapter portion 789 is configured to movably engage the adapter 750. For example, as shown in FIG. 27, the adapter portion 789 is substantially cylindrical having an annular set of walls that define an inner volume. The annular walls of the adapter portion 789 are movably disposed within a portion of the adapter 750. In other words, the adapter 750 is movably coupled to the adapter portion 789 such that a first portion of the adapter 750 is disposed within the adapter portion 789 and a second portion is disposed outside of the adapter portion 789, as shown in FIGS. 27-29. As described above with reference to the housing 210 of the transfer device 200, the adapter portion 789 includes an indicator portion 716 that is configured to provide an indication of a volume of bodily-fluid disposed within the adapter portion 789. The arrangement of the adapter 750 is such that a surface of the adapter 750 can be placed in a position relative to the indicator portion 716 that is indicative of a volume of bodily-fluid transferred into the adapter portion 789 (e.g., the second reservoir 770), as described in further detail herein.

The actuator mechanism 720 of the transfer device 700 is at least partially disposed within an inner volume of the actuator portion 788 of the housing 710. The actuator mechanism 720 is movable between a first position (e.g., a distal position relative to the housing 710) and a second position (e.g., a proximal position relative to the housing 710) within the actuator portion 788. The movement of the actuator mechanism 720 relative to the housing 710 can transition the device 700 between at least a first configuration (FIG. 27) and second configuration (FIG. 28), as further described herein.

As shown, the actuator mechanism 720 includes a first member 721 and a second member 731. The first member 721 of the actuator mechanism 720 can be any suitable shape, size, and/or configuration. For example, in the embodiment shown in FIGS. 25-29, the first member 721 is substantially cylindrical having a proximal end portion 722 and a distal end portion 723. The proximal end portion 722 is disposed outside of the actuator portion 788 of the housing 710 and is configured to be engaged and/or manipulated by a user to move the first member 721 within the actuator portion 788. The distal end portion 723 is disposed within the actuator portion 788 of the housing 710. The distal end portion 723 includes and/or forms a protrusion 724 configured to selectively engage a portion of the second member 731, as described in further detail herein.

Figure 26:
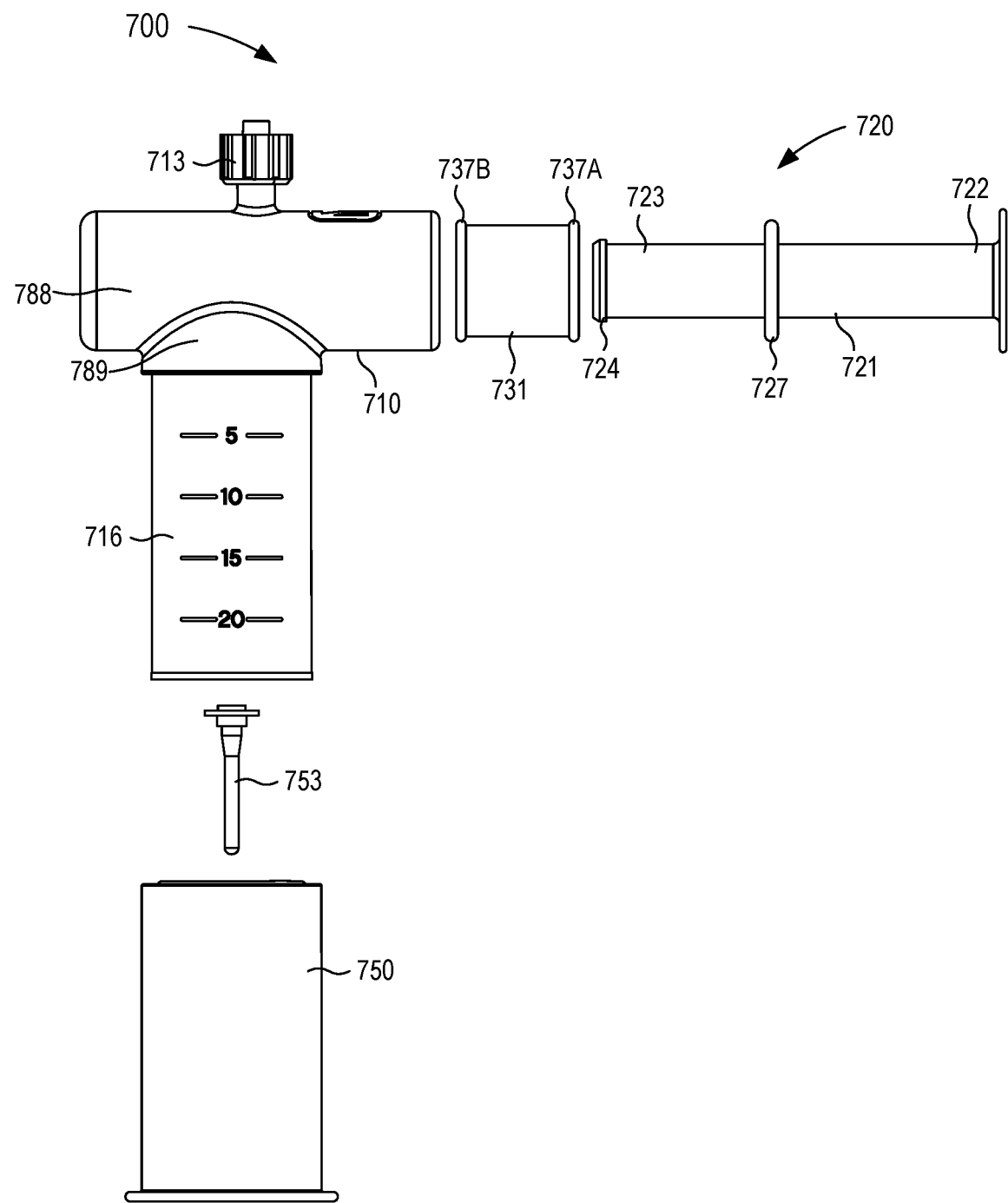
FIG. 26 is an exploded view of a syringe-based transfer device and a transfer adapter included in the syringe-based transfer system of FIG. 25.

As shown in FIGS. 26 and 27, the first member 721 further includes a plunger 727 disposed along a length of the first member 721. For example, in some embodiments, the plunger 727 can be positioned along the length of the first member 721 such that the plunger 727 remains between a lumen defined by the inlet port 713 and the open end of the actuator portion 788. That is to say, the plunger 727 remains on a single side of the lumen of the inlet port 713 when the first member 721 is moved within the actuator portion 788 between the first position and the second position. Furthermore, the plunger 727 is configured to engage an inner surface of the actuator portion 788 to form a substantially fluid tight seal therebetween. In this manner, the plunger 727 forms a portion of the first fluid reservoir 760 when the first member 721 is in the second position (FIG. 28), as described in further detail herein.

The second member 731 of the actuator mechanism 720 is movably disposed about the first member 721, as shown in FIGS. 27-29. More particularly, the second member 731 is disposed about the first member 721 such that the plunger 727 is disposed between the second member 731 and the proximal end portion 722 of the first member 721. The second member 731 can be any suitable shape, size, and/or configuration. For example, as shown in FIG. 27, the second member 731 includes a first plunger 737A disposed on a first end portion of the second member 731 and a second plunger 737B disposed on a second end portion of the second member 731. The arrangement of the second member 731 and the plungers 737A and 737B is such that a diameter of the plungers 737A and 737B is greater than a diameter of the second member 731. Thus, an annular channel or the like is defined by the inner surface of the actuator portion 788 and an outer surface of the first member 721 between the plungers 737A and 737B. Furthermore, a portion of the plunger 737A is configured to engage the outer surface of the first member 721 to form a substantially fluid tight seal therebetween. Thus, in the embodiment shown in FIGS. 25-29, the annular channel or the like is fluidically isolated from a volume outside of the plungers 737A and 737B unless and/or until the second member 731 is moved to a position in which the annular channel or the like is in fluid communication with the inlet port 713 and/or the opening 714.

The adapter 750 can be any suitable shape, size, and/or configuration. As described above, the adapter 750 includes a first portion that is movably disposed within the adapter portion 789 of the housing 710 and a second portion that is movably disposed about an outer surface of the adapter portion 789. The portion of the adapter 750 disposed within the adapter portion 789 of the housing 710 includes and/or is coupled to a plunger 756 configured to engage an inner surface of the adapter portion 789 to form a substantially fluid tight seal therebetween. In this manner, the plunger 756 and the adapter portion 789 collectively define the second fluid reservoir 770. As shown in FIG. 27, the plunger 756 is coupled to a puncture member 753 such as a sheathed needle or the like. As described above with reference to the transfer system 600, the puncture member 753 can be configured to puncture, pierce, open, and/or otherwise move through a seal or port of an external fluid reservoir to place the second fluid reservoir 770 in fluid communication with the external fluid reservoir (not shown). Although not shown in FIGS. 25-29, in some embodiments, the adapter 750 can include a valve or seal configured to selectively control a flow of fluid through the puncture member 753. For example, in some embodiments, the valve or seal can be in a substantially closed or sealed configuration until a pressure differential is exerted on the valve and/or seal sufficient to transition the valve and/or seal to an open configuration.

In use, a user (e.g., a phlebotomist, a nurse, a technician, a physician, or the like) can engage the transfer device 700 to couple the inlet port 713 to a proximal end portion of a lumen-defining device (not shown) such as, for example, a butterfly needle, a cannula assembly, any of the devices described above with reference to the transfer device 200 in FIGS. 2-7, etc. The distal end portion of the lumen-defining device can be inserted into and/or can be previously disposed within a portion of the body of a patient (e.g., a vein). Thus, the inlet port 713 is placed in fluid communication with the portion of the body and can transition the transfer device 700 from the first configuration (see e.g., FIG. 27) to the second configuration (see e.g., FIG. 28).

For example, the user can exert a force on the proximal end portion 722 of the first member 721 that is operable to move the first member 721 relative to the actuator portion 788 of the housing 710, as indicated by the arrow LL in FIG. 28. As described above with reference to the transfer device 200, the proximal motion of the first member 721 increases a distance between the plunger 727 of the first member 721 and the plunger 737A of the second member 731. In other words, the first member 721 is moved relative to the second member 731 such that a distance and/or volume defined between the plungers 727 and 737A is increased. This increase in the volume, in turn, establishes and/or defines the first fluid reservoir 760 between the plungers 727 and 737A, as shown in FIG. 28. Furthermore, with the plungers 727 and 737A forming a fluid tight seal with the inner surface of the actuator portion 788 of the housing 710, the increase in volume therebetween produces a negative pressure within the first reservoir 760, which can be sufficient to draw a volume of bodily-fluid from the patient, through the fluid flow path (described above), and into the first fluid reservoir 760. In some embodiments, the bodily-fluid can contain undesirable microbes such as, for example, dermally-residing microbes and/or other external contaminants (e.g., microbes within a lumen defined by the transfer device 700, microbes within the lumen defined by the lumen defining device, and/or any other undesirable microbe not present in the bodily-fluid source such as the bloodstream), as described above with reference to the transfer device 200.

With the first amount of bodily-fluid contained in the first fluid reservoir 760, the user can transition the device 700 from the second configuration (FIG. 28) to the third configuration (FIG. 29) by continuing to exert the force and/or exerting an additional force on the proximal end portion 722 of the first member 721, which in turn, moves the first member 721 to a third position, as indicated by the arrow MM in FIG. 29. As shown, the second member 731 is configured to move with the first member 721 as the first member 721 is moved from the second position to the third position. For example, once the protrusion(s) 724 of the first member 721 are placed in contact with a portion of the second member 731, any further movement of the first member 721 in the proximal direction results in a similar movement of the second member 731 in the proximal direction (see e.g., FIGS. 28 and 29). The movement of the first member 721 and the second member 731 can be substantially continuous or can be non-continuous, as described above with reference to the transfer device 400.

As shown in FIG. 29, the movement of the second member 731 within the actuator portion 788 of the housing 710 results in a position of the plungers 737A and 737B being changed, for example, relative to the inlet port 713. For example, each of the plungers 737A and 737B can be disposed on the same side of the inlet port 713 prior to the second member 731 being moved (see e.g., FIGS. 27 and 28). Once the second member 731 is moved in response to the first member 721 being placed in the third position, the plunger 737A can be disposed one a first side of the inlet and the plunger 737B can be disposed on a second side of the inlet port 713 opposite the first side (FIG. 29). Thus, moving the second member 731 in the MM direction, as shown in FIG. 29, places the inlet port 713 in fluid communication with the annular volume defined between the plungers 737A and 737B. Moreover, the second member 731 can be moved to a position in which the opening 714 is also in fluid communication with the annular volume defined between the plungers 737A and 737B. In this manner, placing the first member 721 in the third position moves the second member 731 such that the annular volume defined between the plungers 737A and 737B fluidically couples the inlet port 713 to the opening 714.

With fluid communication established between the inlet port 713 and the opening 714, the user can manipulate the adapter 750 by moving the adapter 750 relative to the adapter portion 789 of the housing 710, as indicated by the arrow NN in FIG. 29. As a result, the plunger 756 of the adapter 750 is moved within the adapter portion 789 such that the adapter portion 789 and the plunger 756 collectively define the second fluid reservoir 770. Furthermore, the movement of the plunger 756 produces a negative pressure within the second fluid reservoir 770 (as described above) that is operable in drawing a volume of bodily-fluid from the patient into the second fluid reservoir 770 (e.g., via the inlet port 713, the annular volume defined between the plungers 737A and 737B, and the opening 714). By fluidically isolating the first reservoir 760, the bodily-fluid contained within the second reservoir 770 is substantially free from microbes generally found outside of the portion of the patient (as described above).

As described in detail above with reference to the transfer device 200, in some instances, the user can visualize and/or otherwise quantify the volume of the bodily-fluid disposed in the second reservoir 770 via the indicator portion 716 of the housing 710. For example, moving the adapter 750 relative to the adapter portion 789 results in a movement of a surface of the adapter 750 relative to the indicator portion 716. In some embodiments, the position of the surface along the indicator portion 716 is such that the surface is aligned with an indicator and/or indicia (e.g., a tick mark, a number, and/or the like) that provides the user with an indication of the volume of bodily-fluid within the second fluid reservoir 770. In some instances, the arrangement of the adapter 750 and the indicator portion 716 can be such that the user can draw a volume of bodily-fluid into the second fluid reservoir 770 that is within a desired tolerance. For example, the tolerance can be a tolerance associated with a desired volume of bodily-fluid to be used with a given culture medium and/or test. In this manner, the user can mitigate a risk of false positive or false negative results associated with providing a volume of bodily-fluid that is outside of a desired tolerance for a give use (e.g., sample, test, assay, culture, etc.).

After the desired volume of bodily-fluid is disposed in the second reservoir 770, the user can insert at least a portion of an external fluid reservoir (not shown) into the adapter 750 such that the puncture member 753 punctures, pierces, breaks, opens, and/or otherwise moves through a port or seal of the external fluid reservoir, as described above with reference to the transfer system 600. As such, the puncture member 753 can establish fluid communication between the second fluid reservoir 770 and the external fluid reservoir. For example, in some embodiments, the external fluid reservoir can define a negative pressure or the like that can be operable in transitioning a valve or seal of the puncture from a closed configuration to an open configuration. In other embodiments, the user can remove a cap and/or seal from the puncture member 753 prior to inserting the puncture member 753 into the external fluid reservoir. In still other embodiments, inserting the puncture member 753 into the external fluid reservoir can automatically remove a cap, seal, and/or any other obstruction. Thus, with fluid communication established between the second fluid reservoir 770 and the external fluid reservoir 785, at least a portion of the bodily-fluid contained in the second fluid reservoir 770 can be transferred into the external fluid reservoir.

Although not shown in FIG. 29, in some embodiments, the opening 714 can be fluidically isolated from the inlet port 713 prior to establishing fluid communication between the second fluid reservoir 770 and an external fluid reservoir. In some instances, for example, such an arrangement can limit and/or can substantially prevent a negative pressure within the external fluid reservoir from drawing additional bodily-fluid through the opening 714 an into the second fluid reservoir 770, which may otherwise result in an inaccurate measurement of the volume of bodily-fluid that is transferred to the external fluid reservoir. In this manner, the user can mitigate a risk of false positive or false negative results associated with providing a volume of bodily-fluid that is outside of a desired tolerance for a give use (e.g., sample, test, assay, culture, etc.).

Figure 30:
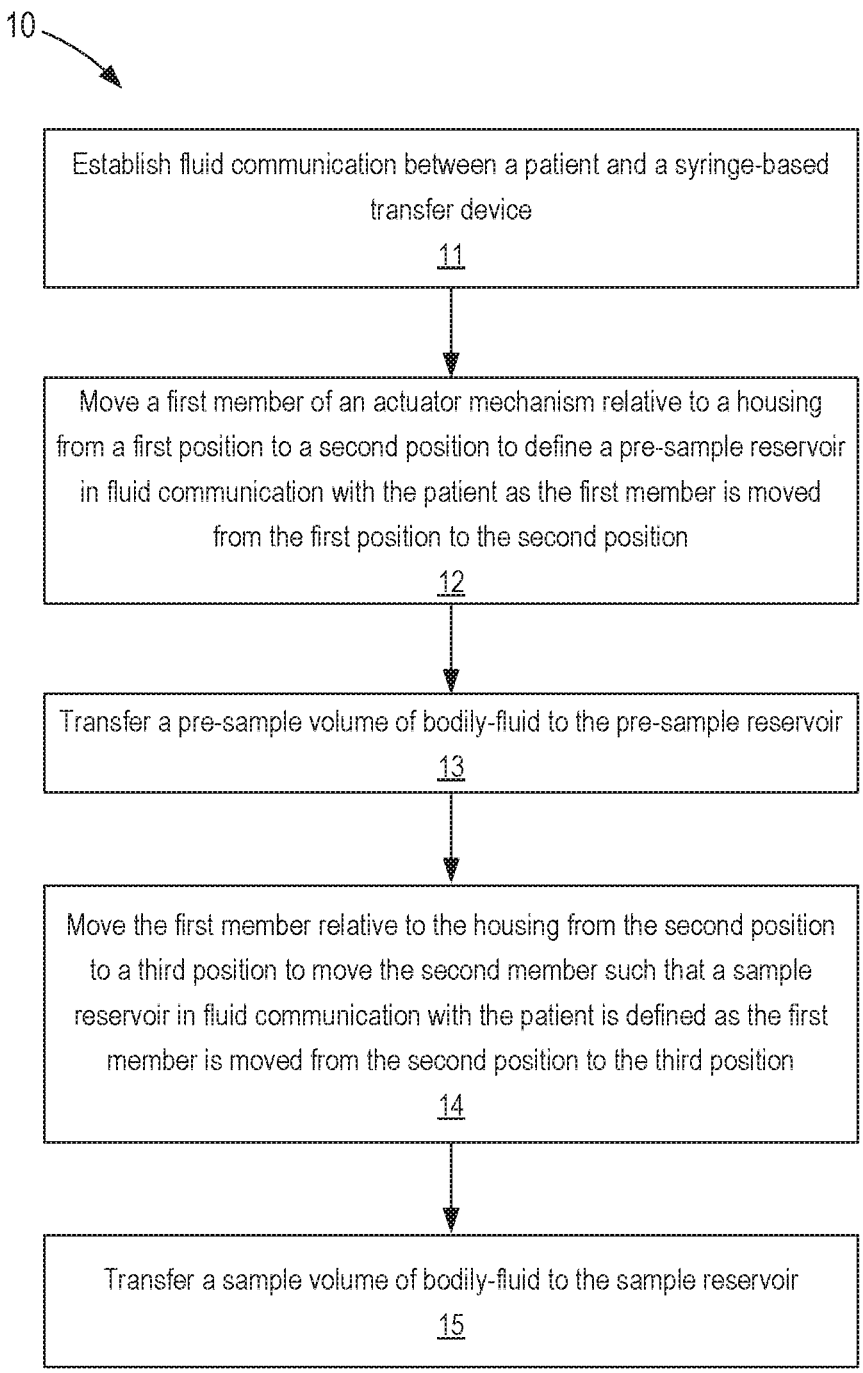
FIG. 30 is a flowchart illustrating a method of using a syringe-based fluid transfer device according to an embodiment.

FIG. 30 is a flowchart illustrating a method 10 of using a syringe-based fluid transfer device according to an embodiment. The method 10 includes establishing fluid communication between a patient and the syringe-based transfer device, at 11. The syringe-based transfer device can be any of the transfer device described herein (e.g., the transfer devices 100, 200, 300, 400, 500, 605, and/or 700). For example, the syringe-based transfer device (also referred to herein as "transfer device") can include at least a housing and an actuator mechanism. At least a portion of the actuator mechanism is movably disposed within the housing. As described above with reference to the transfer devices, the actuator mechanism can include a first member and a second member that can be moved collectively or independently to transfer fluid to or from the transfer device.

For example, in some embodiments, the method 30 includes moving a first member of the actuator mechanism relative to the housing from a first position to a second position to define a pre-sample reservoir in fluid communication with the patient as the first member is moved from the first position to the second position, at 12. The pre-sample reservoir can be in fluid communication with the patient via any suitable structure and/or means, such as those described herein. For example, in some embodiments, the transfer device can be coupled to an adapter that includes a puncture member. As described above with reference to the transfer device 605, in such embodiments, the adapter can be in fluid communication with the patient and the puncture member can be at least partially disposed within and/or otherwise in fluid communication with the pre-sample reservoir.

In some embodiments, a portion of the first member can be movably disposed within the second member such that the first member and the second member collectively define the pre-sample reservoir. As described above in the specific embodiments, the first member and/or the second member can include one or more plungers configured to contact a surface to form a substantially fluid tight seal. For example, in some embodiments, the first member can include a plunger configured to contact an inner surface of the second member to define a substantially fluid tight seal therebetween. Therefore, the movement of the first member can increase a volume disposed between a portion of the second member and the plunger of the first member, which in turn, can produce a negative pressure therein, as described in detail above with reference to, for example, the transfer device 200.

As the first member is moved from the first position to the second position and/or after the first member is placed in the second position, a pre-sample volume of bodily-fluid is transferred to the pre-sample reservoir, at 13. The pre-sample volume of bodily-fluid can be any suitable volume. For example, in some instances, the pre-sample volume of bodily-fluid can be a volume substantially equal to a volume of the pre-sample reservoir. In other embodiments, bodily-fluid can be transferred into the pre-sample reservoir until a pressure differential is equalized or the like. In some instances, the pre-sample volume of bodily-fluid can contain contaminants such as dermally-residing microbes or the like, as described above.

After transferring the pre-sample volume of bodily-fluid into the pre-sample reservoir, the first member is moved relative to the housing from the second position t to a third position to move the second member such that a sample reservoir in fluid communication with the patient is defined as the first member is moved from the second position to the third position, at 14. For example, a puncture member of an adapter (as described above) can be fluidically isolated from the pre-sample reservoir and placed in fluid communication with the sample reservoir as the first member is moved from the second position to the third position. The second member is moved by the first member when the first member moves from the second position to the third position. For example, in some embodiments, placing the first member in the second position can place one or more protrusions of the first member in contact with a portion of the second member such that further movement of the first member results in a concurrent movement of the second member, as described above. In some embodiments, the movement of the second member is such that the second member and a portion of the housing collectively defining the sample reservoir. For example, in some embodiments, the second member can include a plunger or the like configured to form a substantially fluid tight seal with an inner surface of the housing, thereby defining at least a portion of the sample reservoir.

As the first member is moved from the second position to the third position and/or after the first member is placed in the third position, a sample volume of bodily-fluid is transferred to the sample reservoir, at 15. As described in detail above with reference to specific embodiments, in some instances, the sample volume can be, for example, a predetermined volume of bodily-fluid that is based on, for example, the type of test that will be used to analyze the bodily-fluid. In some instances, the sample volume can be monitored and/or verified via an indicator portion of the housing and/or any other suitable means for verifying a sample volume. Thus, as described in detail above, the syringe-based transfer device can be used to transfer a desired volume of bodily-fluid from a patient to a sample reservoir and/or testing device. Moreover, the use of the method 10 and/or any of the transfer devices 100, 200, 300, 400, 500, 605, and/or 700 described herein can result in a volume of bodily-fluid having a volume within a given tolerance of a state and/or desired value and with reduced contamination.

While various embodiments have been particularly shown and described above, it should be understood that they have been presented by way of example only, and not limitation. Although various embodiments have been described as having particular features and/or combinations of components, other embodiments are possible having any combination or sub-combination of any features and/or components from any of the embodiments described herein and/or from any of the alternatives presented herein. For example, while the adapters 250 and 750 are not shown and/or described above as including a sterilization member or the like, in other embodiments, the adapters 250 and/or 750 can include any suitable sterilization member such as, for example, the sterilization member(s) 380 included in the adapter 350 described above with reference to FIGS. 9 and 10. Moreover, while the adapters 250, 350, 650, and 750, as well as the coupler 690 are shown and described above as including a puncture member that establishes fluid communication with an external fluid reservoir (see e.g., FIG. 24 with reference to the coupler 690), in other embodiments, an adapter and/or a housing of a transfer device can be configured to establish fluid communication with an external fluid reservoir in any suitable manner. For example, in some embodiments, fluid communication can be established via a heparin lock, a saline lock, a Luer Lok®, a selective seal, valve, or membrane, a selective engagement configured to remove an obstruction (e.g., a cap or the like), and/or any other suitable means of establishing fluid communication. Thus, while the embodiments described above refer to and/or otherwise show a puncture member, it should be understood that the means of establishing fluid communication is not limited thereto.

While the transfer device 200 is particularly shown in FIGS. 2-7, in other embodiments, a transfer device can be substantially similar to those described in U.S. Pat. No. 9,155,495 incorporated by reference above. Expanding further, while the transfer device 200 is shown and described above as having the actuator mechanism 220 that defines the first reservoir 260 within which a first volume of bodily-fluid is isolated, in other embodiments, a transfer device can include any suitable means for diverting and isolating a first volume of bodily-fluid such as those described in the U.S. Pat. No. 9,155,495.

As another example, although the embodiments have been particularly shown and described herein as being actuated by a user, in other embodiments, a transfer device can be actuated automatically or at least partially automatically. For example, in some embodiments, a transfer device can include an energy storage member such as a spring, a coil, a compressed gas storage member, a chemical energy storage (e.g., a battery or the like), and/or any other suitable device configured to actuate at least a portion of the transfer device. Specifically, in some embodiments, a spring can be disposed within a housing of a transfer device and can be stored in a first configuration, in which the spring has a relatively high potential energy (e.g., compressed or loaded). In such embodiments, a user can manipulate the device to transition the spring from the first configuration to a second configuration, thereby exerting a force associated with converting potential energy to kinetic energy. In other words, the spring can expand and/or otherwise reconfigure to the second configuration and in turn, can exert a force on, for example, an actuator mechanism, a plunger, and/or the like to move the actuator mechanism, plunger, and/or the like relative to the housing. Thus, such a transfer device can be at least partially automatically actuated.

While the embodiments described herein include a housing (e.g., the housings 110, 210, 310, 410, 510, 610, and 710) that define a single volume within which an actuator mechanism (e.g., the actuator mechanisms 120, 220, 320, 420, 520, 620, and 720, respectively) are disposed, in other embodiments, a transfer device can include a housing that defines multiple volumes, which can be in fluid communication or can be fluidically isolated from each other. Similarly, an actuator mechanism can include a corresponding number of plungers and/or the like. For example, in some embodiments, a housing can define a first volume and a second volume and an actuator mechanism can be, for example, monolithically constructed to include a first plunger and a second plunger. In such embodiments, the first volume can be configured to movably receive at least a portion of the first plunger and the second volume can be configured to movably receive at least a portion of the second plunger. Moreover, the first volume and the second volume can each be in fluid communication with an inlet port of the housing. Thus, as described in detail above, a user can manipulate the actuator mechanism to move the first plunger and the second plunger within the first volume and the second volume, respectively, to draw a fluid therein. In some instances, the user can actuate the actuator mechanism to move the first plunger and the second plunger in a substantially concurrent process. In other embodiments, the first plunger can be actuated independent of the second plunger.

Although the housing is described as defining two volumes and the actuator mechanism is described as including two plungers, in other embodiments, the housing can define more than two volumes and the actuator mechanism can include more than two plungers (e.g., three, four, or more). For example, in some embodiments, a syringe-based transfer device can include a housing that defines four volumes each of which movably receives a different plunger (i.e., four plungers). In such embodiments, each volume can be in fluid communication with a separate transfer adapter and/or the like, which in turn, can allow the syringe-based transfer device to fill, for example, four external fluid reservoirs substantially concurrently or in independent processes.

Similarly, while the transfer devices 100, 200, 300, 400, 500, 605, and 700 are described above as defining a single pre-sample reservoir, in other embodiments, a transfer device can include any suitable number of pre-sample reservoirs, as described above with reference to transfer device 100. For example, in some embodiments, an actuator mechanism and/or the like can define a fluid reservoir (e.g., a pre-sample reservoir) having one or more chambers or the like (e.g., one, two, three, four, or more). In such embodiments, the transfer device can be configured to transfer a pre-sample volume of bodily-fluid into one or more of the chambers forming the pre-sample reservoir. In some embodiments, the pre-sample volume of bodily-fluid can be transferred to the chambers substantially concurrently. In other embodiments, the pre-sample volume of bodily-fluid can be transferred to each chamber serially. That is to say, the transfer device can transfer a first portion of the pre-sample volume of bodily-fluid into a first chamber and once the first chamber is filled to a desired level, the transfer device can transfer a second portion of the pre-sample volume of bodily-fluid into a second chamber, and so on. In some instances, the transfer device is automatically switched, transitioned, and/or actuated such that the transfer of bodily-fluid into the first chamber is stopped and the transfer of bodily-fluid into the second chamber is initiated. In other embodiments, the transfer device can transition in response to a manual and/or user input.

While some of the transfer devices 100, 200, 300, 400, 500, 605, and/or 700 are described above as being configured to couple to a single external fluid reservoir (see e.g., FIG. 24) via the respective housing and/or transfer adapter, in other embodiments, a transfer device can be configured to couple to one or more external fluid reservoirs. For example, in some embodiments, a transfer device can include an adapter configured to establish fluid communication with two fluid reservoirs contemporaneously. In some instances, a user can manipulate such a transfer device to transfer a sample volume of bodily-fluid (as described above) and then can manipulate the transfer device such that the sample volume of bodily-fluid is distributed into the two fluid reservoirs. In some instances, the sample volume of bodily-fluid can be equally distributed between the two fluid reservoirs and can be transferred thereto in a substantially concurrent process. In other instances, the sample volume can be transferred in a serial process (e.g., one after the other) and the sample volume need not be equally distributed therebetween.

Although not shown and/or described herein, in some embodiments, a transfer device can be preassembled with a sample bottle, culture bottle, and/or any other suitable fluid reservoir, for example, during manufacturing. By way of example, in some embodiments, a fluid reservoir can be coupled to and/or otherwise placed in fluid communication with, for example, an adapter of a transfer device during a manufacturing process. In such embodiments, the fluid reservoir can be coupled to the device in a sterile environment or the like such as, for example, an ethylene oxide environment.

The specific configurations of the various components can also be varied. For example, the size and specific shape of the various components can be different from the embodiments shown, while still providing the functions as described herein. More specifically, the size and shape of the various components can be specifically selected for a desired rate of bodily-fluid flow into a fluid reservoir.

Where methods and steps described above indicate certain events occurring in certain order, the ordering of certain steps may be modified while remaining in accordance with the variations of the invention. Additionally, certain steps may be performed concurrently in a parallel process when possible, as well as performed sequentially as described above. In some instances, certain steps may be partially completed before proceeding to subsequent steps. Moreover, while methods and uses are specifically described above, it is to be understood that they are presented by way of example and not limitation. For example, while the examples of use of the devices included herein describe sequestering a pre-sample volume and/or a predetermined volume of bodily-fluid prior to withdrawing a subsequent sample volume and then disposing of the pre-sample volume, in some embodiments, the pre-sample volume of bodily-fluid can also be used for testing. For example, in some instances, a pre-sample volume of bodily-fluid can be used for testing procedures that are not sensitive to contamination.

What is claimed:

1. An apparatus, comprising:
a housing defining an inner volume, the housing having an inlet port in fluid communication with the inner volume and an outlet port in fluid communication with the inner volume, the inlet port configured to receive bodily-fluid from a patient;
an actuator mechanism movably disposed within the inner volume of the housing, the actuator mechanism configured to be transitioned from a first configuration to a second configuration to define a pre-sample reservoir in selective fluid communication with the inlet port, the pre-sample reservoir configured to receive a pre-sample volume of bodily-fluid, the actuator mechanism configured to be moved from a first position to a second position after the pre-sample reservoir receives the pre-sample volume of bodily-fluid to place the inlet port in fluid communication with the outlet port; and
an adapter movably coupled to the housing, a portion of the adapter and the housing collectively defining a sample reservoir in fluid communication with the outlet port and fluidically isolated from the pre-sample reservoir, the sample reservoir configured to be in fluid communication with the inlet port when the actuator mechanism is in the second position such that movement of a portion of the adapter disposed in the housing and independent of the actuator mechanism transfers a sample volume of bodily-fluid into the sample reservoir,
the adapter configured to be fluidically coupled to an external fluid reservoir after the sample volume of bodily-fluid is disposed in the sample reservoir to transfer at least a portion of the sample volume of bodily-fluid into the external fluid reservoir.

2. The apparatus of claim 1, wherein the actuator mechanism has a first member and a second member, a portion of the first member being movably disposed within the second member.

3. The apparatus of claim 2, wherein the first member is configured to move relative to the housing and the second member to transition the actuator mechanism from the first configuration to the second configuration.

4. The apparatus of claim 3, wherein the first member and the second member move together after the actuator mechanism is in the second configuration to move the actuator mechanism from the first position to the second position.

5. The apparatus of claim 2, wherein the first member includes a plunger, the second member includes a first plunger and a second plunger, a volume collectively defined by the housing and the first member between the plunger of the first member and the first plunger of the second member forming the pre-sample reservoir.

6. The apparatus of claim 5, wherein a volume collectively defined by the housing and the second member between the first plunger and the second plunger of the second member defining at least a portion of a fluid flow path between the inlet port and the sample reservoir.

7. The apparatus of claim 1, wherein the outlet port is separate from the inlet port.

8. The apparatus of claim 1, wherein the adapter has a puncture member in fluid communication with the sample reservoir.

9. The apparatus of claim 8, wherein the adapter is configured to receive the external fluid reservoir such that the puncture member punctures a seal of the external fluid reservoir.

10. The apparatus of claim 1, further comprising:
a rack coupled to a portion of the actuator mechanism, at least a portion of the rack being disposed within a channel defined by an outer surface of the housing; and
an actuator lever rotatably coupled to the housing, the actuator lever configured to selectively engage the rack such that a rotation of the actuator lever relative to the housing moves the rack in a proximal direction, at least a portion of the actuator mechanism configured to move with the rack as the rack moves in the proximal direction.

11. The apparatus of claim 10, wherein, the actuator lever is configured to rotate relative to the housing in response to a force exerted on the actuator lever by a user.

12. The apparatus of claim 1, further comprising:
a slider coupled to a portion of the actuator mechanism, at least a portion of the slider being disposed within a channel defined by an outer surface of the housing, the slider configured to be moved in a proximal direction in response to a manual force exerted by a user.

13. A method of using a syringe-based fluid transfer device having a housing, an actuator mechanism, and an adapter, the method comprising:
establishing fluid communication between a patient and an inlet port of the syringe-based transfer device;
moving a first member of the actuator mechanism relative to the housing from a first position to a second position, a portion of the first member moving within a second member of the actuator mechanism such that the first member in the second position and the second member collectively define a pre-sample reservoir, the pre-sample reservoir being in fluid communication with the inlet port as the first member is moved from the first position to the second position;

transferring a pre-sample volume of bodily-fluid to the pre-sample reservoir;

moving the first member relative to the housing from the second position to a third position such that (1) the pre-sample reservoir is sequestered from the inlet port and (2) the inlet port is in fluid communication with the adapter, the second member being moved by the first member when the first member moves from the second position to the third position;

transitioning the adapter from a first configuration to a second configuration and independent of the actuator mechanism, a portion of the adapter and a portion of the housing collectively defining a sample reservoir fluidically isolated from the pre-sample reservoir, the sample reservoir being in fluid communication with the patient after the first member is moved from the second position to the third position; and transferring a sample volume of bodily-fluid to the sample reservoir in response to movement of a portion of the adapter disposed in the housing.

14. The method of claim 13, wherein the syringe-based transfer device includes (1) a rack at least partially disposed within a channel defined by an outer surface of the housing and coupled to the first member and (2) an actuator lever rotatably coupled to the housing and configured to selectively engage the rack such that a rotation of the actuator lever relative to the housing moves the rack in a proximal direction, the moving the first member relative to the housing from the first position to the second position includes moving the first member in response to a force exerted on the actuator lever operable to rotate the actuator lever relative to the housing.

15. The method of claim 13, wherein the syringe-based transfer device includes a slider coupled to a portion of the actuator mechanism, at least a portion of the slider being disposed within a channel defined by an outer surface of the housing, the moving the first member relative to the housing from the first position to the second position includes moving the first member in response to a force exerted on the slider operable to move the slider in a proximal direction.

16. The method of claim 13, further comprising:

establishing fluid communication between the syringe-based transfer device and an external fluid reservoir after the transferring the sample volume of bodily-fluid to the sample reservoir.

* * * * *